United States Patent
Liu et al.

(10) Patent No.: US 11,602,534 B2
(45) Date of Patent: Mar. 14, 2023

(54) PYRIMIDINE DERIVATIVE KINASE INHIBITORS

(71) Applicant: HEFEI INSTITUTES OF PHYSICAL SCIENCE, CHINESE ACADEMY OF SCIENCES, Anhui (CN)

(72) Inventors: Qingsong Liu, Anhui (CN); Jing Liu, Anhui (CN); Xiaofei Liang, Anhui (CN); Beilei Wang, Anhui (CN); Kailin Yu, Anhui (CN); Zongru Jiang, Anhui (CN); Cheng Chen, Anhui (CN); Chen Hu, Anhui (CN); Wenchao Wang, Anhui (CN); Fengming Zou, Anhui (CN); Qingwang Liu, Anhui (CN); Feng Li, Anhui (CN); Wenliang Wang, Anhui (CN); Li Wang, Anhui (CN)

(73) Assignee: Hefei Institutes of Physical Science, Chinese Academy of Sciences, Anhui (CN)

( * ) Notice: Subject to any disclaimer, the term of this patent is extended or adjusted under 35 U.S.C. 154(b) by 93 days.

(21) Appl. No.: 16/956,860

(22) PCT Filed: Dec. 26, 2017

(86) PCT No.: PCT/CN2017/118614
§ 371 (c)(1),
(2) Date: Jun. 22, 2020

(87) PCT Pub. No.: WO2019/119486
PCT Pub. Date: Jun. 27, 2019

(65) Prior Publication Data
US 2020/0323850 A1 Oct. 15, 2020

(30) Foreign Application Priority Data

Dec. 21, 2017 (CN) .......................... 201711394166.6

(51) Int. Cl.

| | |
|---|---|
| *A61K 31/505* | (2006.01) |
| *A61P 35/02* | (2006.01) |
| *A61K 31/506* | (2006.01) |
| *A61K 31/5377* | (2006.01) |
| *C07D 239/47* | (2006.01) |
| *C07D 401/12* | (2006.01) |
| *C07D 401/14* | (2006.01) |
| *C07D 403/04* | (2006.01) |
| *C07D 403/12* | (2006.01) |
| *C07D 405/12* | (2006.01) |
| *C07D 413/14* | (2006.01) |

(52) U.S. Cl.
CPC .......... *A61K 31/505* (2013.01); *A61K 31/506* (2013.01); *A61K 31/5377* (2013.01); *A61P 35/02* (2018.01); *C07D 239/47* (2013.01); *C07D 401/12* (2013.01); *C07D 401/14* (2013.01); *C07D 403/04* (2013.01); *C07D 403/12* (2013.01); *C07D 405/12* (2013.01); *C07D 413/14* (2013.01)

(58) Field of Classification Search
None
See application file for complete search history.

(56) References Cited

U.S. PATENT DOCUMENTS

| | | |
|---|---|---|
| 4,100,274 A | 7/1978 | Dutta et al. |
| 4,636,505 A | 1/1987 | Tucker |
| 4,659,516 A | 4/1987 | Bowler et al. |
| 5,010,099 A | 4/1991 | Gunasekera et al. |
| 5,843,901 A | 12/1998 | Roeske |
| 2004/0053908 A1 | 3/2004 | Funahashi et al. |

FOREIGN PATENT DOCUMENTS

| | | |
|---|---|---|
| CN | 1478078 A | 2/2004 |
| CN | 101291917 A | 10/2008 |

(Continued)

OTHER PUBLICATIONS

Cherian, J. et al., J. Med. Chem 2016 vol. 59, pp. 3063-3078.*
International Search Report dated Aug. 29, 2018 issued in PCT/CN2017/118614.
Cherian, Joseph, "Structure-Activity Relationship Studies of Mitogen Activated Protein Kinase Interacting Kinase (MNK) 1 & 2 and BCR-ABL1 Inhibitors Targeting Chronic Myeloid Leukemic Cells", Journal of Medicinal Chemistry (Mar. 24, 2016), vol. 59, No. 7, pp. 3063-3078.

(Continued)

*Primary Examiner* — Brandon J Fetterolf
*Assistant Examiner* — Manahil Mirghani Ali Abdalhameed
(74) *Attorney, Agent, or Firm* — Scully, Scott, Murphy & Presser, P.C.

(57) ABSTRACT

The present invention relates to a kinase inhibitor, comprising a compound of Formula I or a pharmaceutically acceptable salt, solvate, ester, acid, metabolite or prodrug thereof. The present invention also relates to a pharmaceutical composition comprising the kinase inhibitor, and to uses and methods for using these compounds and compositions to inhibit the activity of wild-type FLT3, mutant FLT3-ITD, PDGFRα and/or PDGFRβ kinase in a cell or a subject, as well as uses and methods of these compounds and compositions to preventing or treating kinase-associated conditions in a subject.

Formula I

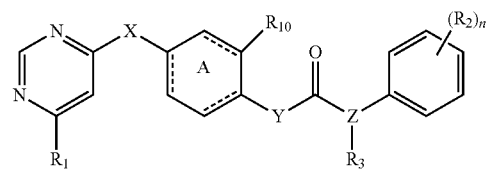

8 Claims, 5 Drawing Sheets

(56) References Cited

FOREIGN PATENT DOCUMENTS

| | | |
|---|---|---|
| CN | 101541766 A | 9/2009 |
| EP | 0520722 A1 | 9/1992 |
| EP | 0564409 A1 | 10/1993 |
| EP | 0566226 A1 | 10/1993 |
| EP | 0769947 A1 | 5/1997 |
| EP | 0787722 A1 | 8/1997 |
| EP | 0837063 A1 | 4/1998 |
| JP | 2005-527622 A | 9/2005 |
| JP | 2007-515400 A | 6/2007 |
| JP | 2010-507573 A | 3/2010 |
| JP | 2015-525739 A | 9/2015 |
| WO | WO 94/10202 A1 | 5/1994 |
| WO | WO 96/10028 A1 | 4/1996 |
| WO | WO 96/33980 A1 | 10/1996 |
| WO | WO 96/40116 A1 | 12/1996 |
| WO | WO 97/02266 A1 | 1/1997 |
| WO | WO 97/07131 A1 | 2/1997 |
| WO | WO 97/08193 A1 | 3/1997 |
| WO | WO 97/28161 A1 | 8/1997 |
| WO | WO 97/30034 A1 | 8/1997 |
| WO | WO 97/32879 A1 | 9/1997 |
| WO | WO 97/38983 A1 | 10/1997 |
| WO | WO 97/49688 A1 | 12/1997 |
| WO | WO 97/49706 A1 | 12/1997 |
| WO | WO 98/10767 A2 | 3/1998 |
| WO | WO 98/11223 A1 | 3/1998 |
| WO | WO 98/35958 A1 | 8/1998 |
| WO | WO 99/03854 A1 | 1/1999 |
| WO | WO 99/17804 A1 | 4/1999 |
| WO | WO 00/09495 A1 | 2/2000 |
| WO | WO 00/27819 A2 | 5/2000 |
| WO | WO 00/27820 A1 | 5/2000 |
| WO | WO 00/37502 A2 | 6/2000 |
| WO | WO 00/59509 A1 | 10/2000 |
| WO | WO 01/55114 A1 | 8/2001 |
| WO | WO 01/58899 A1 | 8/2001 |
| WO | WO 02/22577 A2 | 3/2002 |
| WO | 02/32872 A1 | 4/2002 |
| WO | WO 02/92599 A1 | 11/2002 |
| WO | WO 03/13541 A1 | 2/2003 |
| WO | 03/099771 A2 | 12/2003 |
| WO | 2005/051366 A2 | 6/2005 |
| WO | 2007/010013 A2 | 1/2007 |
| WO | WO-2007076474 A1 * | 7/2007 ........... C07D 401/04 |
| WO | 2008/077548 A1 | 7/2008 |
| WO | 2010/123870 A1 | 10/2010 |
| WO | 2011/025798 A1 | 3/2011 |
| WO | 2012/139499 A1 | 10/2012 |
| WO | 2014/000418 A1 | 1/2014 |
| WO | WO 2017038873 A1 | 3/2017 |

OTHER PUBLICATIONS

Gandin, Valentina et al., "Targeting kinases with anilinopyrimidines: discovery of N-phenyl-N'-[4-(pyrimidin-4-ylamino)phenyl]urea derivatives as selective inhibitors of class III receptor tyrosine kinase subfamily", Scientific Reports (Nov. 16, 2015), vol. 5, 16750, pp. 1-16.

Wang, Taijin et al., "Discovery of novel CDK8 inhibitors using multiple crystal structures in docking-based virtual screening", European Journal of Medicinal Chemistry (Mar. 31, 2017), vol. 129, pp. 275-286.

Kottaridis, P.D., et al., "FLT3 mutations and leukaemia", British Journal of Haematology (2003), vol. 122, No. 4, pp. 523-538.

Ansari-Lari, Ali et al., "FLT3 mutations in myeloid sarcoma", British Journal of Haematology (2004), vol. 126, No. 6, pp. 785-791.

Lyman, S.D. et al., "Characterization of the protein encoded by the flt3 (flk2) receptor-like tyrosine kinase gene", Oncogene (1993), vol. 8, pp. 815-822.

Berge et al. "Pharmaceutical Salts", J. Pharm. Sci. (1977), vol. 66, pp. 1-19.

Prewett, M. et al., "Antivascular Endothelial Growth Factor Receptor (Fetal Liver Kinase 1) Monoclonal Antibody Inhibits Tumor Angiogenesis and Growth of Several Mouse and Human Tumors", Cancer Research 59 (Oct. 15, 1999), pp. 5209-5218.

Zhu, Z. et al., "Inhibition of Vascular Endothelial Growth Factor-induced Receptor Activation with Anti-Kinase Insert Domain-containing Receptor Single-Chain Antibodies from a Phage Display Library", Cancer Research 58 (Aug. 1, 1998), pp. 3209-3214.

Mordenti, J. et al. "Efficacy and Concentration-Response of Murine Anti-VEGF Monoclonal Antibody in Tumor-Bearing Mice and Extrapolation to Humans*", Toxicologic Pathology (1999), vol. 27, No. 1, pp. 14-21.

O' Reilly, M.S. et al., "Angiostatin: A Novel Angiogenesis Inhibitor that Mediates the Suppression of Metastases by a Lewis Lung Carcinoma", Cell (Oct. 21, 1994), vol. 79, pp. 315-328.

Chen Y. et al., "Integrated Bioinformatics, Computational and Experimental Methods to Discover Novel Raf/Extracellular-Signal Regulated Kinase (ERK) Dual Inhibitors Against Breast Cancer Cells", European Journal of Medicinal Chemistry 127:997-1011 (2017).

Deibler K.K. et al., "A Chemical Probe Strategy for Interrogating Inhibitor Selectivity Across the MEK Kinase Family", ACS Chemical Biology 12:1245-1256 (2017).

Paunovic A.I. et al., "Phenotypic Screen for Cardiac Regeneration Identifies Molecules With Differential Activity in Human Epicardium-Derived Cells Versus Cardiac Fibroblasts", ACS Chemical Biology 12:132-141 (2017).

Weisberg E. et al., "Antileukemic Effects of the Novel, Mutant FLT3 Inhibitor NVP-AST487: Effects on PKC412-Sensitive and -Resistant FLT3-Expressing Cells", Blood 112(13):5161-5170 (Dec. 15, 2008).

Australian Examination Report dated Jan. 22, 2021 received in Australian Application No. 2017444054.

Weisberg E. et al., "Antileukemic Effects of Novel First- and Second-Generation FLT3 Inhibitors: Structure-Affinity Comparison", Genes & Cancer 1(10):1021-1032 (Oct. 1, 2011).

European Extended Supplementary Search Report dated Jun. 29, 2021 received in European Application No. 17 935 274.5.

* cited by examiner

PYRIMIDINE DERIVATIVE KINASE INHIBITORS

TECHNICAL FIELD

The present invention relates to novel kinase inhibitor compounds, pharmaceutical compositions comprising the compounds, as well as uses and methods of using these compounds or compositions to reduce or inhibit the activity of wild-type FLT3, mutant FLT3-ITD, PDGFRα and/or PDGFRβ kinase in a cell or a subject, and uses and methods of using these compounds or compositions for preventing or treating kinase-associated conditions in a subject.

BACKGROUND OF THE INVENTION

Protein kinases are enzymatic components of the signal transduction pathways which catalyze the transfer of the terminal phosphate from ATP to the hydroxy group of tyrosine, serine and/or threonine residues of proteins. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular diseases, schizophrenia, rheumatoid arthritis, atherosclerosis, cardiovascular disease, and cancer. Therefore, inhibitors of protein kinases have particular application in the treatment of human and animal disease.

FLT3 (Fms-like tyrosine kinase 3), similarly as c-Kit, c-FMS and PDGFR, belongs to members of receptor tyrosine kinase III (RTK III) family, and its protein structure includes an extracellular region consisted of five immunoglobulin (Ig)-like domains, a transmembrane region, an intracellular juxtamembrane (JM) region, as well as two tyrosine kinase (TK) domains interrupted by a kinase insert in the intracellular region (S. D. Lyman et al., *Oncogene*, 1993, 8, 815-822). In 1996, the FLT3 mutations were first identified in acute granulocytic leukemia (AML) cells, and the mutation type was internal tandem duplications (FLT3/ITD). In recent years, many studies have demonstrated that the FLT3 activation mutations played a very important pathological role in the development of AML and the progression of the disease. AML patients having FLT3/ITD activation mutations generally have unique clinical features, such as high peripheral blood leucocyte count, poor clinical prognosis, and easy relapse, and the like. Since detecting assays for FLT3 activation mutations are easily practicable, more and more researchers are committed to developing FLT3 as a conventional detection object of AML for guiding the therapy and prognostic prediction in AML patients, and as a detection means of minimal residual leukemia, and as a new target for chemotherapy in leukemia patients.

Hematological malignancies are cancers of body's blood forming and immune systems, bone marrow and lymphatic tissues. Whereas in normal bone marrow, FLT3 expression is restricted to early progenitor cells, in hematological malignancies FLT3 is expressed at high levels or FLT3 mutates, causing an uncontrolled induction of the FLT3 receptor and downstream molecular pathway, possibly Ras activation. Hematological malignancies include leukemias, lymphomas (non-Hodgkin's lymphoma), Hodgkin's disease (also called Hodgkin's lymphoma), and myeloma—for instance, acute lymphocytic leukemia (ALL), acute granulocytic leukemia or acute myeloid leukemia (AML), acute promyelocytic leukemia (APL), chronic lymphocytic leukemia (CLL), chronic granulocytic leukemia (CML), chronic neutrophilic leukemia (CNL), acute undifferentiated leukemia (AUL), anaplastic large-cell lymphoma (ALCL), adult T-cell ALL, AML with trilineage myelodysplasia (AML/TMDS), mixed lineage leukemia (MLL), myelodysplasia syndromes (MDSs), myeloproliferative disorders (MPD), multiple myeloma (MM) and myeloid sarcoma (Kottaridis, P. D., R. E. Gale et al., FLT3 mutations and leukaemia, British Journal of Haematology, 2003, 122(4):523-38; Ansari-Lari, Ali et al., FLT3 mutations in myeloid sarcoma, British Journal of Haematology, 2004, 126(6):785-91).

It has been confirmed that there are mainly two classes of FLT3 activation mutations: internal tandem duplications (ITD) and point mutation (PM) in the activation loop (of TKD). Both classes of FLT3 activation mutations can cause spontaneous phosphorylation of FLT3, which leads to ligand-independent constitutive activation of FLT3, which further activates abnormal signal transduction downstream thereof, thereby acting to promote proliferation and inhibit apoptosis, as a result leukemia patients with the mutant phenotype have poor clinical prognosis.

Currently targeted inhibition of FLT3 and mutant FLT3 has become a research focus, mainly on developing small-molecule tyrosine kinase inhibitors, which inhibit the kinase activity by competing with FLT3 tyrosine kinase for ATP binding sites. As a FLT3 kinase inhibitor, PKC412, for example, has been available on the market. However, in spite of the effect of PKC412 on FLT3 and FLT3/ITD, it also strongly inhibits cKIT, and the dual inhibition of cKIT and FLT3 will incur strong marrow toxicity. Therefore, it is important to explore a kinase inhibitor that selectively inhibits FLT3-ITD. Disclosed herein is a novel family of kinase inhibitors.

SUMMARY OF THE INVENTION

The present invention relates to a novel kinase inhibitor, which comprises a compound of Formula I or a pharmaceutically acceptable salt, solvate, ester, acid, metabolite or prodrug thereof:

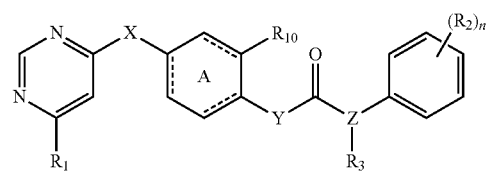

Formula I wherein A represents a benzene ring or cyclohexyl ring;
X is selected from O, S, and NH;
Y and Z are respectively selected from C and N, with the provision that at least one of Y and Z is N;
$R_1$ is selected from amino, $C_{1-6}$alkylamino, $C_{3-6}$cycloalkylamino, $C_{2-6}$acylamino, —(NR$_4$)-L-R$_5$, $C_{2-6}$alkenylcarbonylamino, $C_{3-6}$cycloalkylcarbonylamino,

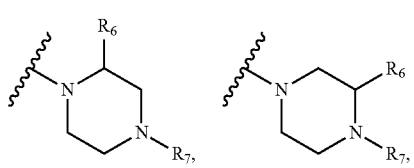

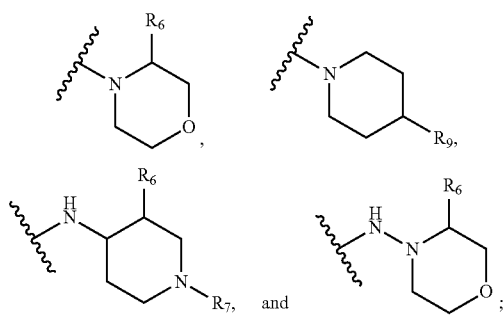

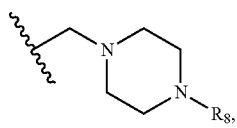

(R$_2$)$_n$ represents n independent R$_2$ substituents attached to the ortho-, meta-, or para-position of the benzene ring, wherein n is an integer of 0-3, R$_2$ is independently selected from halo, C$_{1-6}$alkyl, C$_{1-6}$haloalkyl, C$_{1-6}$alkoxy, phenyl, phenoxy, 4-methylimidazolyl, hydroxy, nitro, C$_{1-6}$alkylsulfonyl, and or two adjacent R$_2$ form together a benzene ring or dioxolane;

R$_3$ is selected from hydrogen, hydroxy, C$_{1-6}$alkyl, C$_{1-6}$alkoxy, amino, and amino protected with an amino-protecting group;

R$_{10}$ is selected from hydrogen and methyl;

R$_4$ is selected from hydrogen and methyl;

R$_5$ is selected from hydroxy, nitro, amino, amino protected with an amino-protecting group, C$_{1-6}$ alkylamino, aminoacyl, C$_{1-6}$ alkylaminoacyl, C$_{2-6}$ acylamino, C$_{2-6}$ alkenylcarbonylamino, carboxyl, an ester group, C$_{1-6}$ alkoxy, phenyl, pyrrolidinyl, thienyl, furanyl, morpholinyl, and p-methoxyphenyl;

R$_6$ is selected from hydrogen, C$_{1-6}$ alkyl, and C$_{1-6}$ hydroxyalkyl;

R$_7$ is selected from hydrogen, C$_{1-6}$ alkyl, amino-protecting group, C$_{2-6}$ alkanoyl, C$_{1-6}$ alkylsulfonyl, and C$_{1-6}$alkoxyC$_{1-6}$alkyl;

R$_8$ is selected from hydrogen and C$_{1-6}$alkyl;

R$_9$ is selected from amino protected with an amino-protecting group, morpholinyl, and piperazinyl with its N atom substituted with C$_{1-6}$alkyl or C$_{1-6}$alkylsulfonyl;

L is selected from C$_{1-4}$ straight or branched alkylene, C$_{3-6}$cycloalkylene and phenylene;

the amino-protecting group is independently selected from pivaloyl, tert-butoxycarbonyl, benzyloxycarbonyl, 9-fluorenylmethoxycarbonyl, benzyl, p-methoxybenzyl, allyloxycarbonyl, and trifluoroacetyl.

In preferred aspects, the kinase inhibitor of the present invention comprises the following compounds of Formula Ia, Ib, Ic and Id, or pharmaceutically acceptable salts, solvates, esters, acids, metabolites or prodrugs thereof:

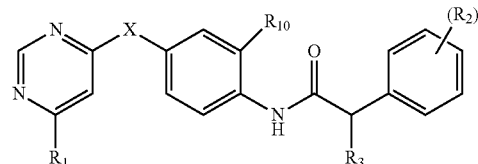

Formula Ia

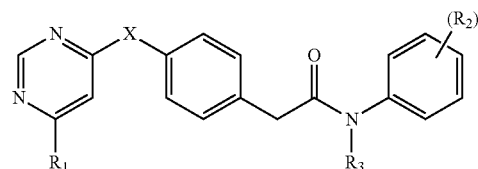

Formula Ib

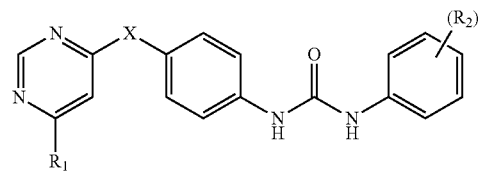

Formula Ic

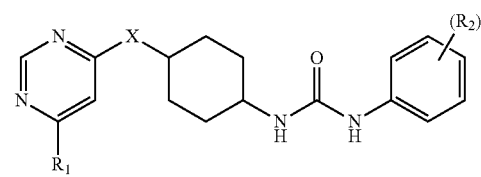

Formula Id wherein X, R$_1$, (R$_2$)$_n$, R$_3$ and R$_{10}$ are as defined above.

Further preferably, the kinase inhibitor of the present invention comprises the compounds of Formula Ia, or pharmaceutically acceptable salts, solvates, esters, acids, metabolites or prodrugs thereof, wherein X is selected from O, S, and NH; R$_1$ is selected from C$_{2-6}$acylamino and —(NR$_4$)-L-R$_5$; (R$_2$)$_n$ represents independent R$_2$ substituents attached to the ortho-, meta-, or para-position of the benzene ring, wherein n is an integer of 0-3, R$_2$ is independently selected from halo, C$_{1-6}$alkyl, C$_{1-6}$haloalkyl, C$_{1-6}$alkoxy, phenoxy, hydroxy, and nitro, or two adjacent R$_2$ form together a benzene ring; R$_3$ is selected from hydrogen, hydroxy, and C$_{1-6}$alkyl; R$_{10}$ is hydrogen; R$_4$ is hydrogen; R$_5$ is selected from hydroxy, and C$_{1-6}$alkoxy; L is selected from C$_{1-4}$ straight or branched alkylene.

Further preferably, the kinase inhibitor of the present invention comprises the compounds of Formula Ib, or pharmaceutically acceptable salts, solvates, esters, acids, metabolites or prodrugs thereof, wherein X is selected from O and NH; R$_1$ is selected from C$_{2-6}$acylamino and —(NR$_4$)-L-R$_5$; (R$_2$)$_n$ represents n independent R$_2$ substituents attached to the ortho-, meta-, or para-position of the benzene ring, wherein n is an integer of 0-3, R$_2$ is independently selected from halo, C$_{1-6}$alkyl, and C$_{1-6}$haloalkyl; R$_3$ is selected from hydrogen, and C$_{1-6}$alkyl; R$_4$ is hydrogen; R$_5$ is selected from amino, C$_{2-6}$acylamino and C$_{2-6}$alkenylcarbonylamino; L is selected from C$_{1-4}$ straight or branched alkylene.

Further preferably, the kinase inhibitor of the present invention comprises the compounds of Formula Ic, or pharmaceutically acceptable salts, solvates, esters, acids, metabolites or prodrugs thereof, wherein X is O; R$_1$ is selected from C$_{2-6}$acylamino, —(NR$_4$)-L-R$_5$,

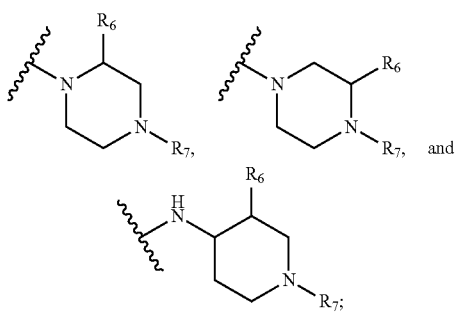

$(R_2)_n$ represents n independent $R_2$ substituents attached to the meta- and para-position of the benzene ring, wherein n is an integer of 0-2, $R_2$ is independently selected from $C_{1-6}$alkyl, $C_{1-6}$ haloalkyl, and

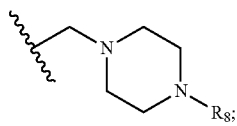

$R_4$ is selected from hydrogen and methyl; $R_5$ is selected from hydroxy, amino, amino protected with an amino-protecting group, aminoacyl, carboxyl, $C_{1-6}$alkoxy, phenyl, pyrrolidinyl, and p-methoxyphenyl; $R_6$ is selected from hydrogen, $C_{1-6}$alkyl, and $C_{1-6}$hydroxyalkyl; $R_7$ is selected from hydrogen, amino-protecting group, and $C_{2-6}$ alkanoyl; $R_8$ is selected from hydrogen and $C_{1-6}$alkyl; L is selected from $C_{1-4}$ straight or branched alkylene.

Further preferably, the kinase inhibitor of the present invention comprises the compounds of Formula Id, or pharmaceutically acceptable salts, solvates, esters, acids, metabolites or prodrugs thereof, wherein X is O; $R_1$ is selected from —$(NR_4)$-L-$R_5$; $(R_2)_n$ represents n independent $R_2$ substituents attached to the meta- and para-position of the benzene ring, wherein n is an integer of 0-2, $R_2$ is independently selected from $C_{1-6}$alkyl, and $C_{1-6}$ haloalkyl; $R_4$ is hydrogen; $R_5$ is selected from hydroxy, amino, amino protected with an amino-protecting group, and $C_{1-6}$alkoxy; L is selected from $C_{1-4}$ straight or branched alkylene.

In another aspect, the present invention provides a pharmaceutical composition comprising a therapeutically effective amount of at least one compound as provided herein, or a pharmaceutically acceptable salt, solvate, isomer, ester, acid, metabolite or prodrug thereof, and a pharmaceutically acceptable carrier or excipient, and optionally other therapeutic agents.

In a further aspect, the present invention relates to a method of using a compound of Formula (I), or a pharmaceutically acceptable salt, solvate, isomer, ester, acid, metabolite or prodrug thereof, for reducing or inhibiting the activity of wild-type FLT3, mutant FLT3/ITD, PDGFRα, and/or PDGFRβ kinase in vivo or in vitro, and use thereof.

In a further aspect, the present invention relates to use of a compound of Formula (I), or a pharmaceutically acceptable salt, solvate, isomer, ester, acid, metabolite or prodrug thereof, or a pharmaceutical composition comprising the compound of Formula (I), in preparation of a medicament for treating conditions associated with wild-type FLT3, mutant FLT3/ITD, PDGFRα, and/or PDGFRβ kinase.

Particularly, the conditions respond to inhibition of wild-type FLT3, mutant FLT3/ITD, PDGFRα, and/or PDGFRβ kinase.

According to an aspect of the present invention, the compound of the present invention selectively inhibits wild-type FLT3, mutant FLT3/ITD, PDGFRα, and/or PDGFRβ kinase. Specifically, the compound of the present invention exerts a higher inhibitory activity to wild-type FLT3, mutant FLT3/ITD, PDGFRα, and/or PDGFRβ kinase than to other kinases, especially than to cKIT. In other words, in comparison the inhibition to kinases like cKIT, the compounds of the present invention selectively inhibit the kinases wild-type FLT3, mutant FLT3/ITD, PDGFRα, and/or PDGFRβ, more preferably, selectively inhibit mutant FLT3/ITD kinase.

DESCRIPTION OF THE FIGURES

FIGS. 2a to 3e respectively illustrate the effects of Compound 5 and Compound 138 on apoptosis of MV4-11, MOLM-13, and MOLM-14 strains.

DETAILED DESCRIPTION OF THE INVENTION

Terminology

Figure 1A:
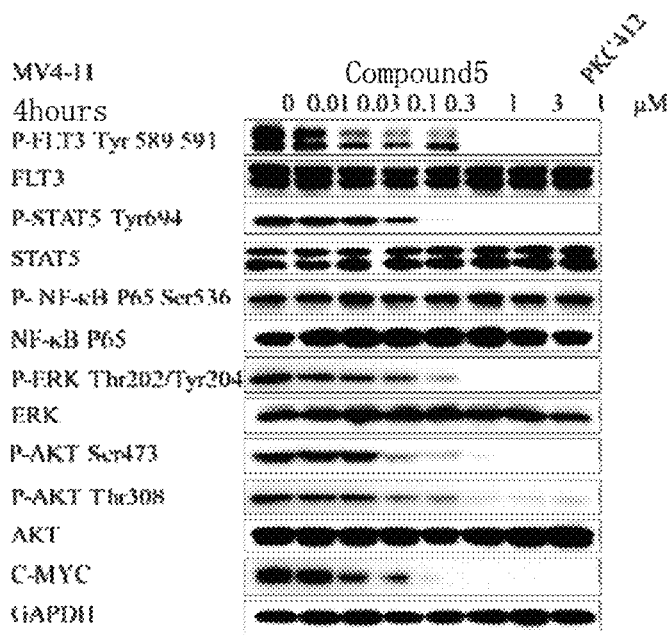
FIGS. 1a to 1f respectively illustrate the effects of Compound 5 and Compound 138 on proteins closely associated with FLT3 and on the relevant signaling pathways in MV4-11, MOLM-13, and MOLM-14 cells.
Figure 1B:
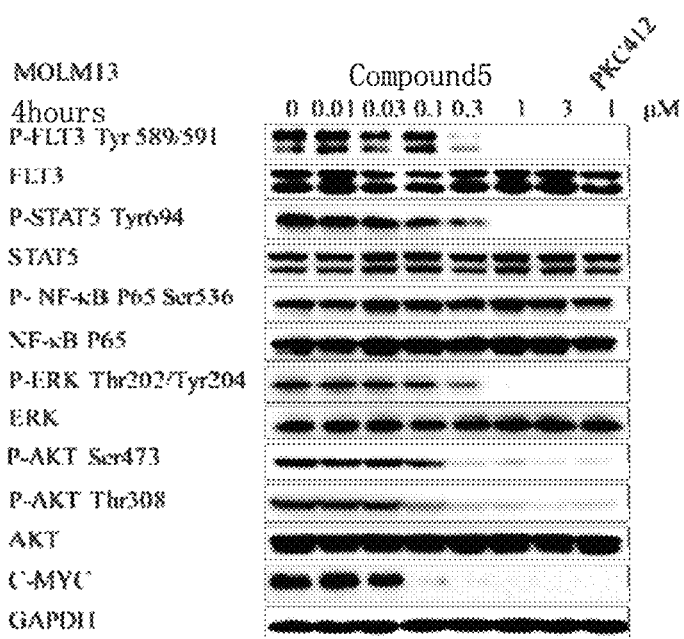
Figure 1C:
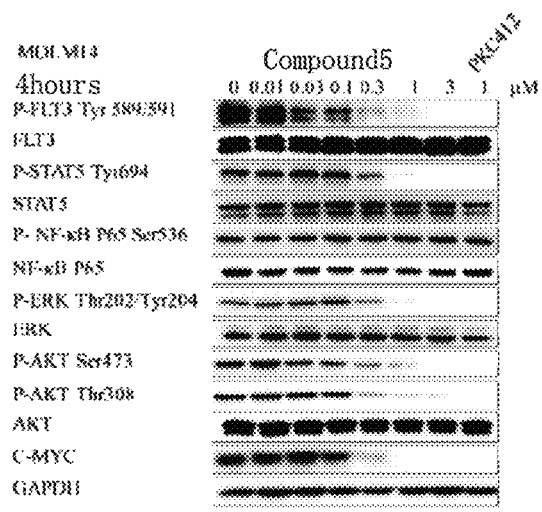
Figure 1D:
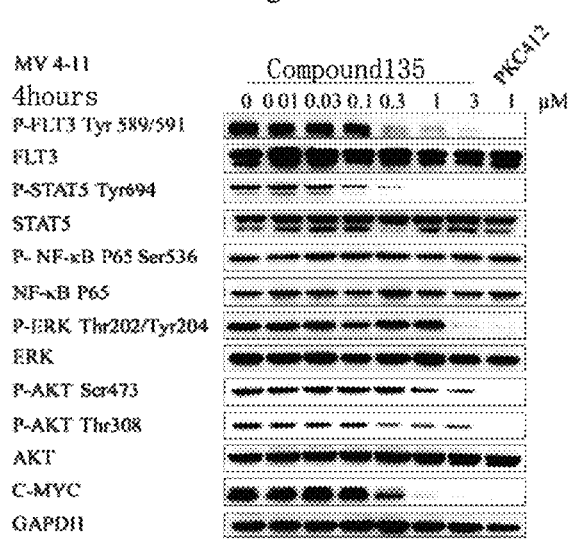
Figure 1E:
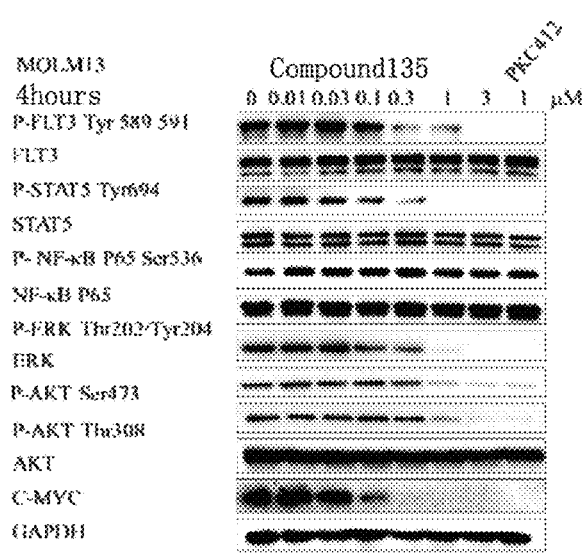
Figure 1F:
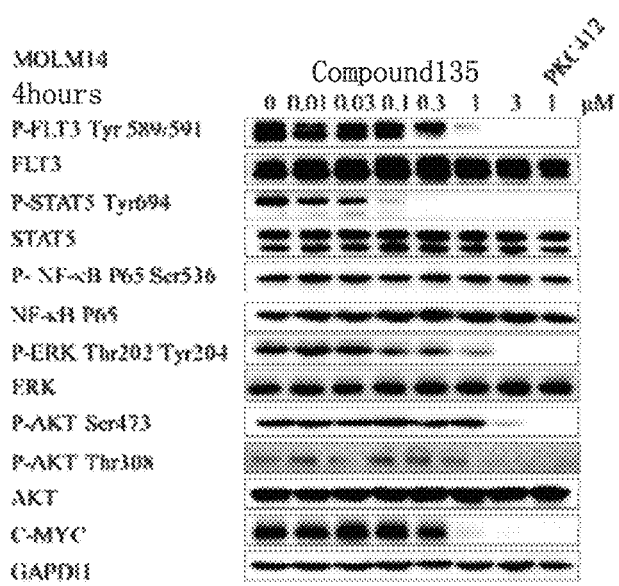
Figure 2A:
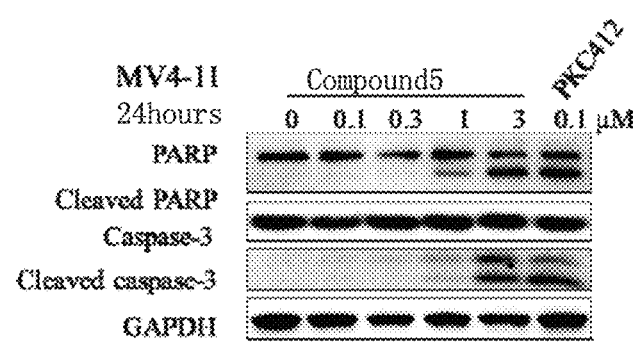
Figure 2B:
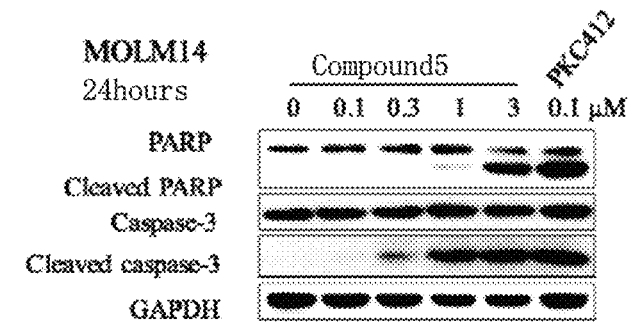
Figure 2C:
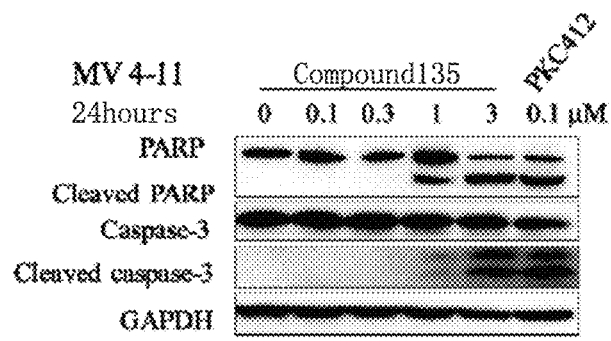
Figure 2D:
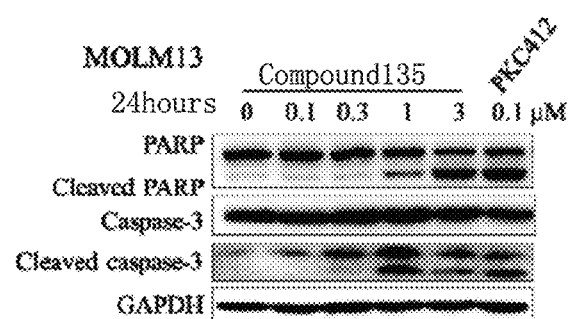
Figure 2E:
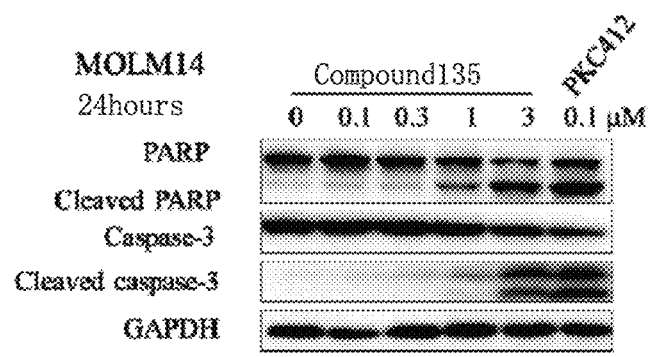

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the invention, the alkyl group is preferably an alkyl having 1 to 8 carbon atoms, more preferably a "lower alkyl" having 1 to 6 carbon atoms, and even more preferably an alkyl having 1 to 4 carbon atoms. Typical alkyl groups include, but are not limited to, methyl, ethyl, propyl, butyl, pentyl, hexyl, and the like. It should be understood that the "alkyl" as mentioned herein encompasses all configurations and conformations that may exist of the alkyl, e.g., the "propyl" as mentioned herein intends to encompass n-propyl and isopropyl, the "butyl" encompasses n-butyl, isobutyl, and tertiary butyl, the "pentyl" encompasses n-pentyl, isopentyl, neopentyl, tert-pentyl, and pent-3-yl.

The term "alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

The term "alkoxyalkyl" refers to an alkyl radical, as defined herein, substituted with an alkoxy group, as defined herein.

The term "cycloalkyl" refers to a monocyclic or polycyclic radical that contains only carbon and hydrogen. Cycloalkyl groups include groups having from 3 to 12 ring atoms. Depending on the structure, a cycloalkyl group can be a monoradical or a diradical (e.g., a cycloalkylene group). In the invention, the cycloalkyl group is preferably a cycloalkyl having 3 to 8 carbon atoms, and more preferably a "lower cycloalkyl" having 3 to 6 carbon atoms. Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl.

"Alkyl(cycloalkyl)" or "cycloalkylalkyl" means an alkyl radical, as defined herein, substituted with a cycloalkyl group, as defined herein. Non-limiting cycloalkylalkyl comprises cyclopropylmethyl, cyclobutylmethyl, cyclopentylmethyl, cyclohexylmethyl, and the like.

The term "aromatic" refers to a planar ring having a delocalized π-electron system containing 4n+2 π electrons, where n is an integer. Aromatic rings can be formed by five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "aryloxy" refers to —O-aryl, wherein aryl is as defined herein.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

"Alkyl(aryl)" or "arylalkyl" means an alkyl radical, as defined herein, substituted with an aryl group, as defined herein. Non-limiting alkyl(aryl) groups include benzyl, phenethyl, and the like.

The term "alkyl(heteroaryl)" or "heteroarylalkyl" means an alkyl radical, as defined herein, substituted with a heteroaryl group, as defined herein.

As used herein, the term "heteroalkyl" refers to an alkyl radical, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

As used herein, the term "heterocycloalkyl" or "heterocyclyl" refers to a non-aromatic ring wherein one or more atoms forming the ring is a heteroatom selected from the group consisting of nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heterocycloalkyl)" or "heterocycloalkylalkyl" means an alkyl radical, as defined herein, substituted with a heterocycloalkyl group, as defined herein.

The term "alkoxy(heterocycloalkyl)" or "heterocycloalkylalkoxy" refers to an alkoxy group, as defined herein, substituted with heterocycloalkyl, as defined herein.

The term "halo" or "halogen" means fluoro, chloro, bromo and iodo.

The terms "haloalkyl", "haloalkoxy" and "haloheteroalkyl" include alkyl, alkoxy and heteroalkyl structures in which at least one hydrogen is replaced with a halogen atom. In certain embodiments in which two or more hydrogen atoms are replaced with halogen atoms, the halogen atoms are the same or different as one another.

The term "hydroxy" refers to a radical of the formula —OH.

The term "cyano" refers to a radical of the formula —CN.

The term "ester group" refers to a chemical moiety of the formula —COOR, wherein R is selected from alkyl, cycloalkyl, aryl, heteroaryl (connected via a ring carbon) and heterocyclyl (connected via a ring carbon).

The term "amino" refers to the group —NH$_2$.

The term "aminoacyl" refers to —CO—NH$_2$.

The term "amide" or "acylamino" refers to —NR—CO—R', wherein R and R' is respectively independently hydrogen or alkyl.

The term "alkylamino" refers to an amino substituent which is further substituted with one or two alkyl groups, specifically the group —NRR', wherein R and R' are each independently selected from the group consisting of hydrogen or lower alkyl, with the proviso that —NRR' is not —NH$_2$. "Alkylamino" includes groups of compounds wherein nitrogen of —NH$_2$ is bound to at least one alkyl group. Examples of alkylamino groups include methylamino, ethylamino, etc. "Dialkylamino" includes groups wherein the nitrogen of —NH$_2$ is bound to at least two additional alkyl groups. Examples of dialkylamino groups include, but are not limited to, dimethylamino and diethylamino, etc.

The terms "arylamino" and "diarylamino" refers to an amino substituent which is further substituted with one or two aryl groups, specifically to the group —NRR' wherein R and R' are respectively independently selected from hydrogen, lower alkyl, or aryl and wherein N is respectively bound to at least one or two aryl.

The term "cycloalkylamino" refers to an amino substituent which is further substituted with one or more cycloalkyl as defined herein.

The term "heteroalkylamino" refers to an amino substituent which is further substituted with one or more heteroalkyl as defined herein.

The term "arylalkylamino" herein refers to the group —NRR' wherein R is lower aralkyl, and R' is hydrogen, lower alkyl, aryl or lower aralkyl.

The term "heteroarylamino" refers to an amino substituent which is further substituted with one or more heteroaryl as defined herein.

The term "heterocycloalkylamino" refers to an amino substituent which is substituted with heterocycloalkyl as defined herein.

The term "alkylaminoalkyl" refers to an alkyl substituent which is substituted with alkylamino as defined herein.

The term "aminoalkyl" refers to an alkyl substituent which is further substituted with one or more amino groups.

The term "aminoalkoxy" refers to an alkoxy substituent which is further substituted with one or more amino groups.

The term "hydroxyalkyl" or "hydroxylalkyl" refers to an alkyl substituent which is further substituted with one or more hydroxy groups.

The term "cyanoalkyl" refers to an alkyl substituent which is further substituted with one or more cyano.

The term "acyl" refers to a monovalent radical remaining after removing the hydroxyl from an organic or inorganic oxygenic acid which has the formula R-M(O)— wherein M is typically C.

The term "carbonyl" is an organic functional group (C=O) composed of a carbon atom double-bonded to an oxygen atom.

The term "alkanoyl" or "alkylcarbonyl" refers to a carbonyl group which is further substituted with alkyl. Typical alkanoyl includes, but not limited to, acetyl, propionyl, butanoyl, valeryl, hexanoyl, etc.

The term "arylcarbonyl" refers to a carbonyl group as defined herein substituted with an aryl group as defined herein.

The term "alkoxycarbonyl" refers to a carbonyl group further substituted with alkoxy.

The term "heterocycloalkylcarbonyl" refers to a carbonyl group further substituted with heterocycloalkyl.

The terms "alkylaminocarbonyl", "cycloalkylaminocarbonyl", "arylaminocarbonyl", "aralkylaminocarbonyl", "heteroarylaminocarbonyl" respectively refer to a carbonyl group as defined herein substituted with alkylamino, cycloalkylamino, arylamino, aralkylamino, or heteroarylamino as defined herein, respectively.

The term "alkylcarbonylalkyl" or "alkanoylalkyl" refers to alkyl further substituted with alkylcarbonyl.

The term "alkylcarbonylalkoxy" or "alkanoylalkoxy" refers to alkoxy further substituted with alkylcarbonyl.

The term "heterocycloalkylcarbonylalkyl" refers to alkyl further substituted with heterocycloalkylcarbonyl.

The term "sulfone" or "sulfonyl" refers to a functional group obtained from a sulfonic acid by removal of the hydroxyl group, specifically refers to —S(=O)$_2$—.

The term "sulfoxido" or "sulfinyl" refers to —S(=O)—.

The term "aminosulfone" or "aminosulfonyl" refers to —S(=O)$_2$—NH$_2$.

The term "alkylsulfoxido" or "alkylsulfinyl" refers to alkyl-S(=O)—.

The term "alkylsulfone" or "alkylsulfonyl" refers to —S(=O)$_2$—R, wherein R is alkyl.

The term "alkylaminosulfone" refers to sulfone as defined herein substituted with alkylamino as defined herein.

The term "alkylsulfoneamino" or "cycloalkylsulfoneamino" refers to an amino substituent as defined herein substituted with alkylsulfone or cycloalkylsulfone as defined herein.

The term "cycloalkylsulfone" and "cycloalkylsulfonyl" refers to —S(=O)$_2$—R, wherein R is cycloalkyl.

The term "alkylsulfonylamido" and "cycloalkylsulfonylamido" refers to —NH—S(=O)$_2$—R, wherein R is respectively alkyl and cycloalkyl.

The term "quaternary ammonium group" refers to —N$^+$RR'R", wherein each of R, R' and R" is independently selected from alkyl having 1-8 carbon atoms.

The term "optionally" means that the subsequently described event(s) may or may not occur, and includes both event(s), which occur, and events that do not occur. The term "optionally substituted" or "substituted" means that the referenced group may be substituted with one or more additional group(s) individually and independently selected from the group consisting of the group consisting of alkyl, cycloalkyl, aryl, heteroaryl, heterocyclyl, hydroxy, alkoxy, cyano, halo, amide, nitro, haloalkyl, amino, mesyl, alkylcarbonyl, alkoxycarbonyl, heteroarylalkyl, heterocycloalkylalkyl, aminoacyl, amino-protecting group and the like. Wherein, the amino-protecting group is preferably selected from pivaloyl, tert-butoxycarbonyl, benzyloxycarbonyl, 9-fluorenylmethoxycarbonyl, benzyl, p-methoxybenzyl, allyloxycarbonyl, and trifluoroacetyl, etc.

The terms "inhibits", "inhibiting", or "inhibitor" of a kinase, as used herein, refer to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics*, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included. In aspects, the compounds of the invention are prodrugs of any of the formulae herein.

The term "isomers" refers to compounds which have identical chemical constitution, but differ with regard to the arrangement of the atoms or groups in space, which is intended to include diastereoisomers, enantiomers, regioisomers, structural isomers, rotational isomers, tautomers, and the like. For compounds which contain one or more stereogenic centers, e.g., chiral compounds, the methods of the present invention may be carried out with an enantiomerically enriched compound, a racemate, or a mixture of diastereomers.

As used herein, the term "target protein" refers to a protein molecule or a portion of a protein capable of being bound by a selective binding compound. In certain embodiments, a target protein is FLT3.

$IC_{50}$ as used herein refers to an amount, concentration or dosage of a particular test compound that achieves a 50% inhibition of a maximal response, in an assay that measures such response.

$EC_{50}$ as used herein refers to a dosage, concentration or amount of a test compound that elicits a dose-dependent response at 50% of maximal expression of a particular response that is induced, provoked or potentiated by the particular test compound.

The $GI_{50}$ as used herein refers to a concentration of a medicament that is necessary for inhibiting 50% of cell proliferation, i.e., the medicament concentration at which the growth of cells such as cancer cells is inhibited or controlled by 50%.

The Novel Kinase Inhibitors of the Present Invention

The present invention provides a novel kinase inhibitor, comprising a compound of Formula (I) or a pharmaceutically acceptable salt, solvate, ester, acid, metabolite or prodrug thereof:

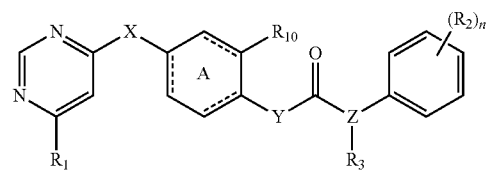

Formula I wherein A represents a benzene ring or cyclohexyl ring;
X is selected from O, S, and NH;
Y and Z are respectively selected from C and N, with the provision that at least one of Y and Z is N;
$R_1$ is selected from amino, $C_{1-6}$alkylamino, $C_{3-6}$cycloalkylamino, $C_{2-6}$acylamino, —($NR_4$)-L-$R_5$, $C_{2-6}$alkenylcarbonylamino, $C_{3-6}$cycloalkylcarbonylamino,

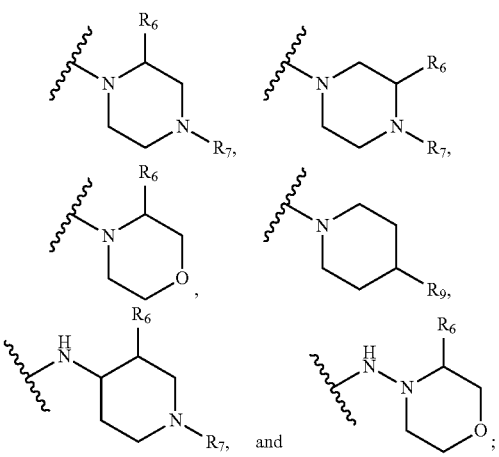

$(R_2)_n$ represents n independent $R_2$ substituents attached to the ortho-, meta-, or para-position of the benzene ring, wherein n is an integer of 0-3, $R_2$ is independently selected from halo, $C_{1-6}$alkyl, $C_{1-6}$haloalkyl, $C_{1-6}$alkoxy, phenyl, phenoxy, 4-methylimidazolyl, hydroxy, nitro, $C_{1-6}$alkylsulfonyl, and

or two adjacent $R_2$ form together a benzene ring or dioxolane;
$R_3$ is selected from hydrogen, hydroxy, $C_{1-6}$alkyl, $C_{1-6}$alkoxy, amino, and amino protected with an amino-protecting group;
$R_{10}$ is selected from hydrogen and methyl;
$R_4$ is selected from hydrogen and methyl;
$R_5$ is selected from hydroxy, nitro, amino, amino protected with an amino-protecting group, $C_{1-6}$alkylamino, aminoacyl, $C_{1-6}$alkylaminoacyl, $C_{2-6}$acylamino, $C_{2-6}$alkenylcarbonylamino, carboxyl, an ester group, $C_{1-6}$alkoxy, phenyl, pyrrolidinyl, thienyl, furanyl, morpholinyl, and p-methoxyphenyl;
$R_6$ is selected from hydrogen, $C_{1-6}$alkyl, and $C_{1-6}$hydroxyalkyl;

$R_7$ is selected from hydrogen, $C_{1-6}$alkyl, amino-protecting group, $C_{2-6}$ alkanoyl, $C_{1-6}$alkylsulfonyl, and $C_{1-6}$alkoxy$C_{1-6}$alkyl;

$R_8$ is selected from hydrogen and $C_{1-6}$alkyl;

$R_9$ is selected from amino protected with an amino-protecting group, morpholinyl, and piperazinyl with its N atom substituted with $C_{1-6}$alkyl or $C_{1-6}$alkylsulfonyl;

L is selected from $C_{1-4}$ straight or branched alkylene, $C_{3-6}$cycloalkylene and phenylene; amino-protecting group is independently selected from pivaloyl, tert-butoxycarbonyl, benzyloxycarbonyl, 9-fluorenylmethoxycarbonyl, benzyl, p-methoxybenzyl, allyloxycarbonyl, and trifluoroacetyl.

In preferred aspects, the kinase inhibitor of the present invention comprises the following compounds of Formula Ia, Ib, Ic and Id, or pharmaceutically acceptable salts, solvates, esters, acids, metabolites or prodrugs thereof:

Formula Ia

Formula Ib

Formula Ic

Formula Id wherein X, $R_1$, $(R_2)_n$, $R_3$ and $R_{10}$ are as defined above.

Further preferably, the kinase inhibitor of the present invention comprises the compounds of Formula Ia, or pharmaceutically acceptable salts, solvates, esters, acids, metabolites or prodrugs thereof, wherein, X is selected from O, S, and NH, more preferably O;

$R_1$ is selected from $C_{2-6}$acylamino (for example, acetamido, propionamido, butyramido, dimethylacetamido, pentyramido, trimethylacetamido, and hexyramido), and —(NR$_4$)-L-R$_5$, more preferably $C_{2-6}$acylamino;

$(R_2)_n$ represents independent $R_2$ substituents attached to the ortho-, meta-, or para-position of the benzene ring, wherein n is an integer of 0-3, $R_2$ is independently selected from halo, $C_{1-6}$alkyl (for example, methyl, tert-butyl, isobutyl), $C_{1-6}$haloalkyl (for example, trifluoromethyl), $C_{1-6}$alkoxy (for example, methoxy), phenoxy, hydroxy, and nitro, or two adjacent $R_2$ form together a benzene ring;

$R_3$ is selected from hydrogen, hydroxy, and $C_{1-6}$alkyl (for example, methyl), more preferably hydrogen;

$R_{10}$ is hydrogen;

$R_4$ is hydrogen;

$R_5$ is selected from hydroxy, and $C_{1-6}$alkoxy (for example, methoxy);

L is selected from $C_{1-4}$ straight or branched alkylene (for example, ethylidene).

Further preferably, the kinase inhibitor of the present invention comprises the compounds of Formula Ib, or pharmaceutically acceptable salts, solvates, esters, acids, metabolites or prodrugs thereof, wherein X is selected from O and NH, more preferably O;

$R_1$ is selected from $C_{2-6}$acylamino (for example, acetamido) and —(NR$_4$)-L-R$_5$, more preferably $C_{2-6}$acylamino;

$(R_2)_n$ represents n independent $R_2$ substituents attached to the ortho-, meta-, or para-position of the benzene ring, wherein n is an integer of 0-3, $R_2$ is independently selected from halo, $C_{1-6}$alkyl (for example, methyl), and $C_{1-6}$ haloalkyl (for example, trifluoromethyl);

$R_3$ is selected from hydrogen, and $C_{1-6}$alkyl (for example, methyl);

$R_4$ is hydrogen;

$R_5$ is selected from amino, $C_{2-6}$acylamino (for example, propionamido) and $C_{2-6}$ alkenylacylamino (for example, vinylacylamino);

L is selected from $C_{1-4}$ straight or branched alkylene (for example, ethylidene).

Further preferably, the kinase inhibitor of the present invention comprises the compounds of Formula Ic, or pharmaceutically acceptable salts, solvates, esters, acids, metabolites or prodrugs thereof, wherein X is O;

$R_1$ is selected from $C_{2-6}$acylamino (for example, acetamido, propionamido), —(NR$_4$)-L-R$_5$, $(R_2)_n$ represents n independent $R_2$ substituents attached to the meta- and para-position of the benzene ring, wherein n is an integer of 0-2, $R_2$ is independently selected from $C_{1-6}$alkyl (for example, methyl), $C_{1-6}$ haloalkyl (for example, trifluoromethyl), and $R_4$ is selected from hydrogen and methyl;

$R_5$ is selected from hydroxy, amino, amino protected with an amino-protecting group (for example, Boc), aminoacyl, carboxyl, $C_{1-6}$alkoxy (for example, methoxy), phenyl, pyrrolidinyl, and p-methoxyphenyl;

$R_6$ is selected from hydrogen, $C_{1-6}$alkyl (for example, methyl, ethyl), and $C_{1-6}$hydroxyalkyl (for example, hydroxymethyl);

$R_7$ is selected from hydrogen, amino-protecting group (for example, Boc), and $C_{2-6}$ alkanoyl (for example, acetyl, propionyl, butyryl, 2-tert-butylacetyl, 2,2-dimethylbutyryl);

$R_8$ is selected from hydrogen and $C_{1-6}$alkyl (for example, methyl, ethyl);

L is selected from $C_{1-4}$ straight or branched alkylene (for example, methylene, ethylidene, methylmethylene, methylethylidene, ethylmethylene, isopropylmethylene, et al.).

Further preferably, the kinase inhibitor of the present invention comprises the compounds of Formula Id, or pharmaceutically acceptable salts, solvates, esters, acids, metabolites or prodrugs thereof, wherein X is O;

$R_1$ is selected from —$(NR_4)$-L-$R_5$;

$(R_2)_n$ represents n independent $R_2$ substituents attached to the meta- and para-position of the benzene ring, wherein n is an integer of 0-2, $R_2$ is independently selected from $C_{1-6}$alkyl (for example, methyl), and $C_{1-6}$ haloalkyl (for example, trifluoromethyl);

$R_4$ is hydrogen;

$R_5$ is selected from hydroxy, amino, amino protected with an amino-protecting group (for example, Boc), and $C_{1-6}$alkoxy (for example, methoxy);

L is selected from $C_{1-4}$ straight or branched alkylene (for example, ethylidene).

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Described herein are novel kinase inhibitors. The pharmaceutically acceptable salts, solvates, isomers, esters, acids, pharmaceutically active metabolites and prodrugs of these compounds are also described herein.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid-addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2]oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base-addition salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a nonsolvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, microscopy, and elemental analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Present Invention and the Use Thereof

The present invention also relates to a pharmaceutical composition comprising compounds of Formula (I), (Ia), (Ib), (Ic), or (Id), or a pharmaceutically acceptable salt, solvate, isomer, ester, acid, metabolite or prodrug thereof, as an active ingredient, and a pharmaceutically acceptable carrier or excipient, and optionally other therapeutic agents.

The compounds of Formula (I), (Ia), (Ib), (Ic), or (Id), or a pharmaceutically acceptable salt, solvate, isomer, ester, acid, metabolite or prodrug thereof, as well as the pharmaceutical composition comprising the same, hereinafter are referred to as "the substance of the present invention".

The substance of the present invention may be used for treating or preventing conditions associated with FLT3 and/or PDGFR, in particular if the conditions respond to an inhibition of a protein tyrosine kinase, especially to an inhibition of wild-type FLT3 kinase or mutant FLT3/ITD kinase. The "treatment" in the present invention may be therapeutic (e.g., symptomatic treatment) and/or prophylactic. The substance of the present invention may preferably be used for treating or preventing conditions associated with wild-type FLT3, mutant FLT3/ITD, PDGFRα and/or PDGFRl, and particularly for treating or preventing conditions associated with mutant FLT3/ITD, including cell proliferative conditions.

In particular, the substance of the present invention may be used for treating or preventing cell proliferative conditions, such as benign or malignant tumors, including but not limited to: initiation or progression of solid tumor, B-cell lymphoma, sarcoma, lymphoma, diffuse large B-cell lymphoma (DLBCL), follicular lymphoma, chronic lymphocytic lymphoma, anaplastic large-cell lymphoma (ALCL), acute myeloid leukemia, acute lymphocytic leukemia (ALL), acute granulocytic leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), B-cell prolymphocytic leukemia, lymphoplasmacytic lymphoma/Waldenström macroglobulinemia, adult T-cell acute lymphocytic leukemia, AML with trilineage myelodysplasia (AML/TMDS), mixed lineage leukemia (MLL), splenic marginal zone lymphoma, plasma cell myeloma, plasmacytoma, extranodal marginal zone B-cell lymphoma, nodal marginal zone B-cell lymphoma, mantle cell lymphoma, mediastinal (thymic) large B-cell lymphoma, intravascular large B-cell lymphoma, primary effusion lymphoma, Burkitt lymphoma, leukemias, lymphomatoid granulomatosis, breast ductal carcinoma, lobular carcinoma, adenocarcinoma, melanoma, B-cell proliferative disease, brain cancer, kidney cancer, liver cancer, adrenal gland cancer, bladder cancer, breast cancer, lymphoma, stomach cancer, stomach neoplasm, esophagus cancer, ovarian cancer, colorectal cancer, prostate cancer, pancreas cancer, lung cancer, vagina cancer, membranous adenocarcinoma, thyroid cancer, neck cancer, Central Nervous System (CNS) Cancer, malignant glioma, myeloproliferative disorders (MPD), myelodysplasia syndromes (MDS), glioblastoma, multiple myeloma (MM) and myeloid sarcoma, gastrointestinal cancer, head and neck neoplasms, brain tumor, epidermal hyperplasia, psoriasis, prostate hyperplasia, neoplasia, neoplasia of epithelial character, Hodgkin's disease (also called Hodgkin's lymphoma), lymphomas (non-Hodgkin's lymphoma), or similar diseases, or a combination thereof.

The substance of the present invention may also be used for treating or preventing conditions associated with wild-type FLT3, mutant FLT3/ITD, PDGFRα and/or PDGFRβ, particularly for conditions associated with mutant FLT3/ITD, especially acute myeloid leukemia.

Compositions for enteral administration, such as nasal, buccal, rectal or, especially, oral administration, and for parenteral administration, such as intravenous, intramuscular or subcutaneous administration, to warm-blooded animals, especially humans, are especially preferred. The dosage of the active ingredient depends upon the disease to be treated and upon the species, its age, weight, and individual condition, the individual pharmacokinetic data, and the mode of administration.

The pharmaceutical compositions of the invention may optionally be used in combination with known therapeutic processes, for example the administration of hormones or radiation. Such other therapeutic agents include, for example, cytostatic agents, other antiproliferative agents.

Antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, steroids, antiproliferative antibodies, 17-(allylamino)-17-demethoxygeldanamycin (17-AAG) and temozolomide (TMEMODAL).

The term "aromatase inhibitors" as used herein relates to compounds which inhibit the estrogen production, i. e. the conversion of the substrates androstenedione and testosterone. The term includes, but is not limited to steroids, especially exemestane and formestane, and particularly non-steroids, especially aminoglutethimide, vorozole, fadrozole, anastrozole, particularly especially letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Aminoglutethimide can be administered, e.g., in the form as it is marketed, e.g. under the trademark ORIMETEN™.

The composition of the invention, when comprising an aromatase inhibitor as an antitumor agent, is particularly useful in treating hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516, or it can be administered, e.g., in the form as it is marketed, e.g. under the trademark FASLODEX™.

The term "topoisomerase I inhibitors" as used herein includes, but is not limited to topotecan, irinotecan, 9-nitro-camptothecin conjugate PNU-166148 (Compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™) epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing agents including, but not limited to the taxanes paclitaxel and docetaxel, the *vinca* alkaloids, e.g., vinblastine, especially vinblastine sulfate, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity. This includes compounds disclosed in WO 02/22577, especially N-hydroxy-3-[[(2-hydroxyethyl)[2-(1H-indol-3-yl)ethyl]-amino]methyl]phenyl]-2E-2-propenamide, N-hydroxy-3-[[(2-hydroxyethyl)[2-(1H-indol-3-yl)ethyl]-amino]methyl]phenyl]-2E-2-propenamide and pharmaceutically acceptable salts thereof. It further especially includes Suberoylanilide hydroxamic acid (SAHA).

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enzyme (COX-2) and which possess antiproliferative activity, e.g., celecoxib (Celebrex), rofecoxib (Vioxx) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD1694 (RALTITREXED™), LY231514 (ALIMTA™), LY264618 (LOMOTREXOL™) and OGT719.

The term "platin compounds" as used herein includes, but is not limited to carboplatin, cis-platin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl, c-Kit, FLT3, Insulin-like Growth Factor I Receptor (IGF-IR) and Cyclin-dependent kinases (CDKs), and anti-angiogenic compounds having another mechanism of action than decreasing the protein kinase activity.

Compounds which decrease the activity of VEGF comprise those which inhibit VEGF receptor, especially the tyrosine kinase activity of the VEGF receptor, and compounds binding to VEGF, and are in particular those compounds, proteins and monoclonal antibodies generically and specifically disclosed in WO98/35958 (describing compounds of formula I), WO00/09495, WO00/27820, WO00/59509, WO98/11223, WO00/27819, WO01/55114, WO01/58899 and EP0769947; those as described by M. Prewett et al. in Cancer Research 59 (1999) 5209-5218, by Z. Zhu et al. in Cancer Res. 58, 1998, 3209-3214, and by J. Mordenti et al in Toxicologic Pathology, vol. 27, no. 1, pp 14-21, 1999; in WO00/37502 and WO94/10202; Angiostatin™, described by M. S. O'Reilly et al., Cell 79, 1994, 315-328.

Compounds which decrease the activity of EGF are especially compounds which inhibit the binding to EGF, and are in particular those compounds generically and specifically disclosed in WO 97/02266 (describing compounds of formula IV), EP 0564409, WO 99/03854, EP 0520722, EP 0566226, EP 0787722, EP 0837063, WO 98/10767, WO 97/30034, WO 97/49688, WO 97/38983 and, especially, WO 96/33980.

Compounds which decrease the activity of c-Src include, but are not limited to, compounds inhibiting the c-Src protein tyrosine kinase activity as defined below and to SH2 interaction inhibitors such as those disclosed in WO97/07131 and WO97/08193.

Compounds inhibiting the c-Src protein tyrosine kinase activity include, but are not limited to, compounds belonging to the structure classes of pyrrolopyrimidines, especially pyrrolo[2,3-d]pyrimidines; purines; pyrazolopyrimidines, especially pyrrolo[3,4-d]pyrimidines; pyrazolopyrimidines, especially pyrazolo pyrrolo[3,4-d]pyrimidines, and pyridopyrimidines, especially pyrido[2,3-d]pyrimidines. Preferably, the term relates to those compounds disclosed in WO 96/10028, WO 97/28161, WO97/32879 and WO97/49706.

Compounds which decrease the activity of IGF-IR are especially those disclosed in WO02/92599.

Further specific compounds that decrease protein kinase activity and which may also be used in combination with the compounds of the present invention are Imatinib (Gleevec/Glivec), PKC412, Iressa™ (ZD1839), AEE788 and a pharmaceutically acceptable salt thereof (see also WO03/13541), PTK787 and a pharmaceutically acceptable salt thereof (see also WO98/35958), ZD6474, GW2016, CHIR-200131, CEP-7055/CEP-5214, CP-547632, KRN-633 and SU5416.

Anti-angiogenic compounds having another mechanism of action than decreasing the protein kinase activity include, but are not limited to e.g. thalidomide (THALOMID), celecoxib (Celebrex), and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, e.g., as disclosed in U.S. Pat. No. 5,843,901.

The term "anti-androgens" as used herein includes, but is not limited to bicalutamide (CASODEX™), which can be formulated, e.g., as disclosed in U.S. Pat. No. 4,636,505.

The term "bengamides" relates to bengamides and derivatives thereof having antiproliferative properties.

The term "bisphosphonates" as used herein includes, but is not limited to etidronic acid, pamidronic acid, and alendronic acid. Etidronic acid can be administered, e.g., in the form as it is marketed, e.g. under the trademark DIDRINEL™. Clodronic acid can be administered, e.g., in the form as it is marketed, e.g. under the trademark BONEFOS™. Tiludronic acid can be administered, e.g., in the form as it is marketed, e.g. under the trademark SKELID™. Pamidronic acid can be administered, e.g., in the form as it is marketed, e.g. under the trademark AREDIA™. Alendronic acid can be administered, e.g., in the form as it is marketed, e.g. under the trademark FOSAMAX™. Ibandronic acid can be administered, e.g., in the form as it is marketed, e.g. under the trademark BONDRANAT™. Risedronic acid can be administered, e.g., in the form as it is marketed, e.g. under the trademark ACTONEL™. Zoledronic acid can be administered, e.g., in the form as it is marketed, e.g. under the trademark ZOMETA™.

The term "steroids" includes hydrocortisone, decadron, methylprednisolone and ponisone.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan), PRO64553 (anti-CD40) and 2C4 Antibody.

For the treatment of AML, compounds of formula (I) can be used in combination with standard leukemia therapies, especially in combination with therapies used for the treatment of AML. In particular, compounds of formula (I) can be administered in combination with e.g. farnesyltransferase inhibitors and/or other drugs used for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of formula (I) can be prepared and administered as described in the art such as in the documents cited above.

In the embodiments of the invention, when a patient is treated in accordance with the invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Preparation of the Compounds

Compounds of formula (I) may be synthesized using standard synthetic techniques known to those of skill in the art or using methods known in the art in combination with methods described herein. In additions, solvents, temperatures and other reaction conditions presented herein may vary according to those of skill in the art.

In certain embodiments, provided herein are methods of making and methods of using kinase inhibitor compounds described herein. In certain embodiments, compounds described herein can be synthesized using the following synthetic schemes. Compounds may be synthesized using methodologies analogous to those described below by the use of appropriate alternative starting materials.

The starting materials used for the synthesis of the compounds described herein may be synthesized or can be obtained from commercial sources. The compounds described herein and other related compounds having different substituents can be synthesized using techniques and materials known to those of skill in the art. Reactions for the preparation of compounds as disclosed herein may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

Using the synthetic methods described herein, compounds as disclosed herein are obtained in good yields and purity. The compounds prepared by the methods disclosed herein are purified by conventional means known in the art, such as, filtration, recrystallization, chromatography, distillation, and combinations thereof.

Sites on the aromatic ring portion of compounds of Formula (I) can be susceptible to various metabolic reactions, therefore incorporation of appropriate substituents on the aromatic ring structures, such as, by way of example only, halogens can reduce, minimize or eliminate this metabolic pathway.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent.

Compounds of the respective examples are listed in Table 1.

TABLE 1

Structures of the Example Compounds

| Example Nos. | Structural formula |
|---|---|
| 1 | 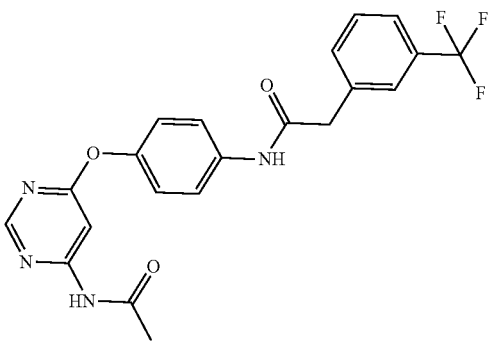 [SMILES: CC(=O)Nc1cc(Oc2ccc(NC(=O)Cc3cccc(C(F)(F)F)c3)cc2)ncn1] |

TABLE 1-continued
Structures of the Example Compounds
| Example Nos. | Structural formula |
|---|---|
| 2 | 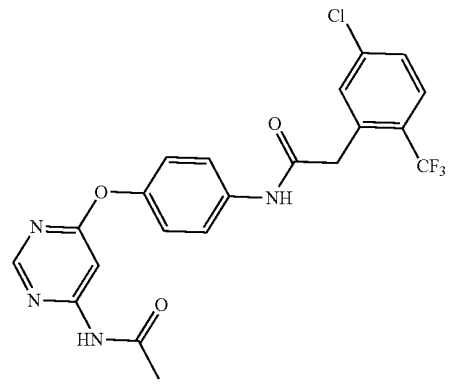 [SMILES: CC(=O)Nc1cc(Oc2ccc(NC(=O)Cc3cc(Cl)ccc3C(F)(F)F)cc2)ncn1] |
| 3 | 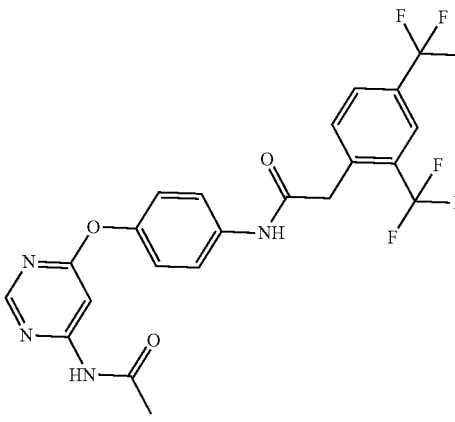 |
| 4 | 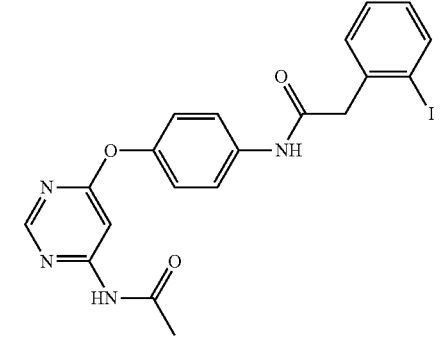 [SMILES: CC(=O)Nc1cc(Oc2ccc(NC(=O)Cc3ccccc3I)cc2)ncn1] |
| 5 | 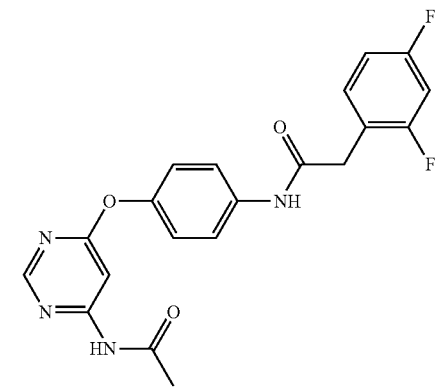 [SMILES: CC(=O)Nc1cc(Oc2ccc(NC(=O)Cc3ccc(F)cc3F)cc2)ncn1] |

TABLE 1-continued

Structures of the Example Compounds

| Example Nos. | Structural formula |
| --- | --- |
| 6 | *structure: 6-acetamido-pyrimidin-4-yloxy-phenyl-NH-C(O)-CH2-(2,6-dichlorophenyl)* |
| 7 | *structure: 6-acetamido-pyrimidin-4-yloxy-phenyl-NH-C(O)-CH2-(2,5-dimethylphenyl)* |
| 8 | *structure: 6-acetamido-pyrimidin-4-yloxy-phenyl-NH-C(O)-CH2-(2,4-dichlorophenyl)* |
| 9 | *structure: 6-acetamido-pyrimidin-4-yloxy-phenyl-NH-C(O)-CH2-(2-methyl-3-nitrophenyl)* |

TABLE 1-continued

Structures of the Example Compounds

| Example Nos. | Structural formula |
|---|---|
| 10 | |
| 11 | |
| 12 | |
| 13 | |

TABLE 1-continued
Structures of the Example Compounds
| Example Nos. | Structural formula |
|---|---|
| 14 | 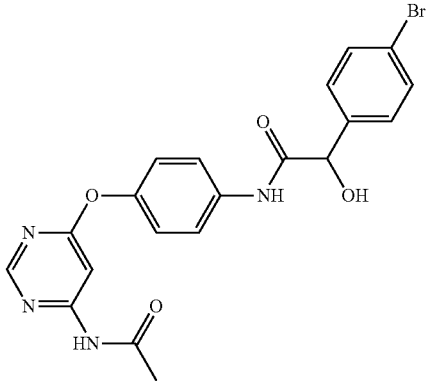 [SMILES: CC(=O)Nc1cc(Oc2ccc(NC(=O)C(O)c3ccc(Br)cc3)cc2)ncn1] |
| 15 | 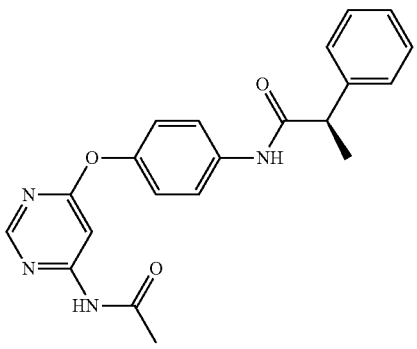 [SMILES: CC(=O)Nc1cc(Oc2ccc(NC(=O)[C@H](C)c3ccccc3)cc2)ncn1] |
| 16 | 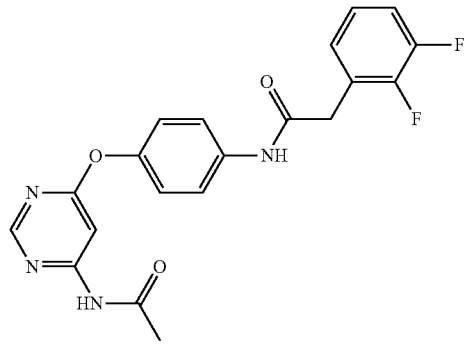 [SMILES: CC(=O)Nc1cc(Oc2ccc(NC(=O)Cc3cccc(F)c3F)cc2)ncn1] |
| 17 | 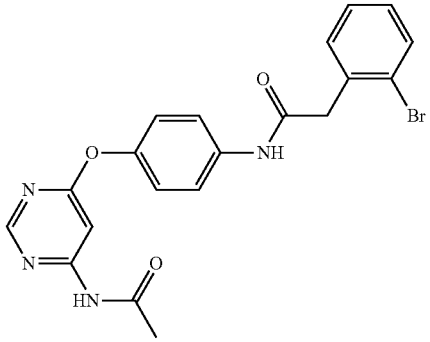 [SMILES: CC(=O)Nc1cc(Oc2ccc(NC(=O)Cc3ccccc3Br)cc2)ncn1] |

TABLE 1-continued
Structures of the Example Compounds
| Example Nos. | Structural formula |
|---|---|
| 18 | 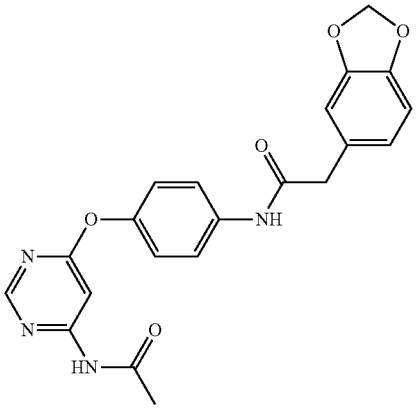 [SMILES: CC(=O)Nc1cc(Oc2ccc(NC(=O)Cc3ccc4c(c3)OCO4)cc2)ncn1] |
| 19 | 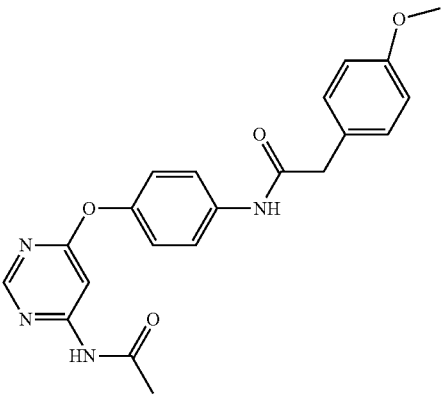 [SMILES: COc1ccc(CC(=O)Nc2ccc(Oc3cc(NC(C)=O)ncn3)cc2)cc1] |
| 20 | 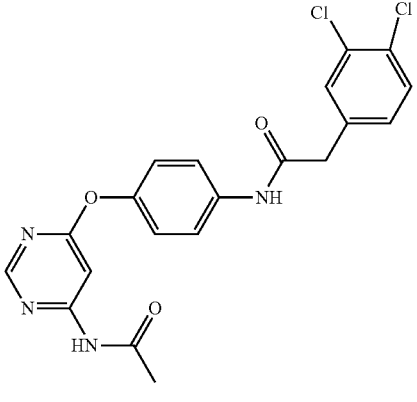 [SMILES: CC(=O)Nc1cc(Oc2ccc(NC(=O)Cc3ccc(Cl)c(Cl)c3)cc2)ncn1] |
| 21 | 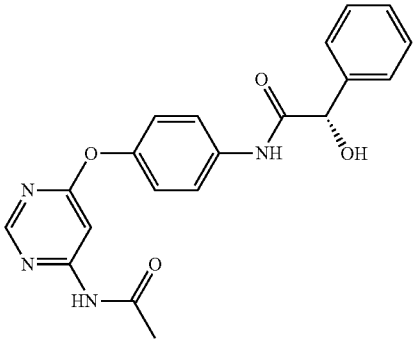 [SMILES: CC(=O)Nc1cc(Oc2ccc(NC(=O)[C@@H](O)c3ccccc3)cc2)ncn1] |

TABLE 1-continued

Structures of the Example Compounds

| Example Nos. | Structural formula |
|---|---|
| 22 | |
| 23 | |
| 24 | |
| 25 | |

TABLE 1-continued

Structures of the Example Compounds

| Example Nos. | Structural formula |
|---|---|
| 26 | (structure) |
| 27 | (structure) |
| 28 | (structure) |
| 29 | (structure) |

TABLE 1-continued

Structures of the Example Compounds

| Example Nos. | Structural formula |
|---|---|
| 30 | |
| 31 | |
| 32 | |
| 33 | |

TABLE 1-continued

Structures of the Example Compounds

| Example Nos. | Structural formula |
|---|---|
| 34 | |
| 35 | |
| 36 | |
| 37 | |
| 38 | |

TABLE 1-continued

Structures of the Example Compounds

| Example Nos. | Structural formula |
|---|---|
| 39 | |
| 40 | |
| 41 | |
| 42 | |

TABLE 1-continued

Structures of the Example Compounds

| Example Nos. | Structural formula |
|---|---|
| 43 | *trans*-cyclohexyl with pyrimidine-O (alpha) linkage; pyrimidine 6-NH-CH₂CH₂-OCH₃; cyclohexyl-NH-C(O)-NH-(4-methyl-3-trifluoromethylphenyl) |
| 44 | *trans*-cyclohexyl with pyrimidine-O linkage; pyrimidine 6-NH-CH₂CH₂-OH; cyclohexyl-NH-C(O)-NH-(4-methyl-3-trifluoromethylphenyl) |
| 45 | *trans*-cyclohexyl with pyrimidine-O linkage; pyrimidine 6-NH-CH₂CH₂-OCH₃; cyclohexyl-NH-C(O)-NH-(4-methyl-3-trifluoromethylphenyl) |
| 46 | *trans*-cyclohexyl with pyrimidine-O (alpha) linkage; pyrimidine 6-NH-CH₂CH₂-NH₂; cyclohexyl-NH-C(O)-NH-(4-methyl-3-trifluoromethylphenyl) |

TABLE 1-continued

Structures of the Example Compounds

| Example Nos. | Structural formula |
|---|---|
| 47 | *(structure)* |
| 48 | *(structure)* |
| 49 | *(structure)* |
| 50 | *(structure)* |

TABLE 1-continued

Structures of the Example Compounds

| Example Nos. | Structural formula |
|---|---|
| 51 | |
| 52 | |
| 53 | |

TABLE 1-continued

Structures of the Example Compounds

| Example Nos. | Structural formula |
|---|---|
| 54 | |
| 55 | |
| 56 | |
| 57 | |

TABLE 1-continued
Structures of the Example Compounds
| Example Nos. | Structural formula |
|---|---|
| 58 | 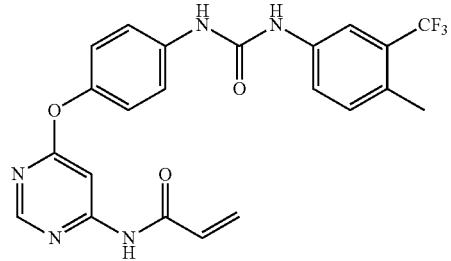 [SMILES: C=CC(=O)Nc1cc(Oc2ccc(NC(=O)Nc3ccc(C)c(C(F)(F)F)c3)cc2)ncn1] |
| 59 | 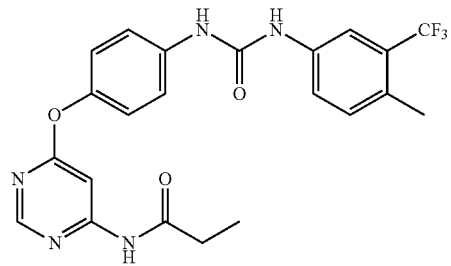 [SMILES: CCC(=O)Nc1cc(Oc2ccc(NC(=O)Nc3ccc(C)c(C(F)(F)F)c3)cc2)ncn1] |
| 60 | 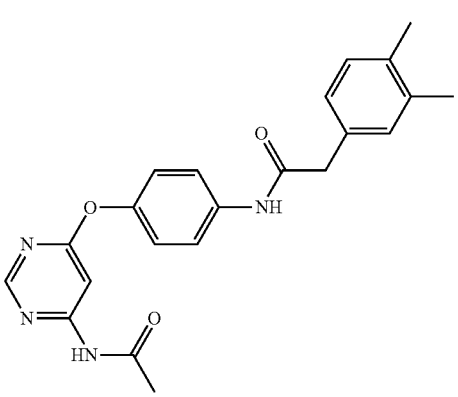 [SMILES: CC(=O)Nc1cc(Oc2ccc(NC(=O)Cc3ccc(C)c(C)c3)cc2)ncn1] |
| 61 | 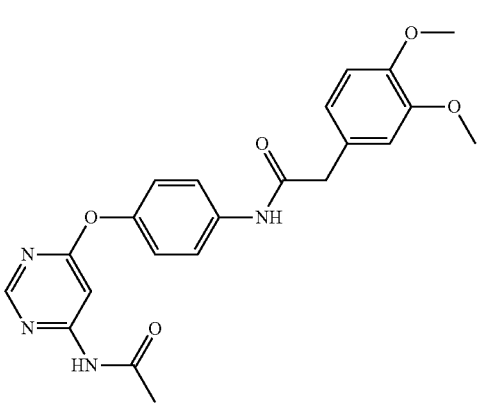 [SMILES: COc1ccc(CC(=O)Nc2ccc(Oc3cc(NC(C)=O)ncn3)cc2)cc1OC] |

TABLE 1-continued

Structures of the Example Compounds

| Example Nos. | Structural formula |
|---|---|
| 62 | (structure: 4-(6-acetamidopyrimidin-4-yloxy)phenyl amide of 2-(3,4,5-trimethoxyphenyl)acetic acid) |
| 63 | (structure: 4-(6-acetamidopyrimidin-4-yloxy)phenyl amide of 2-(2-fluorophenyl)-2-hydroxyacetic acid) |
| 64 | (structure: 4-(6-acetamidopyrimidin-4-yloxy)phenyl amide of 2-(3-fluoro-4-hydroxyphenyl)acetic acid) |
| 65 | (structure: 4-(6-acetamidopyrimidin-4-yloxy)phenyl amide of 2-(4-tert-butylphenyl)acetic acid) |

TABLE 1-continued

Structures of the Example Compounds

| Example Nos. | Structural formula |
| --- | --- |
| 66 | *N-(6-((4-(2-(2,6-difluorophenyl)acetamido)phenoxy)pyrimidin-4-yl)acetamide structure* |
| 67 | *N-(6-((4-(2-(2-(trifluoromethyl)phenyl)acetamido)phenyl)thio)pyrimidin-4-yl)acetamide structure* |
| 68 | *N-(6-((4-(2-(3-(trifluoromethyl)phenyl)acetamido)phenyl)thio)pyrimidin-4-yl)acetamide structure* |
| 69 | *N-(6-((4-(2-(4-(trifluoromethyl)phenyl)acetamido)phenyl)thio)pyrimidin-4-yl)acetamide structure* |

TABLE 1-continued
Structures of the Example Compounds
| Example Nos. | Structural formula |
| --- | --- |
| 70 | 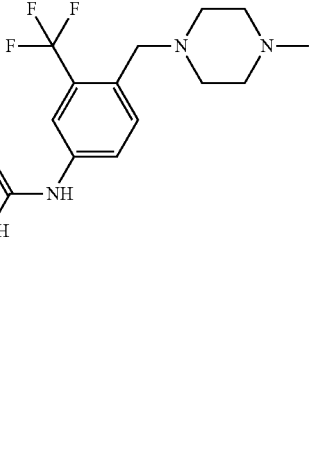 |
| 71 | 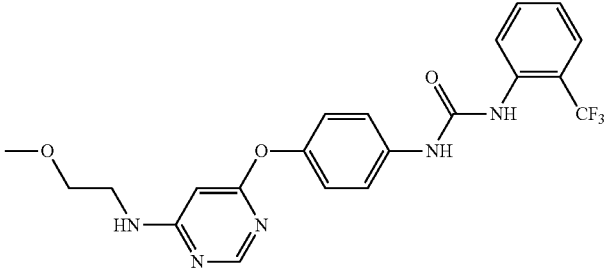 [SMILES: COCCNc1cc(Oc2ccc(NC(=O)Nc3ccccc3C(F)(F)F)cc2)ncn1] |
| 72 | 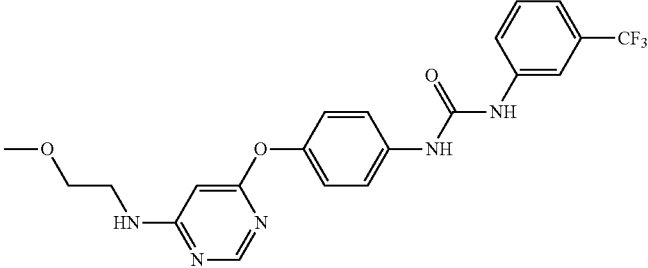 [SMILES: COCCNc1cc(Oc2ccc(NC(=O)Nc3cccc(C(F)(F)F)c3)cc2)ncn1] |
| 73 | 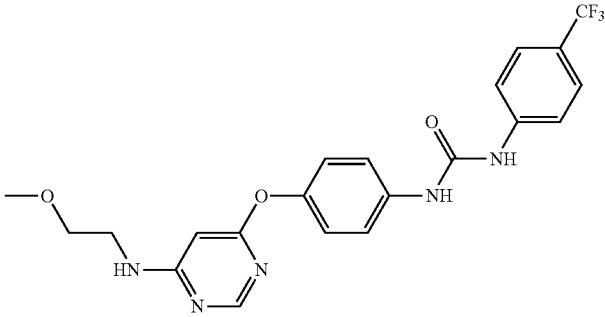 [SMILES: COCCNc1cc(Oc2ccc(NC(=O)Nc3ccc(C(F)(F)F)cc3)cc2)ncn1] |

TABLE 1-continued

Structures of the Example Compounds

| Example Nos. | Structural formula |
|---|---|
| 74 | *(structure)* |
| 75 | *(structure)* |
| 76 | *(structure)* |
| 77 | *(structure)* |

TABLE 1-continued
Structures of the Example Compounds
| Example Nos. | Structural formula |
|---|---|
| 78 | 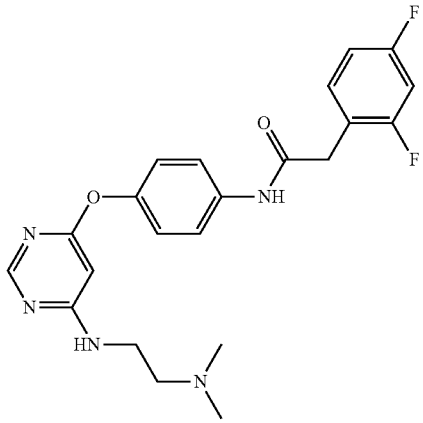 [SMILES: CN(C)CCNc1cc(Oc2ccc(NC(=O)Cc3ccc(F)cc3F)cc2)ncn1] |
| 79 | 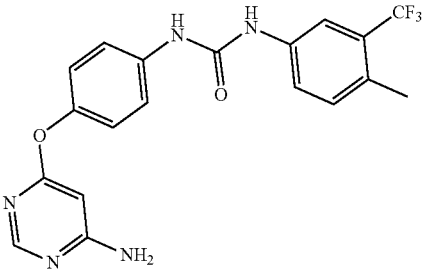 [SMILES: Cc1ccc(NC(=O)Nc2ccc(Oc3cc(N)ncn3)cc2)cc1C(F)(F)F] |
| 80 | 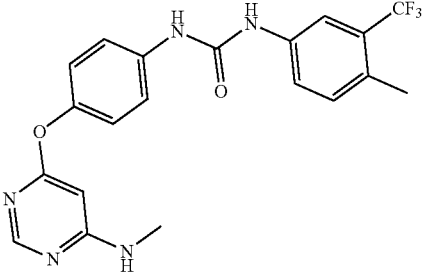 [SMILES: CNc1cc(Oc2ccc(NC(=O)Nc3ccc(C)c(C(F)(F)F)c3)cc2)ncn1] |
| 81 | 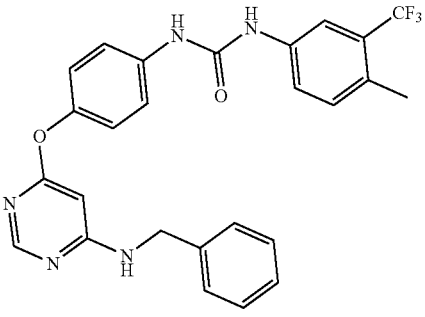 [SMILES: Cc1ccc(NC(=O)Nc2ccc(Oc3cc(NCc4ccccc4)ncn3)cc2)cc1C(F)(F)F] |

TABLE 1-continued

Structures of the Example Compounds

| Example Nos. | Structural formula |
|---|---|
| 82 | |
| 83 | |
| 84 | |
| 85 | |
| 86 | |

TABLE 1-continued

Structures of the Example Compounds

| Example Nos. | Structural formula |
|---|---|
| 87 | |
| 88 | |
| 89 | |
| 90 | |
| 91 | |

TABLE 1-continued

Structures of the Example Compounds

| Example Nos. | Structural formula |
|---|---|
| 92 | |
| 93 | |
| 94 | |
| 95 | |
| 96 | |

TABLE 1-continued
Structures of the Example Compounds
| Example Nos. | Structural formula |
|---|---|
| 97 | 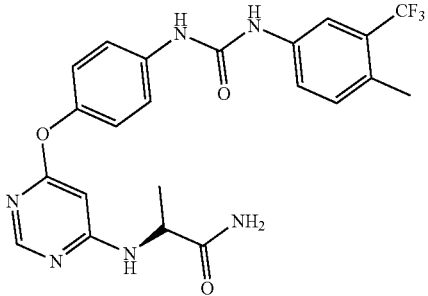 |
| 98 | 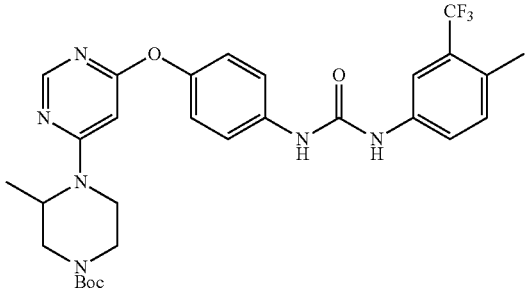 |
| 99 | 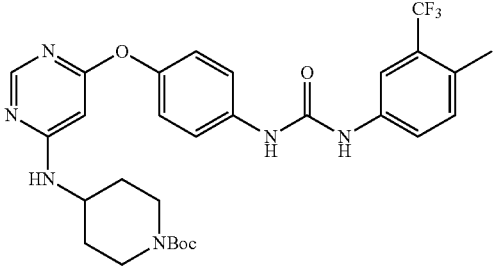 |
| 100 | 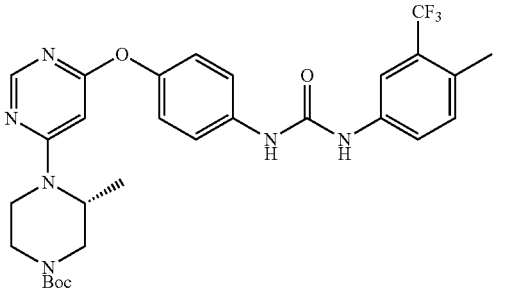 [SMILES: Cc1ccc(NC(=O)Nc2ccc(Oc3cc(N4CCN(C(=O)OC(C)(C)C)C[C@H]4C)ncn3)cc2)cc1C(F)(F)F] |
| 101 | 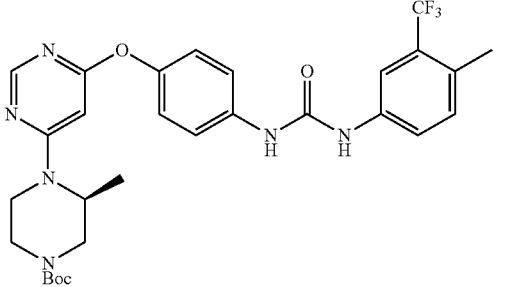 |

TABLE 1-continued

Structures of the Example Compounds

| Example Nos. | Structural formula |
|---|---|
| 102 | (structure: pyrimidine-O-phenyl-NHC(O)NH-phenyl(CF₃)(CH₃); pyrimidine substituted with N-Boc-3-methylpiperazine) |
| 103 | (structure: pyrimidine-O-phenyl-NHC(O)NH-phenyl(CF₃)(CH₃); pyrimidine substituted with 4-aminopiperidine (HN-piperidine)) |
| 104 | (structure: pyrimidine-O-phenyl-NHC(O)NH-phenyl(CF₃)(CH₃); pyrimidine substituted with 2-methylpiperazine) |
| 105 | (structure: pyrimidine-O-phenyl-NHC(O)NH-phenyl(CF₃)(CH₃); pyrimidine substituted with (S)-2-methylpiperazine) |
| 106 | (structure: pyrimidine-O-phenyl-NHC(O)NH-phenyl(CF₃)(CH₃); pyrimidine substituted with 3-methylpiperazine) |

TABLE 1-continued

Structures of the Example Compounds

| Example Nos. | Structural formula |
|---|---|
| 107 | (structure) |
| 108 | (structure) |
| 109 | (structure) |
| 110 | (structure) |
| 111 | (structure) |

TABLE 1-continued

Structures of the Example Compounds

| Example Nos. | Structural formula |
|---|---|
| 112 | (structure) |
| 113 | (structure) |
| 114 | (structure) |
| 115 | (structure) |

TABLE 1-continued
Structures of the Example Compounds
| Example Nos. | Structural formula |
|---|---|
| 116 | 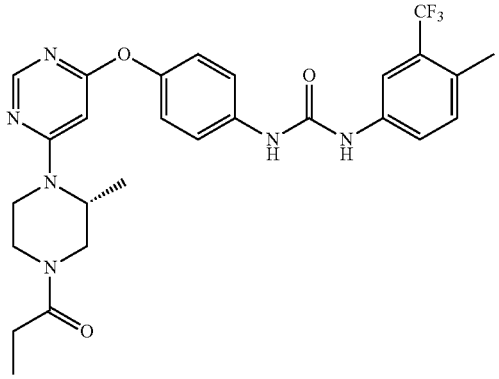 [SMILES: CCC(=O)N1CCN(c2cc(Oc3ccc(NC(=O)Nc4ccc(C)c(C(F)(F)F)c4)cc3)ncn2)[C@H](C)C1] |
| 117 | 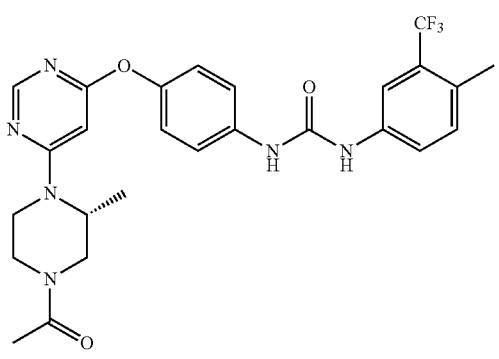 [SMILES: CC(=O)N1CCN(c2cc(Oc3ccc(NC(=O)Nc4ccc(C)c(C(F)(F)F)c4)cc3)ncn2)[C@H](C)C1] |
| 118 | 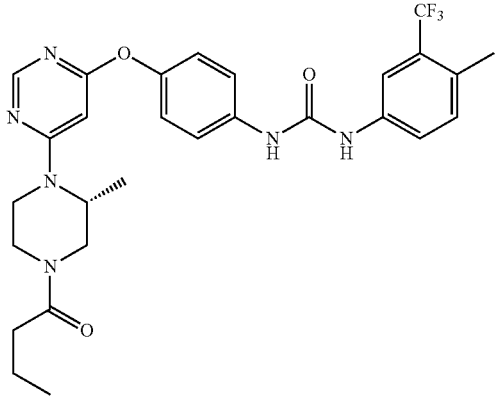 [SMILES: CCCC(=O)N1CCN(c2cc(Oc3ccc(NC(=O)Nc4ccc(C)c(C(F)(F)F)c4)cc3)ncn2)[C@H](C)C1] |
| 119 | 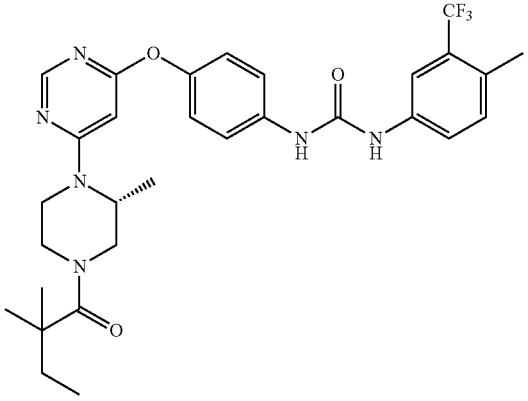 [SMILES: CCC(C)(C)C(=O)N1CCN(c2cc(Oc3ccc(NC(=O)Nc4ccc(C)c(C(F)(F)F)c4)cc3)ncn2)[C@H](C)C1] |

TABLE 1-continued
Structures of the Example Compounds
| Example Nos. | Structural formula |
|---|---|
| 120 | 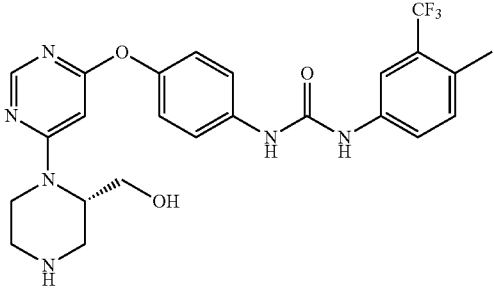 [SMILES: Cc1ccc(NC(=O)Nc2ccc(Oc3cc(N4CCNC[C@H]4CO)ncn3)cc2)cc1C(F)(F)F] |
| 121 | 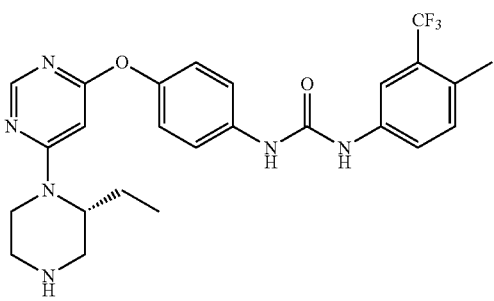 [SMILES: CC[C@@H]1CNCCN1c1cc(Oc2ccc(NC(=O)Nc3ccc(C)c(C(F)(F)F)c3)cc2)ncn1] |
| 122 | 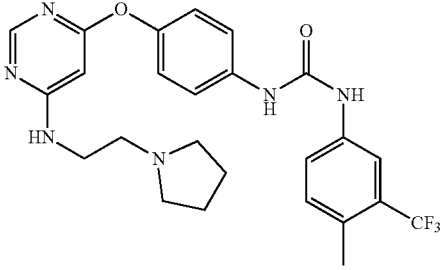 [SMILES: Cc1ccc(NC(=O)Nc2ccc(Oc3cc(NCCN4CCCC4)ncn3)cc2)cc1C(F)(F)F] |
| 123 | 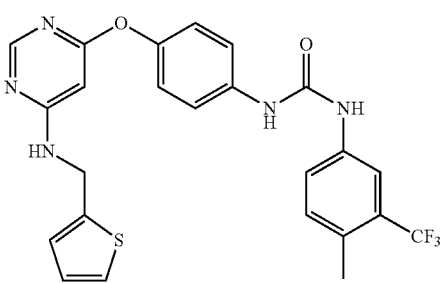 [SMILES: Cc1ccc(NC(=O)Nc2ccc(Oc3cc(NCc4cccs4)ncn3)cc2)cc1C(F)(F)F] |
| 124 | 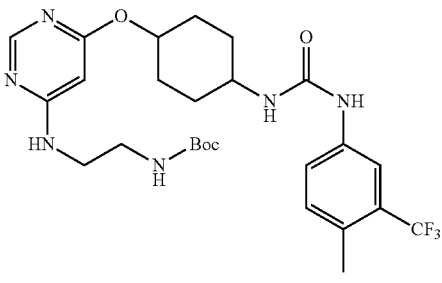 [SMILES: Cc1ccc(NC(=O)NC2CCC(Oc3cc(NCCNC(=O)OC(C)(C)C)ncn3)CC2)cc1C(F)(F)F] |

TABLE 1-continued

Structures of the Example Compounds

| Example Nos. | Structural formula |
| --- | --- |
| 125 | (structure) |
| 126 | (structure) |
| 127 | (structure) |
| 128 | (structure) |
| 129 | (structure) |

TABLE 1-continued

Structures of the Example Compounds

| Example Nos. | Structural formula |
| --- | --- |
| 130 | |
| 131 | |
| 132 | |
| 133 | |

TABLE 1-continued

Structures of the Example Compounds

| Example Nos. | Structural formula |
|---|---|
| 134 | (structure) |
| 135 | (structure) |
| 136 | (structure) |
| 137 | (structure) |
| 138 | (structure) |

TABLE 1-continued
Structures of the Example Compounds
| Example Nos. | Structural formula |
|---|---|
| 139 | 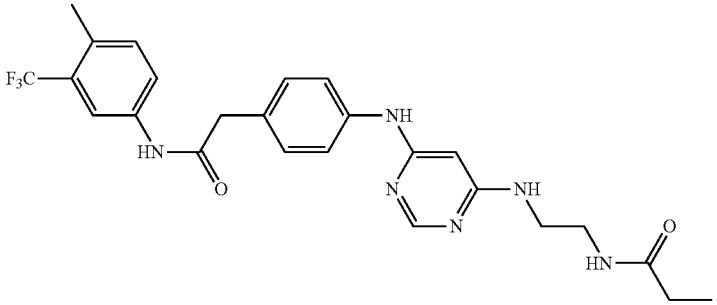 |
| 140 | 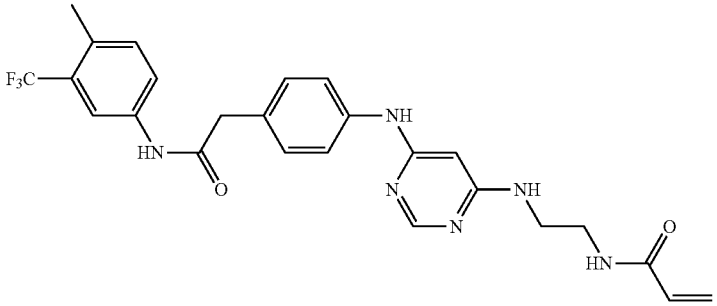 [SMILES: C=CC(=O)NCCNc1cc(Nc2ccc(CC(=O)Nc3ccc(C)c(C(F)(F)F)c3)cc2)ncn1] |
| 141 | 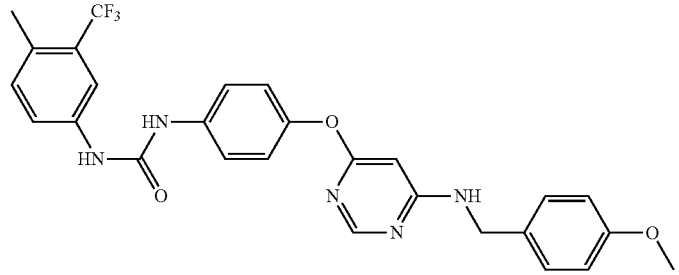 [SMILES: COc1ccc(CNc2cc(Oc3ccc(NC(=O)Nc4ccc(C)c(C(F)(F)F)c4)cc3)ncn2)cc1] |
| 142 | 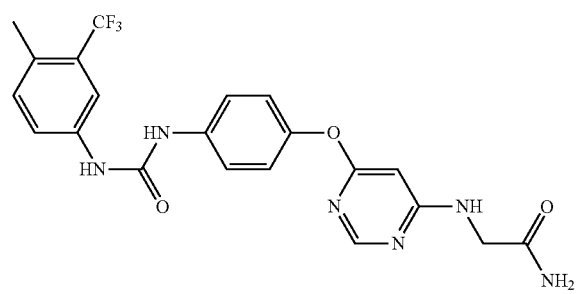 |
| 143 | 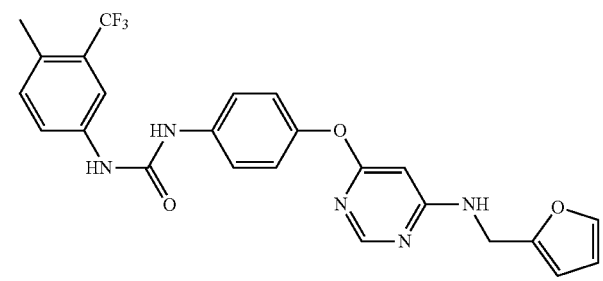 [SMILES: Cc1ccc(NC(=O)Nc2ccc(Oc3cc(NCc4ccco4)ncn3)cc2)cc1C(F)(F)F] |

TABLE 1-continued

Structures of the Example Compounds

| Example Nos. | Structural formula |
|---|---|
| 144 | 4-methyl-3-(trifluoromethyl)phenyl urea linked to phenoxy-pyrimidine with 4-hydroxycyclohexylamino substituent |
| 145 | 4-methyl-3-(trifluoromethyl)phenyl urea linked to phenoxy-pyrimidine with 4-ethylpiperazinyl substituent |
| 146 | 4-methyl-3-(trifluoromethyl)phenyl urea linked to phenoxy-pyrimidine with 4-methylpiperazinyl substituent |
| 147 | 4-methyl-3-(trifluoromethyl)phenyl urea linked to phenoxy-pyrimidine with tetrahydropyran-4-ylamino substituent |
| 148 | 4-methyl-3-(trifluoromethyl)phenyl urea linked to phenoxy-pyrimidine with 4-(2-methoxyethyl)piperazinyl substituent |

TABLE 1-continued
Structures of the Example Compounds
| Example Nos. | Structural formula |
|---|---|
| 149 | 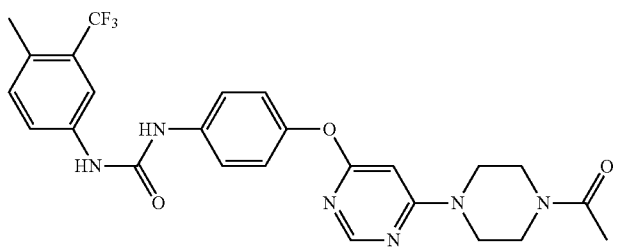 [SMILES: CC(=O)N1CCN(c2cc(Oc3ccc(NC(=O)Nc4ccc(C)c(C(F)(F)F)c4)cc3)ncn2)CC1] |
| 150 | 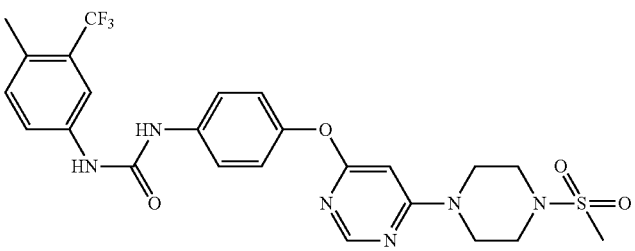 [SMILES: Cc1ccc(NC(=O)Nc2ccc(Oc3cc(N4CCN(S(C)(=O)=O)CC4)ncn3)cc2)cc1C(F)(F)F] |
| 151 | 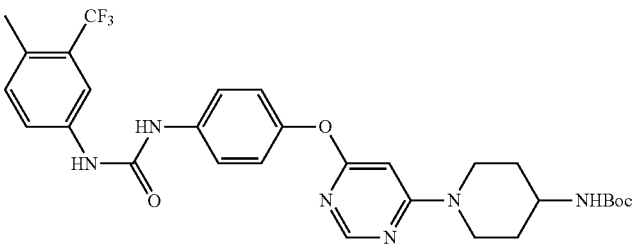 [SMILES: Cc1ccc(NC(=O)Nc2ccc(Oc3cc(N4CCC(NC(=O)OC(C)(C)C)CC4)ncn3)cc2)cc1C(F)(F)F] |
| 152 | 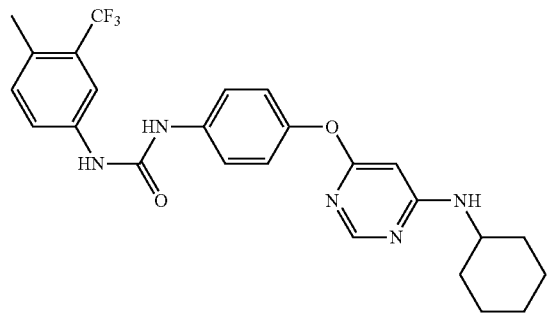 [SMILES: Cc1ccc(NC(=O)Nc2ccc(Oc3cc(NC4CCCCC4)ncn3)cc2)cc1C(F)(F)F] |
| 153 | 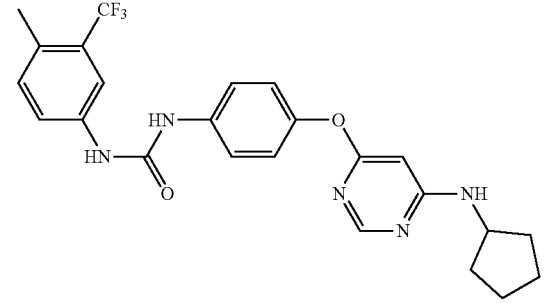 [SMILES: Cc1ccc(NC(=O)Nc2ccc(Oc3cc(NC4CCCC4)ncn3)cc2)cc1C(F)(F)F] |

TABLE 1-continued

Structures of the Example Compounds

| Example Nos. | Structural formula |
|---|---|
| 154 | |
| 155 | |
| 156 | |
| 157 | |
| 158 | |

TABLE 1-continued

Structures of the Example Compounds

| Example Nos. | Structural formula |
|---|---|
| 159 | |
| 160 | |
| 161 | |
| 162 | |

TABLE 1-continued
Structures of the Example Compounds
| Example Nos. | Structural formula |
|---|---|
| 163 | 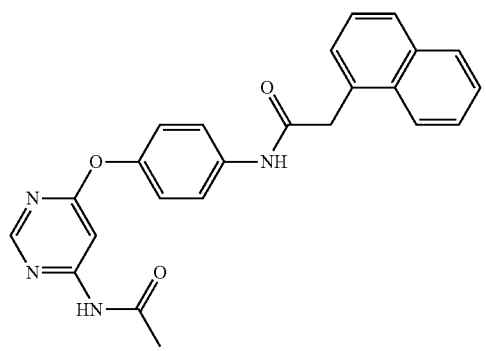 [SMILES: CC(=O)Nc1cc(Oc2ccc(NC(=O)Cc3cccc4ccccc34)cc2)ncn1] |
| 164 | 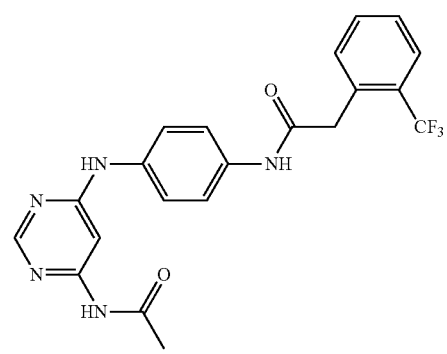 |
| 165 | 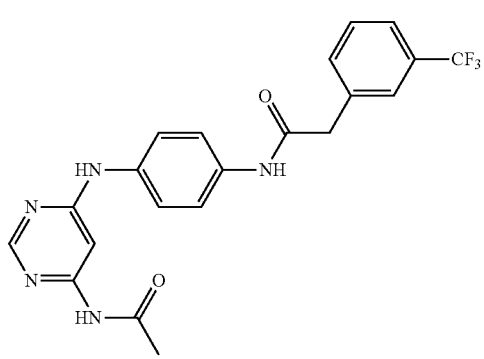 [SMILES: CC(=O)Nc1cc(Nc2ccc(NC(=O)Cc3cccc(C(F)(F)F)c3)cc2)ncn1] |
| 166 | 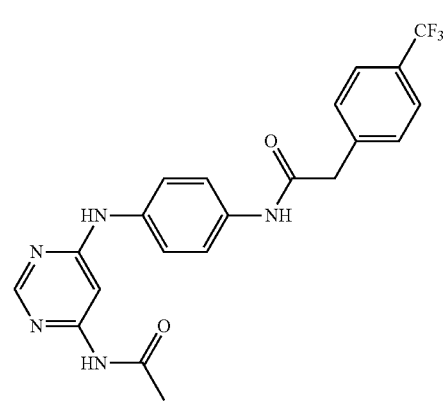 [SMILES: CC(=O)Nc1cc(Nc2ccc(NC(=O)Cc3ccc(C(F)(F)F)cc3)cc2)ncn1] |

TABLE 1-continued

Structures of the Example Compounds

| Example Nos. | Structural formula |
|---|---|
| 167 | |
| 168 | |
| 169 | |
| 170 | |

TABLE 1-continued
Structures of the Example Compounds
| Example Nos. | Structural formula |
|---|---|
| 171 | 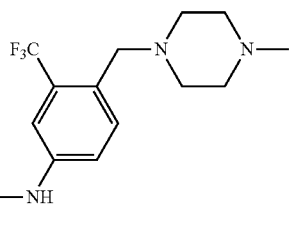 |
| 172 | 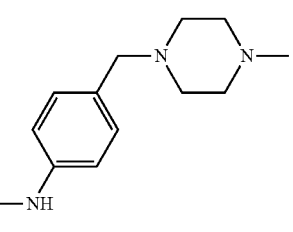 |
| 173 | 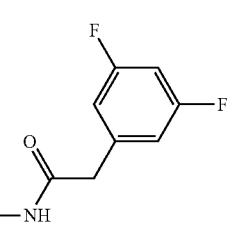 |

TABLE 1-continued

Structures of the Example Compounds

| Example Nos. | Structural formula |
|---|---|
| 174 | (structure) |
| 175 | (structure) |
| 176 | (structure) |
| 177 | (structure) |

TABLE 1-continued
Structures of the Example Compounds
| Example Nos. | Structural formula |
|---|---|
| 178 | 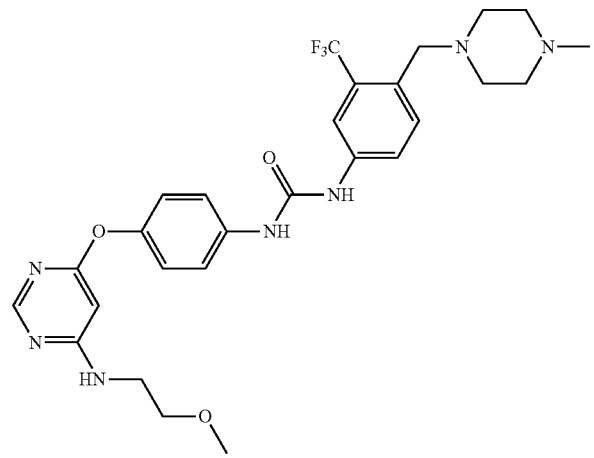 [SMILES: COCCNc1cc(Oc2ccc(NC(=O)Nc3ccc(CN4CCN(C)CC4)c(C(F)(F)F)c3)cc2)ncn1] |
| 179 | 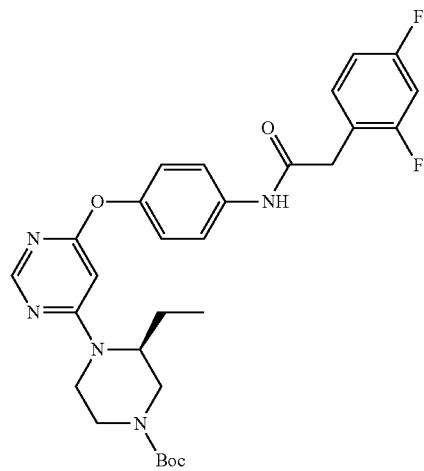 [SMILES: CC[C@H]1CN(C(=O)OC(C)(C)C)CCN1c1cc(Oc2ccc(NC(=O)Cc3ccc(F)cc3F)cc2)ncn1] |
| 180 | 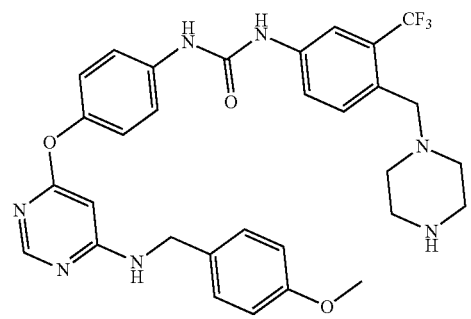 [SMILES: COc1ccc(CNc2cc(Oc3ccc(NC(=O)Nc4ccc(CN5CCNCC5)c(C(F)(F)F)c4)cc3)ncn2)cc1] |

TABLE 1-continued

Structures of the Example Compounds

| Example Nos. | Structural formula |
|---|---|
| 181 | |
| 182 | |
| 183 | |
| 184 | |

TABLE 1-continued

Structures of the Example Compounds

| Example Nos. | Structural formula |
|---|---|
| 185 | *(structure: N-[4-(6-acetylamino-pyrimidin-4-yloxy)-3-methyl-phenyl]-2-(3-trifluoromethyl-phenyl)-acetamide)* |

Example 1: N-[4-(6-acetylamino-pyrimidin-4-yloxy)-phenyl]-2-(3-trifluoromethyl-phenyl)-acetamide

*(reaction scheme showing A1 → A2 → A3 → A4 → final product)*

N-(6-chloro-pyrimidin-4-yl)-acetamide (A2): 6-chloropyrimidin-4-ylamine (5 g) was added into a round-bottom flask, followed by addition of acetic anhydride (20 ml). The reaction system was allowed to react at 140 degrees for 5 hours under the protection of argon. After the reaction was completed, the solvent in the system was evaporated to dryness under reduced pressure, and the resultant was washed with methanol to obtain the compound (A2), LC/MS: M+H 172.03.

[4-(6-acetylamino-pyrimidin-4-yloxy)-phenyl]-aminotert-butyl formate (A3): N-(6-chloropyrimidin-4-yl)-acetamide (500 mg) was added into a round-bottom flask, followed by addition of N,N-dimethylformamide (5 ml), (4-hydroxy-phenyl)-aminotert-butyl formate (1.2 g) and cesium carbonate (2.8 g). The reaction system was allowed to react at 50 degrees for 20 hours under the protection of argon. After the reaction was completed, the solvent in the system was evaporated to dryness under reduced pressure, and the resultant was subjected to dilution with water and then extraction with ethyl acetate. The organic phase was washed respectively with water, saturated saline and then dried with anhydrous sodium sulfate. The organic phase was filtered and evaporated under reduced pressure to dryness to give crude product. The crude was purified by pressurized silica gel column chromatography to give Compound (A3), LC/MS: M+H 345.16.

N-[6-(4-amino-phenoxy)-pyrimidin-4-yl]-acetamide (A4): [4-(6-acetylamino-pyrimidin-4-yloxy)-phenyl]-aminotert-butyl formate (250 mg) was added into a round-bottom flask, followed by addition of a solution of ethyl acetate (8 ml) and methanol (2 ml) in HCl. The reaction system was allowed to react at room temperature for 5 hours. After the reaction was completed, the system was evaporated under reduced pressure to dryness to give Compound (A4), LC/MS: M+H 245.11.

N-[4-(6-acetylamino-pyrimidin-4-yloxy)-phenyl]-2-(3-trifluoromethyl-phenyl)-acetamide: N-[6-(4-amino-phenoxy)-pyrimidin-4-yl]-acetamide (60 mg) was added into a round-bottom flask, followed by addition of tetrahydrofuran (1 ml), (2-(3-(trifluoromethyl)phenyl)acetic acid (45 mg), 2-(7-azobenzotriazole)-N,N,N',N'-tetramethyluronium hexafluorophosphate (HATU) (78 mg) and N,N-diisopropylethylamine (0.2 ml). The reaction system was stirred for 14 hours at room temperature under protection of argon. After the reaction was completed, the solvent in the system was evaporated to dryness under reduced pressure and the resultant was diluted with water and subjected to extraction with ethyl acetate. The organic phase was washed respectively with water and saturated saline and then dried with anhydrous sodium sulfate. The organic phase was filtered and evaporated under reduced pressure to dryness to give crude product. The crude was purified by pressurized silica gel column chromatography to give Example Compound 1, MS(ESI) m/z (M+1)+: 431.14.

Example 2: N-[4-(6-acetylamino-pyrimidin-4-yloxy)-phenyl]-2-(5-chloro-2-trifluoromethyl-phenyl)-acetamide Example 3: N-[4-(6-acetylamino-pyrimidin-4-yloxy)-phenyl]-2-(2,4-bis-trifluoromethyl-phenyl)-acetamide

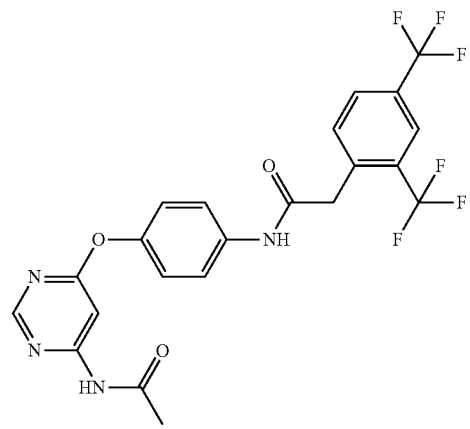

Synthesis of the compound of Example 3 was accomplished by using procedures similar to that described in Example 1. MS(ESI) m/z (M+1)+: 499.12.

Example 4: N-[4-(6-acetylamino-pyrimidin-4-yloxy)-phenyl]-2-(2-iodo-phenyl)-acetamide

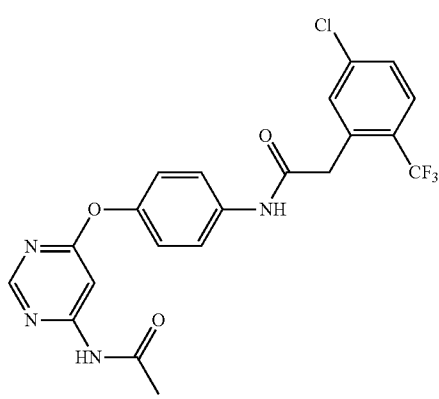 [SMILES: CC(=O)Nc1cc(Oc2ccc(NC(=O)Cc3cc(Cl)ccc3C(F)(F)F)cc2)ncn1]

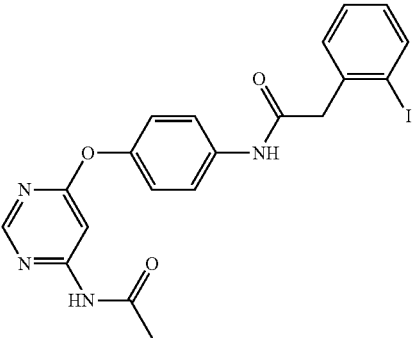 [SMILES: CC(=O)Nc1cc(Oc2ccc(NC(=O)Cc3ccccc3I)cc2)ncn1]

Synthesis of the compound of Example 2 was accomplished by using procedures similar to that described in Example 1. MS(ESI) m/z (M+1)+: 465.10.

Synthesis of the compound of Example 4 was accomplished by using procedures similar to that described in Example 1. MS(ESI) m/z (M+1)+: 489.04.

Example 5: N-[4-(6-acetylamino-pyrimidin-4-yloxy)-phenyl]-2-(2,4-difluoro-phenyl)-acetamide

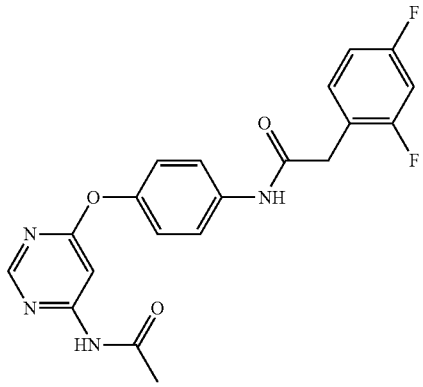 [SMILES: CC(=O)Nc1cc(Oc2ccc(NC(=O)Cc3ccc(F)cc3F)cc2)ncn1]

Synthesis of the compound of Example 5 was accomplished by using procedures similar to that described in Example 1. MS(ESI) m/z (M+1)+: 399.13.

Example 6: N-[4-(6-acetylamino-pyrimidin-4-yloxy)-phenyl]-2-(2,6-dichloro-phenyl)-acetamide

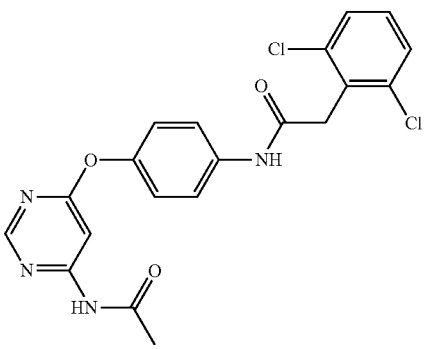 [SMILES: CC(=O)Nc1cc(Oc2ccc(NC(=O)Cc3c(Cl)cccc3Cl)cc2)ncn1]

Synthesis of the compound of Example 6 was accomplished by using procedures similar to that described in Example 1. MS(ESI) m/z (M+1)+: 431.07.

Example 7: N-[4-(6-acetylamino-pyrimidin-4-yloxy)-phenyl]-2-(2,5-dimethyl-phenyl)-acetamide

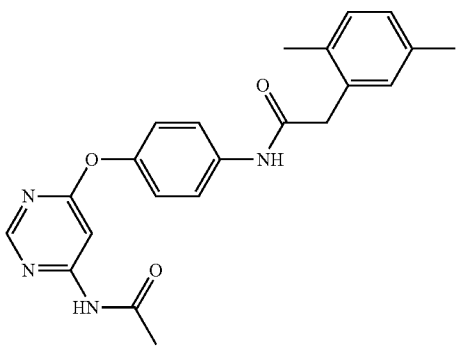 [SMILES: CC(=O)Nc1cc(Oc2ccc(NC(=O)Cc3cc(C)ccc3C)cc2)ncn1]

Synthesis of the compound of Example 7 was accomplished by using procedures similar to that described in Example 1. MS(ESI) m/z (M+1)+: 391.18.

Example 8: N-[4-(6-acetylamino-pyrimidin-4-yloxy)-phenyl]-2-(2,4-dichloro-phenyl)-acetamide

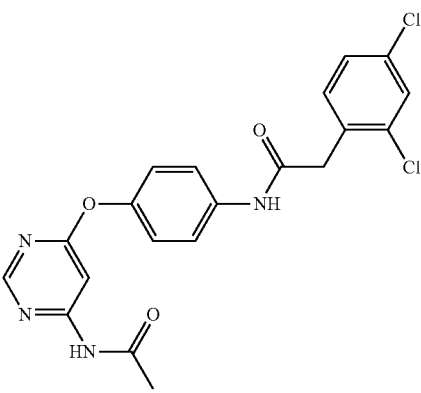 [SMILES: CC(=O)Nc1cc(Oc2ccc(NC(=O)Cc3ccc(Cl)cc3Cl)cc2)ncn1]

Synthesis of the compound of Example 8 was accomplished by using procedures similar to that described in Example 1. MS(ESI) m/z (M+1)+: 431.07.

Example 9: N-[4-(6-acetylamino-pyrimidin-4-yloxy)-phenyl]-2-(2-methyl-3-nitro-phenyl)-acetamide

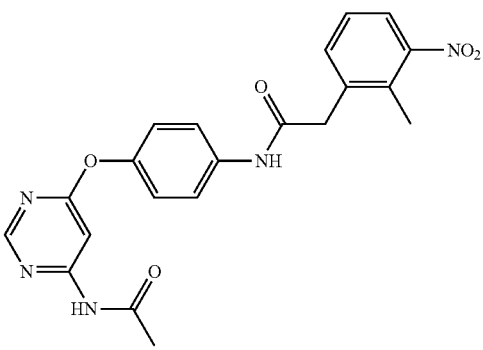 [SMILES: CC(=O)Nc1cc(Oc2ccc(NC(=O)Cc3cccc([N+](=O)[O-])c3C)cc2)ncn1]

Synthesis of the compound of Example 9 was accomplished by using procedures similar to that described in Example 1. MS(ESI) m/z (M+1)+: 422.15.

Example 10: N-[4-(6-acetylamino-pyrimidin-4-yloxy)-phenyl]-2-(2-fluoro-biphenyl-4-yl)-propanamide lp;3p

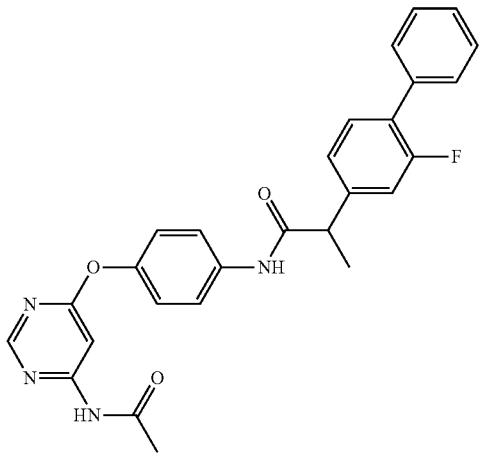 [SMILES: CC(=O)Nc1cc(Oc2ccc(NC(=O)C(C)c3ccc(-c4ccccc4)c(F)c3)cc2)ncn1]

Synthesis of the compound of Example 10 was accomplished by using procedures similar to that described in Example 1. MS(ESI) m/z (M+1)+: 471.19.

Example 11: N-[4-(6-acetylamino-pyrimidin-4-yloxy)-phenyl]-2-(4-hydroxy-3-methoxy-phenyl)-acetamide

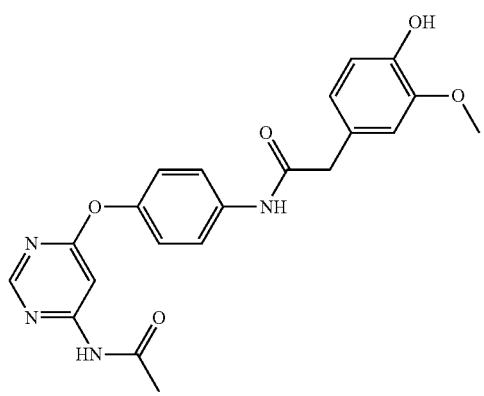 [SMILES: COc1cc(CC(=O)Nc2ccc(Oc3cc(NC(C)=O)ncn3)cc2)ccc1O]

Synthesis of the compound of Example 11 was accomplished by using procedures similar to that described in Example 1. MS(ESI) m/z (M+1)+: 409.15.

Example 12: N-[4-(6-acetylamino-pyrimidin-4-yloxy)-phenyl]-2-(3-phenoxy-phenyl)-acetamide

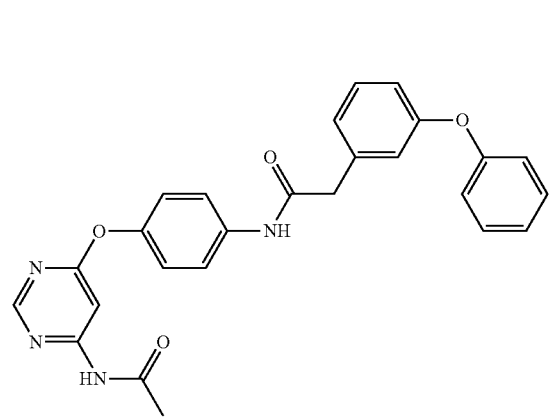 [SMILES: CC(=O)Nc1cc(Oc2ccc(NC(=O)Cc3cccc(Oc4ccccc4)c3)cc2)ncn1]

Synthesis of the compound of Example 12 was accomplished by using procedures similar to that described in Example 1. MS(ESI) m/z (M+1)+: 455.17.

Example 13: N-[4-(6-acetylamino-pyrimidin-4-yloxy)-phenyl]-2-(3-bromo-phenyl)-acetamide

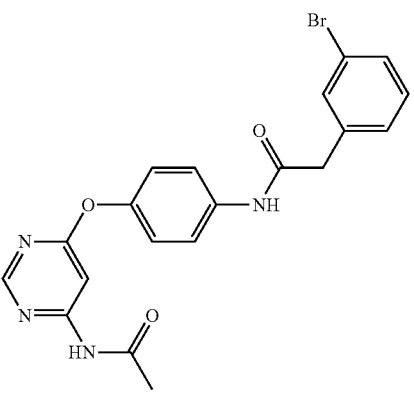 [SMILES: CC(=O)Nc1cc(Oc2ccc(NC(=O)Cc3cccc(Br)c3)cc2)ncn1]

Synthesis of the compound of Example 13 was accomplished by using procedures similar to that described in Example 1. MS(ESI) m/z (M+1)+: 441.06.

Example 14: N-[4-(6-acetylamino-pyrimidin-4-yloxy)-phenyl]-2-(4-bromo-phenyl)-2-hydroxy-acetamide

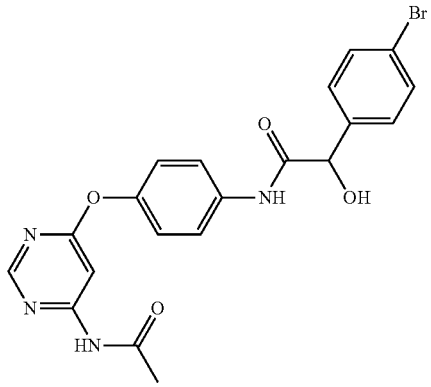 [SMILES: CC(=O)Nc1cc(Oc2ccc(NC(=O)C(O)c3ccc(Br)cc3)cc2)ncn1]

Synthesis of the compound of Example 14 was accomplished by using procedures similar to that described in Example 1. MS(ESI) m/z (M+1)+: 457.05.

Example 15: (R)—N-(4-((6-acetamidopyrimidin-4-yl)oxy)phenyl)-2-phenylpropionamide

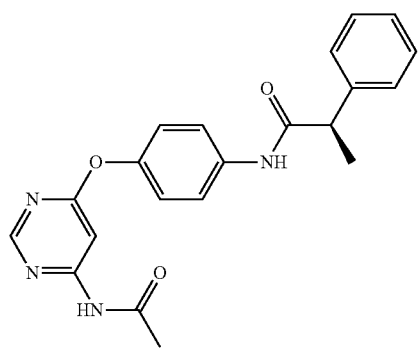 [SMILES: CC(=O)Nc1cc(Oc2ccc(NC(=O)[C@H](C)c3ccccc3)cc2)ncn1]

Synthesis of the compound of Example 15 was accomplished by using procedures similar to that described in Example 1. MS(ESI) m/z (M+1)+: 377.16.

Example 16: N-[4-(6-acetylamino-pyrimidin-4-yloxy)-phenyl]-2-(2,3-difluoro-phenyl)-acetamide

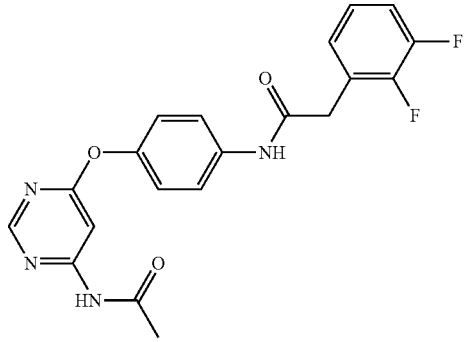 [SMILES: CC(=O)Nc1cc(Oc2ccc(NC(=O)Cc3cccc(F)c3F)cc2)ncn1]

Synthesis of the compound of Example 16 was accomplished by using procedures similar to that described in Example 1. MS(ESI) m/z (M+1)+: 399.13.

Example 17: N-[4-(6-acetylamino-pyrimidin-4-yloxy)-phenyl]-2-(2-bromo-phenyl)-acetamide

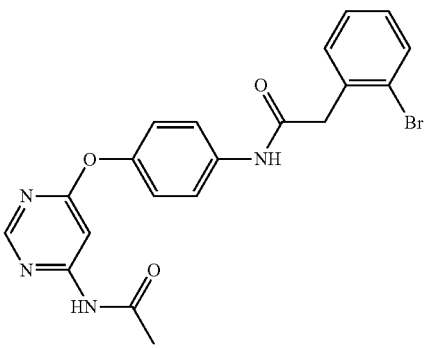 [SMILES: CC(=O)Nc1cc(Oc2ccc(NC(=O)Cc3ccccc3Br)cc2)ncn1]

Synthesis of the compound of Example 17 was accomplished by using procedures similar to that described in Example 1. MS(ESI) m/z (M+1)+: 441.06.

Example 18: N-[4-(6-acetylamino-pyrimidin-4-yloxy)-phenyl]-2-benzo[1,3]dioxol-5-yl-acetamide

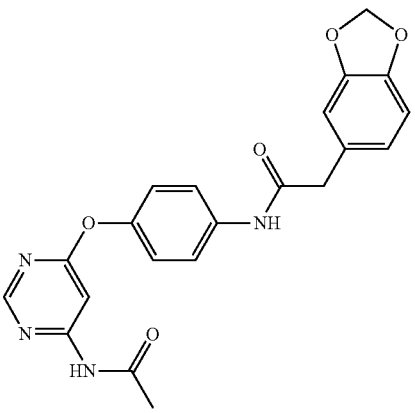 [SMILES: CC(=O)Nc1cc(Oc2ccc(NC(=O)Cc3ccc4c(c3)OCO4)cc2)ncn1]

Synthesis of the compound of Example 18 was accomplished by using procedures similar to that described in Example 1. MS(ESI) m/z (M+1)+: 407.14.

Example 19: N-[4-(6-acetylamino-pyrimidin-4-yloxy)-phenyl]-2-(4-methoxy-phenyl)-acetamide

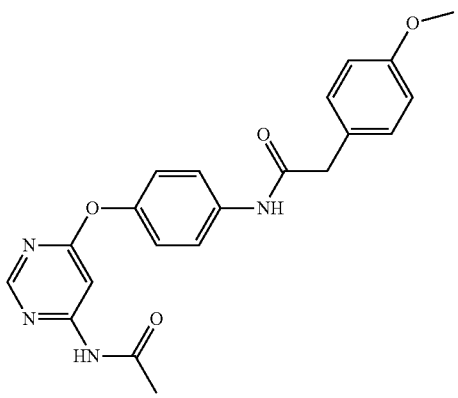 [SMILES: COc1ccc(CC(=O)Nc2ccc(Oc3cc(NC(C)=O)ncn3)cc2)cc1]

Synthesis of the compound of Example 19 was accomplished by using procedures similar to that described in Example 1. MS(ESI) m/z (M+1)+: 393.16.

Example 20: N-[4-(6-acetylamino-pyrimidin-4-yloxy)-phenyl]-2-(3,4-dichloro-phenyl)-acetamide

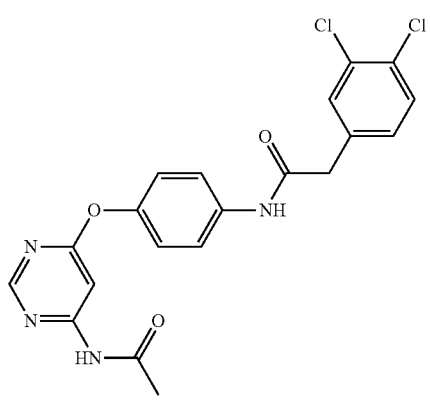 [SMILES: CC(=O)Nc1cc(Oc2ccc(NC(=O)Cc3ccc(Cl)c(Cl)c3)cc2)ncn1]

Synthesis of the compound of Example 20 was accomplished by using procedures similar to that described in Example 1. MS(ESI) m/z (M+1)+: 431.07.

Example 21: (S)—N-(4-((6-acetamidopyrimidin-4-yl)oxy)phenyl)-2-hydroxy-2-phenylacetamide

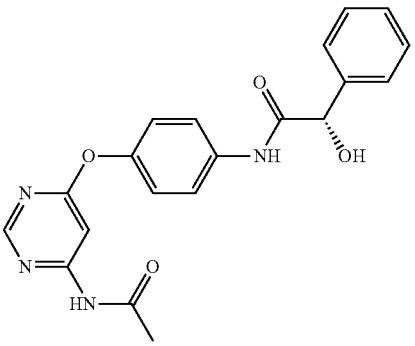 [SMILES: CC(=O)Nc1cc(Oc2ccc(NC(=O)[C@@H](O)c3ccccc3)cc2)ncn1]

Synthesis of the compound of Example 21 was accomplished by using procedures similar to that described in Example 1. MS(ESI) m/z (M+1)+: 379.14.

Example 22: (R)—N-(4-((6-acetamidopyrimidin-4-yl)oxy)phenyl)-2-hydroxy-2-phenylacetamide

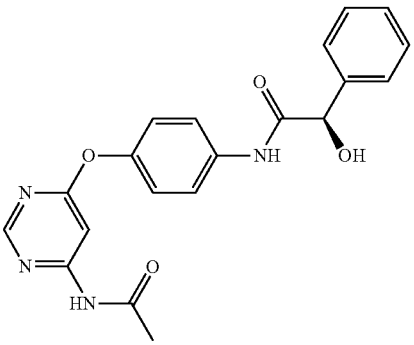 [SMILES: CC(=O)Nc1cc(Oc2ccc(NC(=O)[C@H](O)c3ccccc3)cc2)ncn1]

Synthesis of the compound of Example 22 was accomplished by using procedures similar to that described in Example 1. MS(ESI) m/z (M+1)+: 379.14.

Example 23: (S)—N-(4-((6-acetamidopyrimidin-4-yl)oxy)phenyl)-2-(4-isobutylphenyl)propionamide

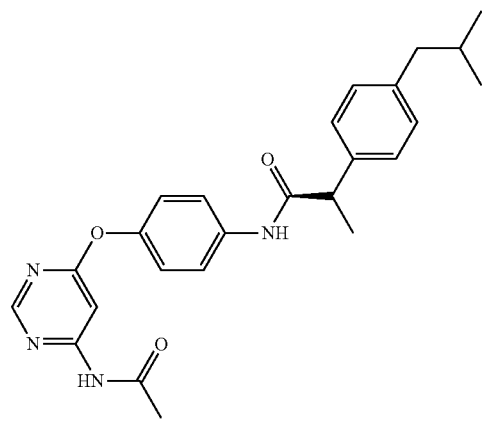

Synthesis of the compound of Example 23 was accomplished by using procedures similar to that described in Example 1. MS(ESI) m/z (M+1)+: 433.23.

Example 24: N-[4-(6-acetylamino-pyrimidin-4-yloxy)-phenyl]-2-(2-methoxy-phenyl)-acetamide

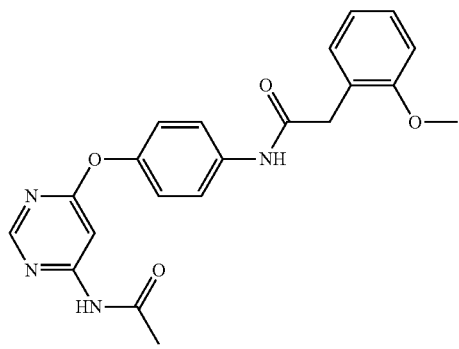 [SMILES: COc1ccccc1CC(=O)Nc1ccc(Oc2cc(NC(C)=O)ncn2)cc1]

Synthesis of the compound of Example 24 was accomplished by using procedures similar to that described in Example 1. MS(ESI) m/z (M+1)+: 392.16.

Example 25: N-[4-(6-acetylamino-pyrimidin-4-yloxy)-phenyl]-2-(2-fluoro-phenyl)-acetamide

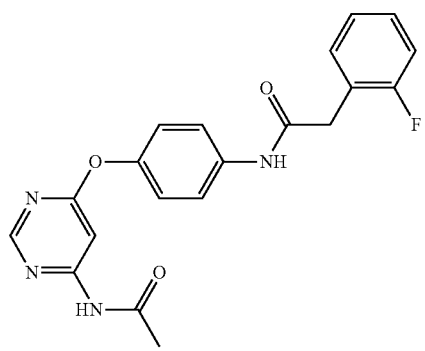 [SMILES: CC(=O)Nc1cc(Oc2ccc(NC(=O)Cc3ccccc3F)cc2)ncn1]

Synthesis of the compound of Example 25 was accomplished by using procedures similar to that described in Example 1. MS(ESI) m/z (M+1)+: 381.14.

Example 26: N-[4-(6-acetylamino-pyrimidin-4-yloxy)-phenyl]-2-(2-chloro-phenyl)-acetamide

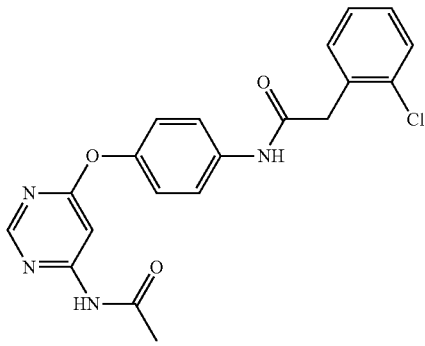 [SMILES: CC(=O)Nc1cc(Oc2ccc(NC(=O)Cc3ccccc3Cl)cc2)ncn1]

Synthesis of the compound of Example 26 was accomplished by using procedures similar to that described in Example 1. MS(ESI) m/z (M+1)+: 397.11.

Example 27: N-[4-(6-acetylamino-pyrimidin-4-yloxy)-phenyl]-2-(4-mesyl-phenyl)-acetamide

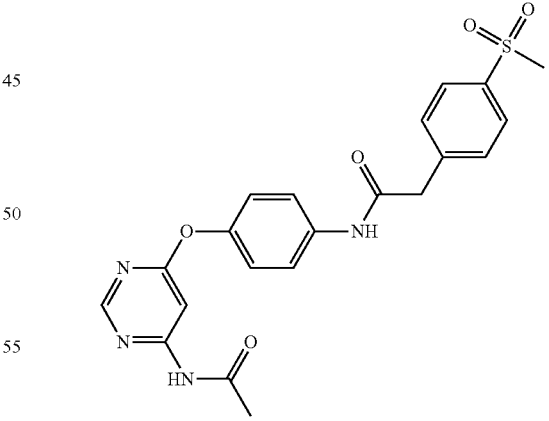

Synthesis of the compound of Example 27 was accomplished by using procedures similar to that described in Example 1. MS(ESI) m/z (M+1)+: 441.13.

Example 28: N-[4-(6-acetylamino-pyrimidin-4-yloxy)-phenyl]-2-hydroxy-2-(4-methoxy-phenyl)-acetamide

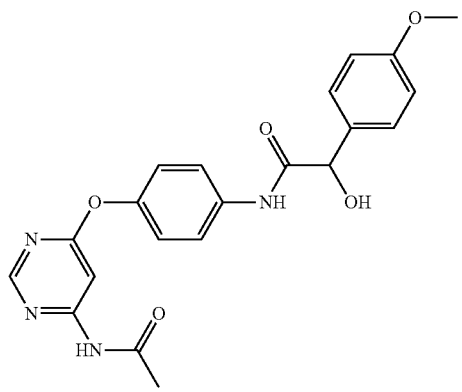 [SMILES: COc1ccc(C(O)C(=O)Nc2ccc(Oc3cc(NC(C)=O)ncn3)cc2)cc1]

Synthesis of the compound of Example 28 was accomplished by using procedures similar to that described in Example 1. MS(ESI) m/z (M+1)+: 409.15.

Example 29: (R)-(2-((4-((6-acetamidopyrimidin-4-yl)oxy)phenyl)amino)-2-oxo-1-phenethyl)aminotert-butyl Formate

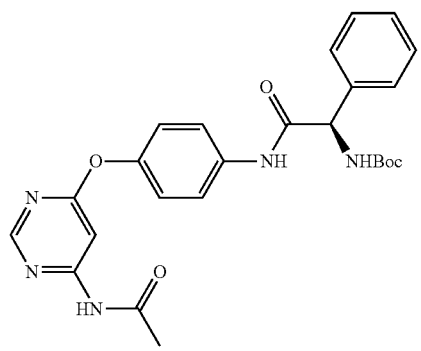 [SMILES: CC(=O)Nc1cc(Oc2ccc(NC(=O)[C@H](NC(=O)OC(C)(C)C)c3ccccc3)cc2)ncn1]

Synthesis of the compound of Example 29 was accomplished by using procedures similar to that described in Example 1. MS(ESI) m/z (M+1)+: 478.52.

Example 30: N-[4-(6-acetylamino-pyrimidin-4-yloxy)-phenyl]-2-biphenyl-4-yl-acetamide

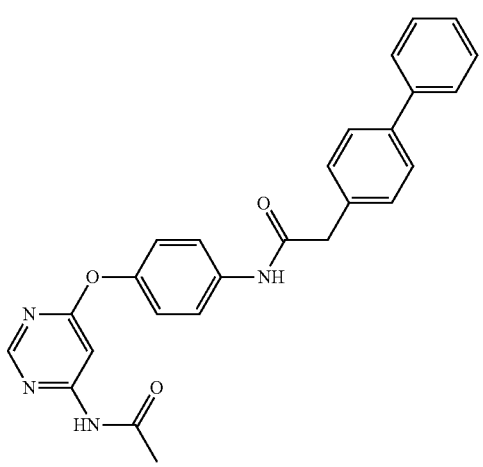 [SMILES: CC(=O)Nc1cc(Oc2ccc(NC(=O)Cc3ccc(-c4ccccc4)cc3)cc2)ncn1]

Synthesis of the compound of Example 30 was accomplished by using procedures similar to that described in Example 1. MS(ESI) m/z (M+1)+: 439.19.

Example 31: N-[4-(6-acetylamino-pyrimidin-4-yloxy)-phenyl]-2-(4-methoxy-phenyl)-acetamide Synthesis of the compound of Example 31 was accomplished by using procedures similar to that described in Example 1. MS(ESI) m/z (M+1)+: 393.16.

Example 32: 2-[4-(6-acetylamino-pyrimidin-4-yloxy)-phenyl]-N-(2-trifluoromethyl-phenyl)-acetamide

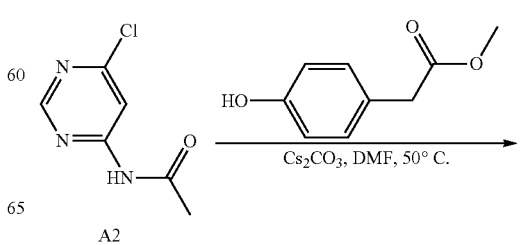

A2

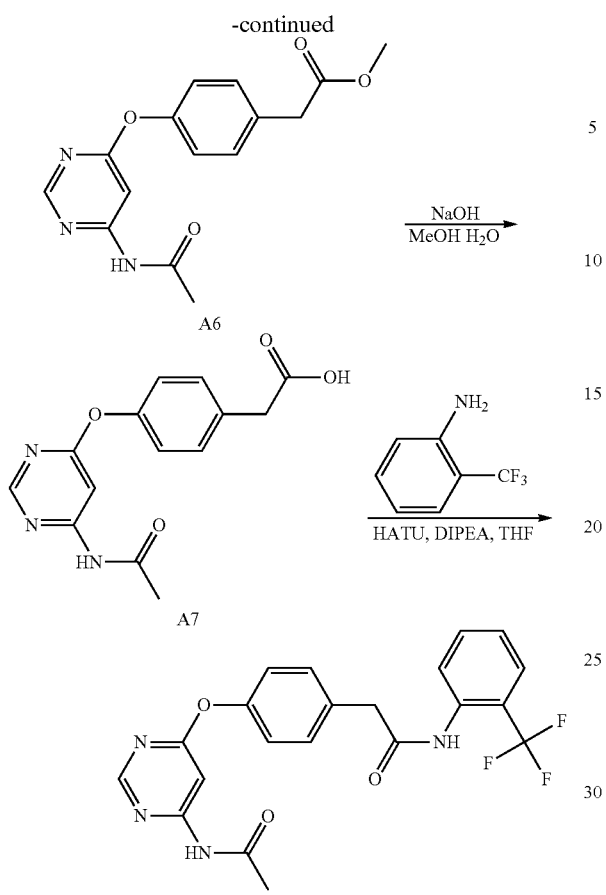

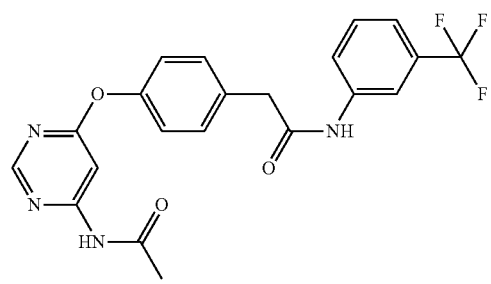 [SMILES: CC(=O)Nc1cc(Oc2ccc(CC(=O)Nc3cccc(C(F)(F)F)c3)cc2)ncn1]

[4-(6-acetamido-pyrimidin-4-yloxy)-phenyl]-methyl acetate (A6): N-(6-chloropyrimidin-4-yl)-acetamide (1.0 g) was added into a round-bottom flask, followed by addition of N,N-dimethylformamide (10 ml), (4-hydroxy-phenyl)-methyl acetate (1.45 g) and cesium carbonate (3.8 g). The reaction system was allowed to react under protection of argon at 50 degrees for 14 hours. After the reaction was completed, the solvent in the system was evaporated under reduced pressure to dryness and the resultant was diluted with water and then extracted with ethyl acetate. The organic phase was washed respectively with water and saturated saline and then dried with anhydrous sodium sulfate. The organic phase was filtered and evaporated under reduced pressure to dryness to give crude product. The crude was purified by pressurized silica gel column chromatography to give Compound (A6), LC/MS: M+H 302.12.

[4-(6-acetamido-pyrimidin-4-yloxy)-phenyl]acetic acid (A7): [4-(6-acetamido-pyrimidin-4-yloxy)-phenyl]-methyl acetate (250 mg) was added into a round-bottom flask, followed by addition of 1 mol/L of sodium hydroxide solution (5 ml) and methanol (10 ml). The reaction system was allowed to react at 80 degrees for 2 hours. After the reaction was completed, the solvent in the system was evaporated under reduced pressure to dryness. The resultant was diluted with water (50 ml) with pH adjusted to 3 to precipitate yellow solids, which were filtered to give Compound (A7), LC/MS: M+H 288.10.

2-[4-(6-acetylamino-pyrimidin-4-yloxy)-phenyl]-N-(2-trifluoromethyl-phenyl)-acetamide: [4-(6-acetamido-pyrimidin-4-yloxy)-phenyl]acetic acid (30 mg) was added into a round-bottom flask, followed by addition of tetrahydrofuran (1 ml), 2-trifluoromethyl-phenylamine (25 mg), 2-(7-azobenzotriazole)-N,N,N',N'-tetramethyluronium hexafluorophosphate HATU (60 mg) and N,N-diisopropylethylamine (0.16 ml). The reaction system was stirred under protection of argon at room temperature for 14 hours. After the reaction was completed, the solvent in the system was evaporated under reduced pressure to dryness and the resultant was diluted with water and then extracted with ethyl acetate. The organic phase was washed respectively with water and saturated saline and then dried with anhydrous sodium sulfate. The organic phase was filtered and evaporated under reduced pressure to dryness to give crude product. The crude was purified by pressurized silica gel column chromatography to give Example Compound 32, LC/MS: M+H 431.14.

Example 33: 2-[4-(6-acetylamino-pyrimidin-4-yloxy)-phenyl]-N-(3-trifluoromethyl-phenyl)-acetamide

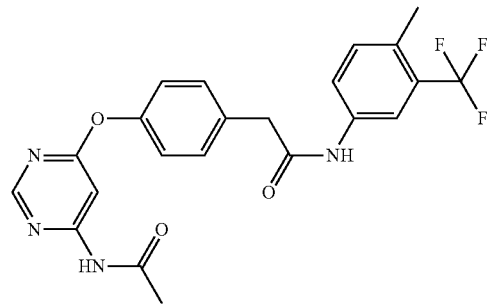 [SMILES: CC(=O)Nc1cc(Oc2ccc(CC(=O)Nc3ccc(C)c(C(F)(F)F)c3)cc2)ncn1]

Synthesis of the compound of Example 33 was accomplished by using procedures similar to that described in Example 32. MS(ESI) m/z (M+1)+: 431.14.

Example 34: 2-[4-(6-acetylamino-pyrimidin-4-yloxy)-phenyl]-N-(4-methyl-3-trifluoromethyl-phenyl)-acetamide Synthesis of the compound of Example 34 was accomplished by using procedures similar to that described in Example 32. MS(ESI) m/z (M+1)+: 445.15.

Example 35: 2-[4-(6-acetylamino-pyrimidin-4-yloxy)-phenyl]-N-(3-chloro-2-trifluoromethyl-phenyl)-acetamide

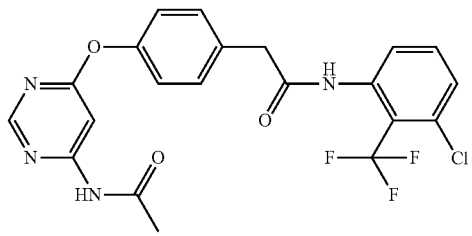 [SMILES: CC(=O)Nc1cc(Oc2ccc(CC(=O)Nc3cccc(Cl)c3C(F)(F)F)cc2)ncn1]

Synthesis of the compound of Example 35 was accomplished by using procedures similar to that described in Example 32. MS(ESI) m/z (M+1)+: 465.10.

Example 36: 2-[4-(6-acetylamino-pyrimidin-4-yloxy)-phenyl]-N-(4-trifluoromethyl-phenyl)-acetamide

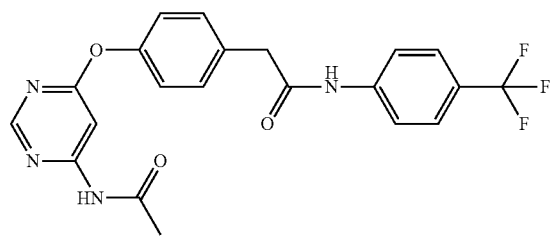 [SMILES: CC(=O)Nc1cc(Oc2ccc(CC(=O)Nc3ccc(C(F)(F)F)cc3)cc2)ncn1]

Synthesis of the compound of Example 36 was accomplished by using procedures similar to that described in Example 32. MS(ESI) m/z (M+1)+: 431.14.

Example 37: 2-[4-(6-acetylamino-pyrimidin-4-yloxy)-phenyl]-N-phenyl-acetamide

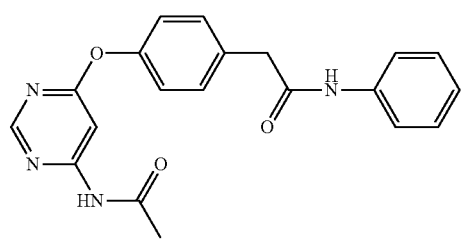 [SMILES: CC(=O)Nc1cc(Oc2ccc(CC(=O)Nc3ccccc3)cc2)ncn1]

Synthesis of the compound of Example 37 was accomplished by using procedures similar to that described in Example 32. MS(ESI) m/z (M+1)+: 363.15.

Example 38: 2-[4-(6-acetylamino-pyrimidin-4-yloxy)-phenyl]-N-(4-methyl-2-trifluoromethyl-phenyl)-acetamide

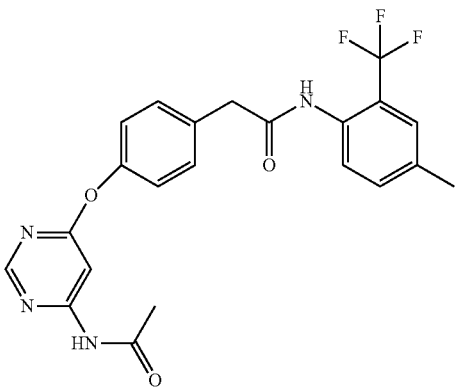 [SMILES: CC(=O)Nc1cc(Oc2ccc(CC(=O)Nc3ccc(C)cc3C(F)(F)F)cc2)ncn1]

Synthesis of the compound of Example 38 was accomplished by using procedures similar to that described in Example 32. MS(ESI) m/z (M+1)+: 445.15.

Example 39: 2-[4-(6-acetylamino-pyrimidin-4-yloxy)-phenyl]-N-(4-bromo-phenyl)-N-methyl-acetamide

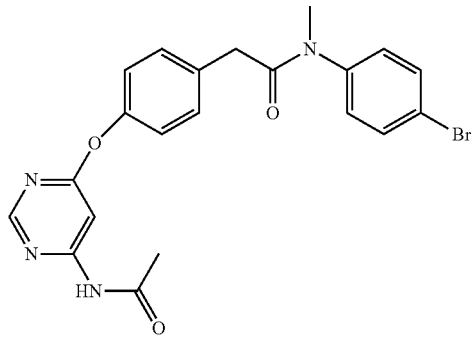 [SMILES: CC(=O)Nc1cc(Oc2ccc(CC(=O)N(C)c3ccc(Br)cc3)cc2)ncn1]

Synthesis of the compound of Example 39 was accomplished by using procedures similar to that described in Example 32. MS(ESI) m/z (M+1)+: 455.07.

Example 40: 1-{4-[6-(2-hydroxy-ethylamino)-pyrimidin-4-yloxy]-cyclohexyl}-3-(4-methyl-3-trifluoromethyl-phenyl)-urea

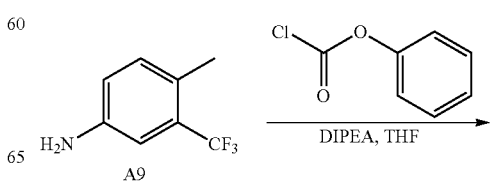

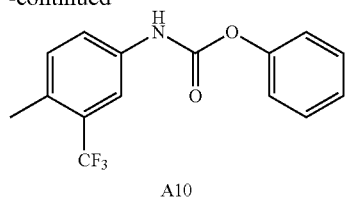
A10

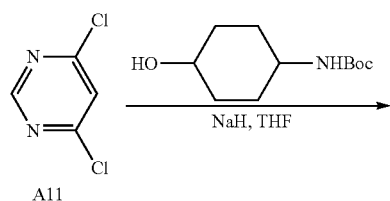
A11

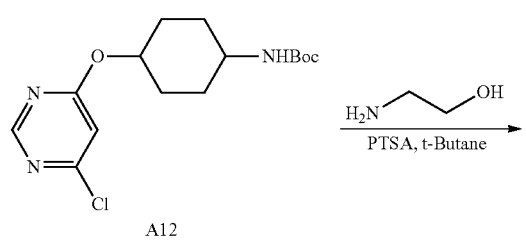
A12

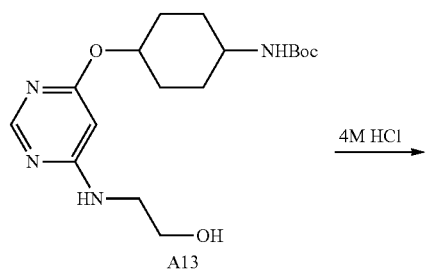
A13

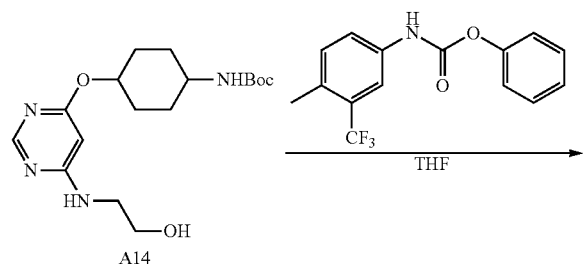
A14

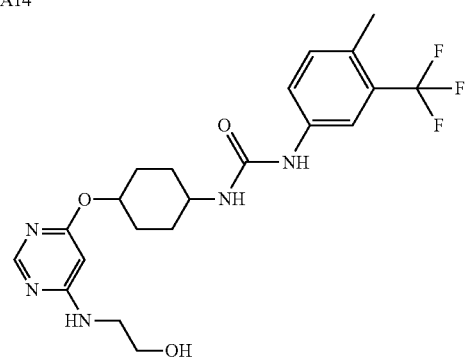

(4-methyl-3-trifluoromethyl-phenyl)-aminophenyl formate (A10): 4-methyl-3-trifluoromethyl-phenylamine (3.0 g) was added into a round-bottom flask, followed by addition of tetrahydrofuran (20 ml), phenyl chloroformate (2.67 g) and DIPEA (4.8 ml). The reaction system was allowed to react at 0 degree for 1 hour under protection of argon. After the reaction was completed, the system was diluted by addition of dichloromethane (100 ml), washed respectively with 1 mol/L hydrochloric acid (50 ml), water and saturated saline. The organic phase was dried via anhydrous sodium sulfate and evaporated under reduced pressure to dryness to give white solids A10, LC/MS: M+H 296.09.

[4-(6-chloro-pyrimidin-4-yloxy)-cyclohexyl]-aminotert-butyl formate (A12): (4-hydroxy-cyclohexyl)-aminotert-butyl formate (5.0 g) was added into a round-bottom flask, followed by addition of tetrahydrofuran (100 ml), sodium hydride (0.93 g) and 4,6-dichloro-pyrimidin (6.9 g). The reaction system was allowed to react under protection of argon at room temperature for 20 hours. After the reaction was completed, the solvent in the system was evaporated under reduced pressure to dryness and the resultant was diluted with water and then extracted with ethyl acetate. The organic phase was washed respectively with water and saturated saline and then dried with anhydrous sodium sulfate. The organic phase was filtered and evaporated under reduced pressure to dryness to give crude product. The crude was purified by pressurized silica gel column chromatography to give Compound (A12), LC/MS: M+H 328.14.

{4-[6-(2-hydroxy-ethylamino)-pyrimidin-4-yloxy]-cyclohexyl}-aminotert-butyl formate (A13): [4-(6-chloro-pyrimidin-4-yloxy)-cyclohexyl]-aminotert-butyl formate (1.0 g) was added into a round-bottom flask, followed by addition of tert-butanol (5 ml), 2-amino-ethanol (0.38 g) and p-toluenesulfonic acid (PTSA) (0.05 g). The reaction system was allowed to react under protection of argon at 60 degrees for 12 hours. After the reaction was completed, the solvent in the system was evaporated under reduced pressure to dryness, giving the crude product. The crude was purified by pressurized silica gel column chromatography to give Compound (A13), LC/MS: M+H 353.22.

2-[6-(4-amino-cyclohexyloxy)-pyrimidin-4-ylamino]-ethanol (A14): {4-[6-(2-hydroxy-ethylamino)-pyrimidin-4-yloxy]-cyclohexyl}-aminotert-butyl formate (380 mg) was added into a round-bottom flask, followed by addition of a solution of ethyl acetate in hydrochloric acid (2 ml) and methanol (1 ml). The reaction system was allowed to react at room temperature for 14 hours. After the reaction was completed, the solvent in the system was evaporated under reduced pressure to dryness to give Compound (A14), LC/MS: M+H 253.17.

1-{4-[6-(2-hydroxy-ethylamino)-pyrimidin-4-yloxy]-cyclohexyl}-3-(4-methyl-3-trifluoromethyl-phenyl)-urea: 2-[6-(4-amino-cyclohexyloxy)-pyrimidin-4-ylamino]-ethanol (32.6 mg) was added into a round-bottom flask, followed by addition of tetrahydrofuran (1 ml) and (4-methyl-3-trifluoromethyl-phenyl)-aminophenyl formate (44 mg). The reaction system was stirred under protection of argon at 60 degrees for 14 hours. After the reaction was completed, the solvent in the system was evaporated under reduced pressure to dryness, The crude was purified by pressurized silica gel column chromatography to give Example Compound 40, LC/MS: M+H 454.21.

Example 41: 1-{4-[6-(2-methoxy-ethylamino)-pyrimidin-4-yloxy]-cyclohexyl}-3-(4-methyl-3-trifluoromethyl-phenyl)-urea

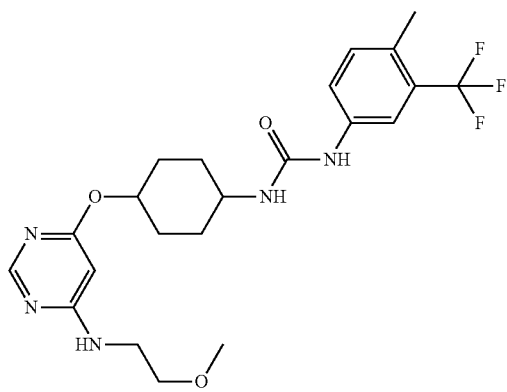 [SMILES: COCCNc1cc(OC2CCC(NC(=O)Nc3ccc(C)c(C(F)(F)F)c3)CC2)ncn1]

Synthesis of the compound of Example 41 was accomplished by using procedures similar to that described in Example 40. MS(ESI) m/z (M+1)+: 468.22.

Example 42: 1-((1R,4R)-4-((6-((2-hydroxyethyl)amino)pyrimidin-4-yl)oxy)cyclohexyl)-3-(4-methyl-3-(trifluoromethyl)phenyl)urea

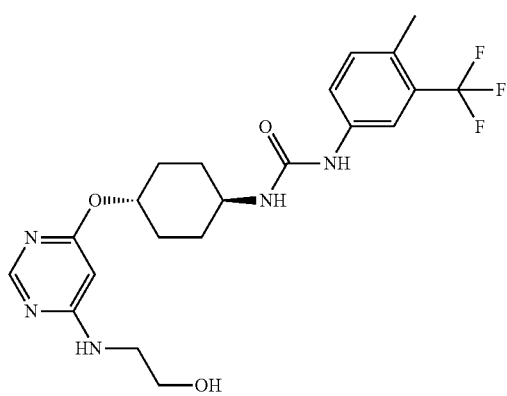 [SMILES: Cc1ccc(NC(=O)N[C@H]2CC[C@H](Oc3cc(NCCO)ncn3)CC2)cc1C(F)(F)F]

Synthesis of the compound of Example 42 was accomplished by using procedures similar to that described in Example 40. MS(ESI) m/z (M+1)+: 454.21.

Example 43: 1-((1R,4R)-4-((6-((2-methoxyethyl)amino)pyrimidin-4-yl)oxy)cyclohexyl)-3-(4-methyl-3-(trifluoromethyl)phenyl)urea

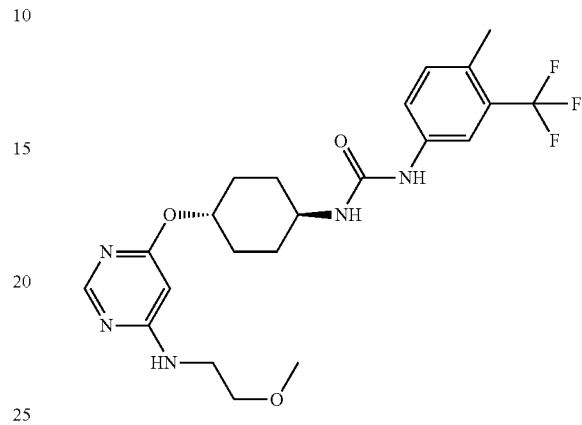

Synthesis of the compound of Example 43 was accomplished by using procedures similar to that described in Example 42. MS(ESI) m/z (M+1)+: 468.13.

Example 44: 1-((1S,4S)-4-((6-((2-hydroxyethyl)amino)pyrimidin-4-yl)oxy)cyclohexyl)-3-(4-methyl-3-(trifluoromethyl)phenyl)urea

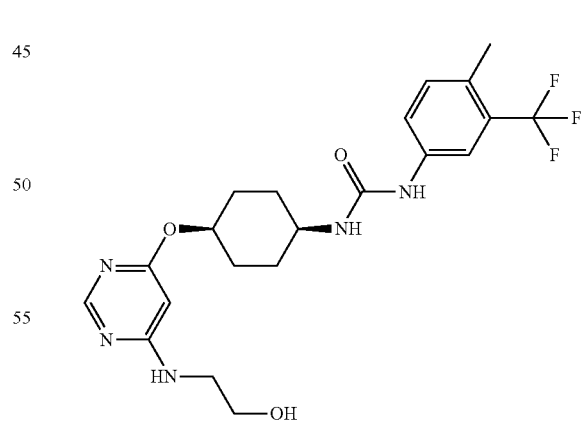

Synthesis of the compound of Example 44 was accomplished by using procedures similar to that described in Example 42. MS(ESI) m/z (M+1)+: 454.21.

Example 45: 1-((1S,4S)-4-((6-((2-methoxyethyl)amino)pyrimidin-4-yl)oxy)cyclohexyl)-3-(4-methyl-3-(trifluoromethyl)phenyl)urea

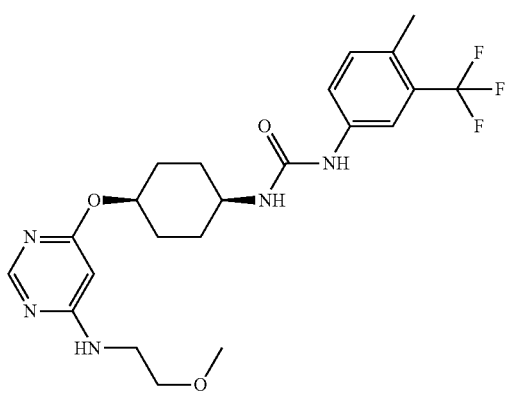 [SMILES: COCCNc1cc(O[C@H]2CC[C@@H](NC(=O)Nc3ccc(C)c(C(F)(F)F)c3)CC2)ncn1]

Synthesis of the compound of Example 45 was accomplished by using procedures similar to that described in Example 42. MS(ESI) m/z (M+1)+: 468.22.

Example 46: 1-((1R,4R)-4-((6-((2-aminoethyl)amino)pyrimidin-4-yl)oxy)cyclohexyl)-3-(4-methyl-3-(trifluoromethyl)phenyl)urea

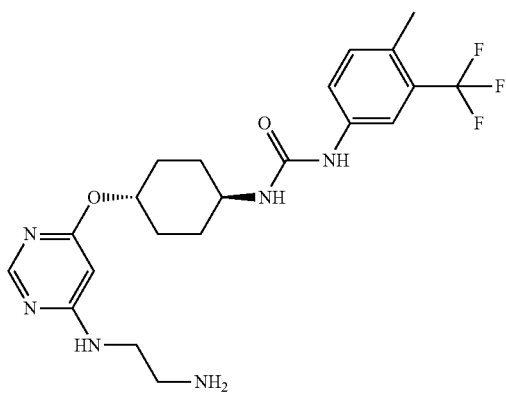 [SMILES: Cc1ccc(NC(=O)N[C@H]2CC[C@H](Oc3cc(NCCN)ncn3)CC2)cc1C(F)(F)F]

Synthesis of the compound of Example 46 was accomplished by using procedures similar to that described in Example 42. MS(ESI) m/z (M+1)+: 453.22.

Example 47: N-(6-{4-[2-(2-trifluoromethyl-phenyl)-acetylamino]-phenoxy}-pyrimidin-4-yl)-propanamide

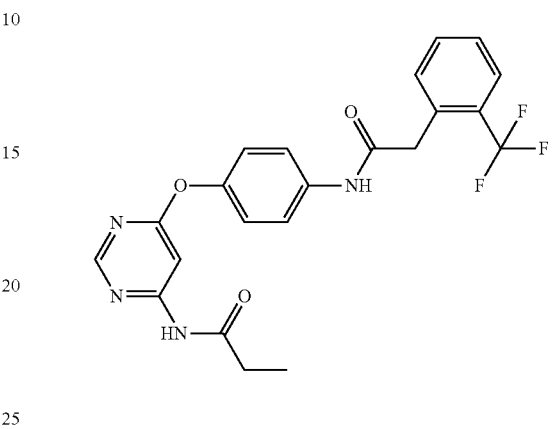

Synthesis of the compound of Example 47 was accomplished by using procedures similar to that described in Example 1. MS(ESI) m/z (M+1)+: 445.15.

Example 48: N-(6-{4-[2-(4-trifluoromethyl-phenyl)-acetylamino]-phenoxy}-pyrimidin-4-yl)-propanamide

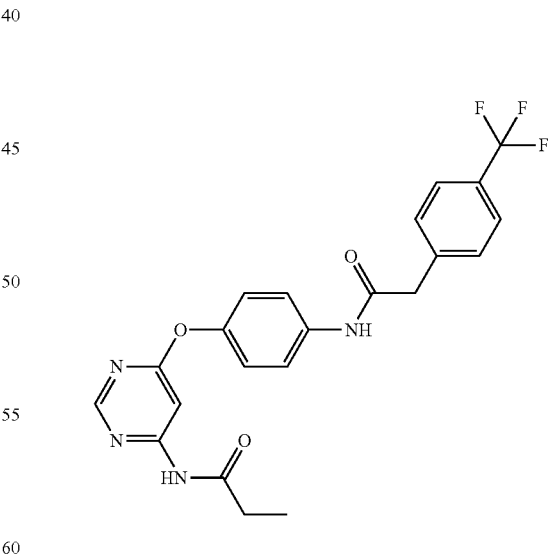

Synthesis of the compound of Example 48 was accomplished by using procedures similar to that described in Example 1. MS(ESI) m/z (M+1)+: 445.15.

Example 49: N-(6-{4-[2-(2-trifluoromethyl-phenyl)-acetylamino]-phenoxy}-pyrimidin-4-yl)-isobutyramide

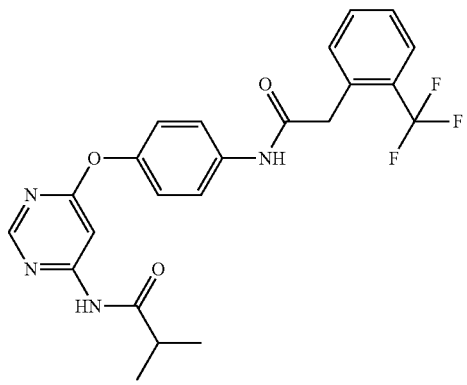 [SMILES: CC(C)C(=O)Nc1cc(Oc2ccc(NC(=O)Cc3ccccc3C(F)(F)F)cc2)ncn1]

Synthesis of the compound of Example 49 was accomplished by using procedures similar to that described in Example 1. MS(ESI) m/z (M+1)+: 459.17.

Example 50: N-(6-{4-[2-(3-trifluoromethyl-phenyl)-acetylamino]-phenoxy}-pyrimidin-4-yl)-isobutyramide

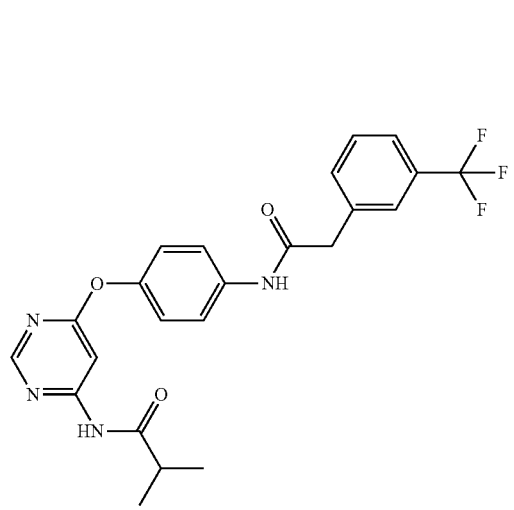 [SMILES: CC(C)C(=O)Nc1cc(Oc2ccc(NC(=O)Cc3cccc(C(F)(F)F)c3)cc2)ncn1]

Synthesis of the compound of Example 50 was accomplished by using procedures similar to that described in Example 1. MS(ESI) m/z (M+1)+: 459.17.

Example 51: N-(6-{4-[2-(4-trifluoromethyl-phenyl)-acetylamino]-phenoxy}-pyrimidin-4-yl)-isobutyramide

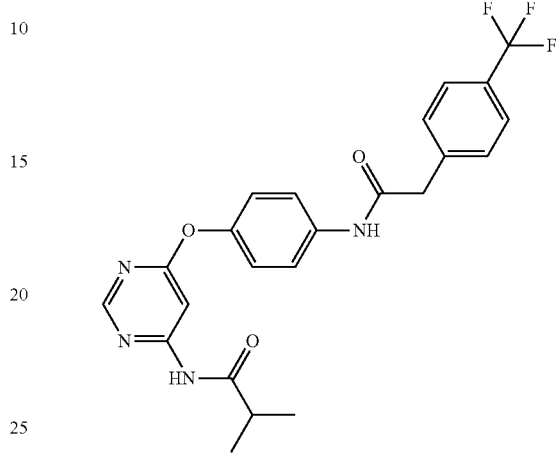

Synthesis of the compound of Example 51 was accomplished by using procedures similar to that described in Example 1. MS(ESI) m/z (M+1)+: 459.17.

Example 52: 2,2-dimethyl-N-(6-{4-[2-(4-trifluoromethyl-phenyl)-acetylamino]-phenoxy}-pyrimidin-4-yl)-propanamide

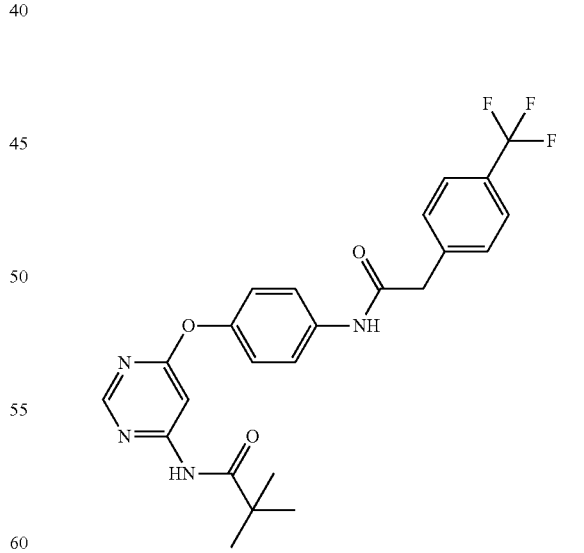

Synthesis of the compound of Example 52 was accomplished by using procedures similar to that described in Example 1. MS(ESI) m/z (M+1)+: 473.18.

Example 53: N-(6-{4-[2-(3-trifluoromethyl-phenyl)-acetylamino]-phenoxy}-pyrimidin-4-yl)-butyramide

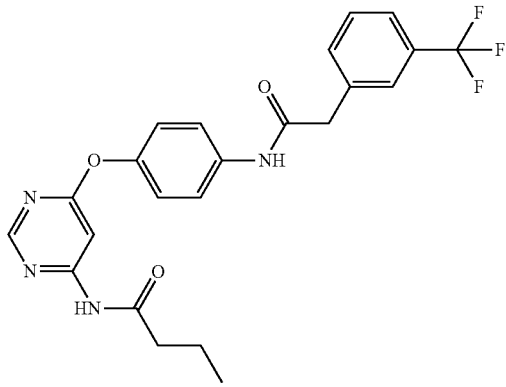 [SMILES: CCCC(=O)Nc1cc(Oc2ccc(NC(=O)Cc3cccc(C(F)(F)F)c3)cc2)ncn1]

Synthesis of the compound of Example 53 was accomplished by using procedures similar to that described in Example 1. MS(ESI) m/z (M+1)+: 459.17.

Example 54: N-(6-{4-[2-(3-trifluoromethyl-phenyl)-acetylamino]-phenoxy}-pyrimidin-4-yl)-propanamide

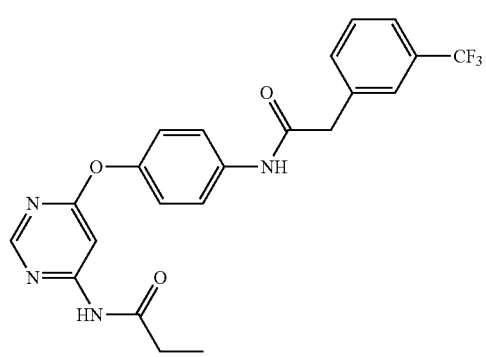 [SMILES: CCC(=O)Nc1cc(Oc2ccc(NC(=O)Cc3cccc(C(F)(F)F)c3)cc2)ncn1]

Synthesis of the compound of Example 54 was accomplished by using procedures similar to that described in Example 1. MS(ESI) m/z (M+1)+: 445.15.

Example 55: N-(6-{4-[2-(2-trifluoromethyl-phenyl)-acetylamino]-phenoxy}-pyrimidin-4-yl)-valeramide

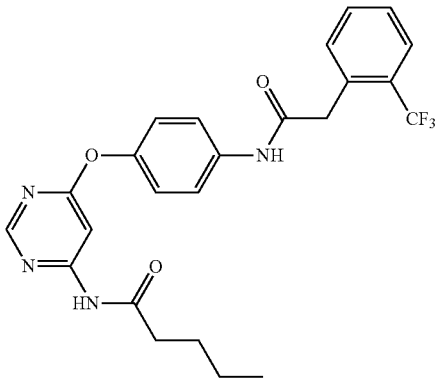 [SMILES: CCCCC(=O)Nc1cc(Oc2ccc(NC(=O)Cc3ccccc3C(F)(F)F)cc2)ncn1]

Synthesis of the compound of Example 55 was accomplished by using procedures similar to that described in Example 1. MS(ESI) m/z (M+1)+: 473.18.

Example 56: N-(6-{4-[2-(4-trifluoromethyl-phenyl)-acetamido]-phenoxy}-pyrimidin-4-yl)-valeramide

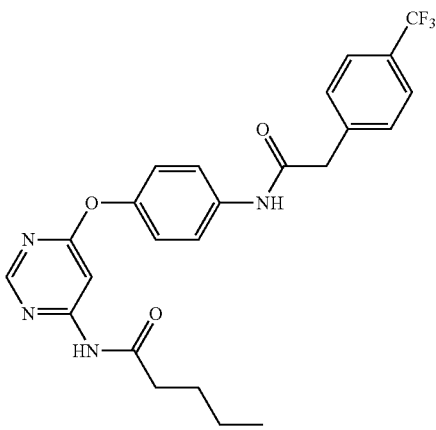 [SMILES: CCCCC(=O)Nc1cc(Oc2ccc(NC(=O)Cc3ccc(C(F)(F)F)cc3)cc2)ncn1]

Synthesis of the compound of Example 56 was accomplished by using procedures similar to that described in Example 1. MS(ESI) m/z (M+1)+: 473.18.

Example 57: 1-{4-[6-(4-methoxy-benzylamino)-pyrimidin-4-yloxy]-phenyl}-3-(4-methyl-3-trifluoromethyl-phenyl)-urea

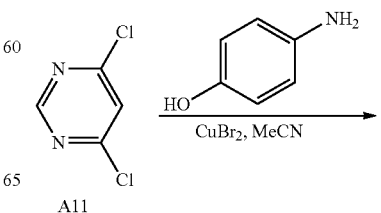

A11

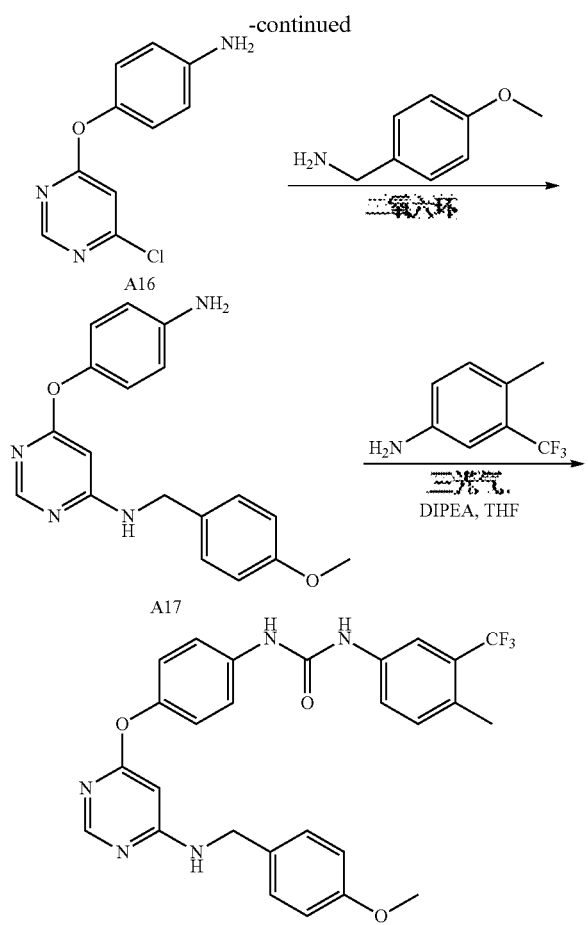

4-(6-chloro-pyrimidin-4-yloxy)-phenylamine (A16): 4,6-dichloro-pyrimidin (10.0 g) was added into a round-bottom flask, followed by addition of acetonitrile (120 ml), 4-aminophenol (7.32 g), potassium carbonate (18.55 g) and copper bromide (10 mg). The reaction system was allowed to react under protection of argon at room temperature for 24 hours. After the reaction was completed, the solvent in the system was evaporated under reduced pressure to dryness and the resultant was diluted with water and then extracted with ethyl acetate. The organic phase was washed respectively with water and saturated saline and then dried with anhydrous sodium sulfate. The organic phase was filtered and evaporated under reduced pressure to dryness to give crude product. The crude was recrystallized with ethyl acetate to give Compound (A16), LC/MS: M+H 222.05.

[6-(4-amino-phenoxy)-pyrimidin-4-yl]-(4-methoxy-benzyl)-amine (A17): 4-(6-chloro-pyrimidin-4-yloxy)-phenylamine (1.0 g) was added into a round-bottom flask, followed by addition of dioxane (6 ml) and 4-methoxy-benzylamine (1.24 g). The reaction system was allowed to react under protection of argon at 140 degrees for 14 hours. After the reaction was completed, the solvent in the system was evaporated under reduced pressure to dryness, and the resultant was diluted with 1 mol/L sodium hydroxide solution and then extracted with ethyl acetate. The organic phase was washed respectively with water and saturated saline and then dried with anhydrous sodium sulfate. The organic phase was filtered and evaporated under reduced pressure to dryness to give crude product. The crude was purified by pressurized silica gel column chromatography to give Compound (A17), LC/MS: M+H 323.15.

1-{4-[6-(4-methoxy-benzylamino)-pyrimidin-4-yloxy]-phenyl}-3-(4-methyl-3-trifluoromethyl-phenyl)-urea: [6-(4-amino-phenoxy)-pyrimidin-4-yl]-(4-methoxy-benzyl)-amine (500 mg) was added into a round-bottom flask, followed by addition of tetrahydrofuran (5 ml), DIPEA (1.1 ml) and triphosgene (0.204 g). The reaction system was stirred under protection of argon at 0 degree for 1 hour, and continued to react for 16 hours after returned to room temperature. After the reaction was completed, the solvent in the system was evaporated under reduced pressure to dryness and the resultant was diluted with water and then extracted with ethyl acetate. The organic phase was washed respectively with water and saturated saline and then dried with anhydrous sodium sulfate. The organic phase was filtered and evaporated under reduced pressure to dryness to give crude product. The crude was purified by pressurized silica gel column chromatography to give Example Compound 57, LC/MS: M+H 524.19.

Example 58: N-(6-{4-[3-(4-methyl-3-trifluoromethyl-phenyl)-ureido]-phenoxy}-pyrimidin-4-yl)-acrylamide

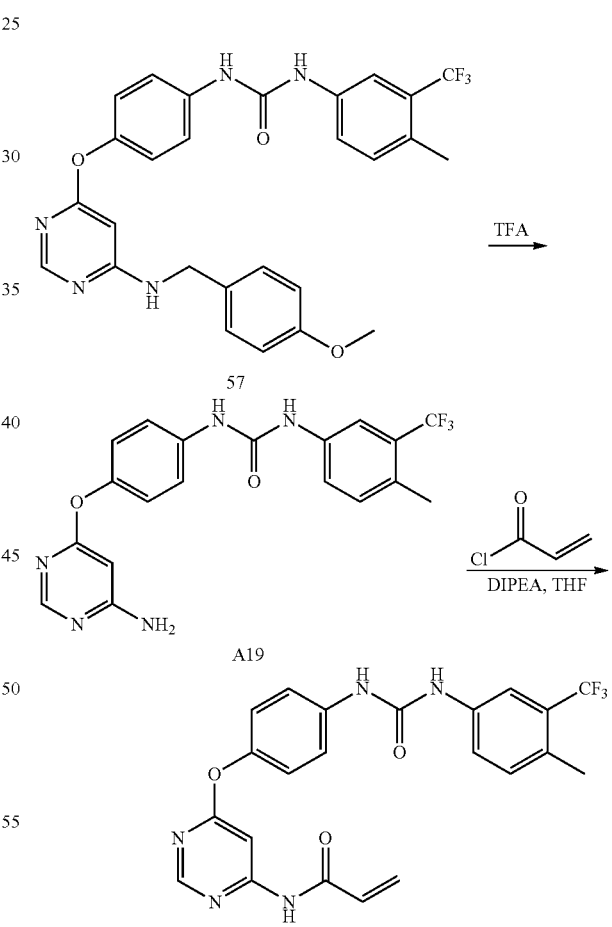

1-[4-(6-amino-pyrimidin-4-yloxy)-phenyl]-3-(4-methyl-3-trifluoromethyl-phenyl)-urea (A19): 1-{4-[6-(4-methoxy-benzylamino)-pyrimidin-4-yloxy]-phenyl}-3-(4-methyl-3-trifluoromethyl-phenyl)-urea (140 mg) was added into a round-bottom flask, followed by addition of trifluoroacetic acid (3 ml). The reaction system was stirred under protection of argon at 80 degrees for 12 hours. After the reaction was completed, the solvent in the system was evaporated under reduced pressure to dryness to give a crude product. The crude was purified by pressurized silica gel column chromatography to give Compound (A19), LC/MS: M+H 404.14.

N-(6-{4-[3-(4-methyl-3-trifluoromethyl-phenyl)-ureido]-phenoxy}-pyrimidin-4-yl)-acrylamide: 1-[4-(6-amino-pyrimidin-4-yloxy)-phenyl]-3-(4-methyl-3-trifluoromethyl-phenyl)-urea (20 mg) was added into a round-bottom flask, followed by addition of tetrahydrofuran (2 ml), DIPEA (0.15 ml) and acryloyl chloride (0.055 ml). The reaction system was stirred under protection of argon at 0 degree for half an hour. After the reaction was completed, the solvent in the system was evaporated under reduced pressure to dryness and the resultant was diluted with water and then extracted with ethyl acetate. The organic phase was washed respectively with water and saturated saline and then dried with anhydrous sodium sulfate. The organic phase was filtered and evaporated under reduced pressure to dryness to give crude product. The crude was purified by pressurized silica gel column chromatography to give Example Compound 58, LC/MS: M+H 458.15.

Example 59: N-(6-{4-[3-(4-methyl-3-trifluoromethyl-phenyl)-ureido]-phenoxy}-pyrimidin-4-yl)-propanamide

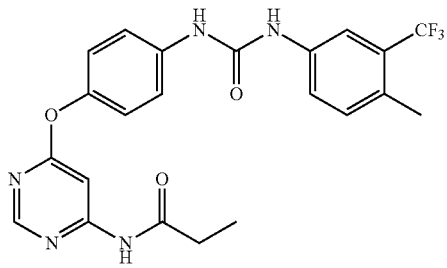 [SMILES: CCC(=O)Nc1cc(Oc2ccc(NC(=O)Nc3ccc(C)c(C(F)(F)F)c3)cc2)ncn1]

Synthesis of the compound of Example 59 was accomplished by using procedures similar to that described in Example 57. MS(ESI) m/z (M+1)+: 460.16.

Example 60: N-[4-(6-acetylamino-pyrimidin-4-yloxy)-phenyl]-2-(3,4-dimethyl-phenyl)-acetamide

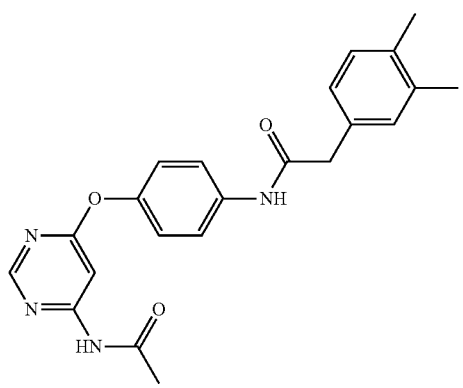 [SMILES: CC(=O)Nc1cc(Oc2ccc(NC(=O)Cc3ccc(C)c(C)c3)cc2)ncn1]

Synthesis of the compound of Example 60 was accomplished by using procedures similar to that described in Example 1. MS(ESI) m/z (M+1)+: 391.18.

Example 61: N-[4-(6-acetylamino-pyrimidin-4-yloxy)-phenyl]-2-(3,4-dimethoxy-phenyl)-acetamide

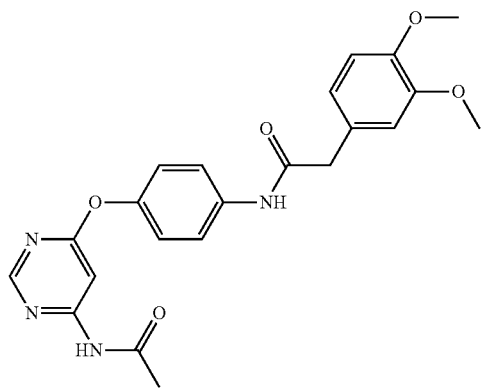 [SMILES: COc1ccc(CC(=O)Nc2ccc(Oc3cc(NC(C)=O)ncn3)cc2)cc1OC]

Synthesis of the compound of Example 61 was accomplished by using procedures similar to that described in Example 1. MS(ESI) m/z (M+1)+: 423.17.

Example 62: N-[4-(6-acetylamino-pyrimidin-4-yloxy)-phenyl]-2-(3,4,5-trimethoxy-phenyl)-acetamide

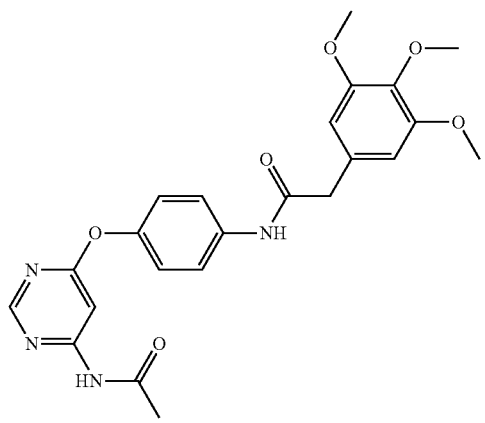 [SMILES: COc1cc(CC(=O)Nc2ccc(Oc3cc(NC(C)=O)ncn3)cc2)cc(OC)c1OC]

Synthesis of the compound of Example 62 was accomplished by using procedures similar to that described in Example 1. MS(ESI) m/z (M+1)+: 453.18.

Example 63: N-[4-(6-acetylamino-pyrimidin-4-yloxy)-phenyl]-2-(2-fluoro-phenyl)-2-hydroxy-acetamide

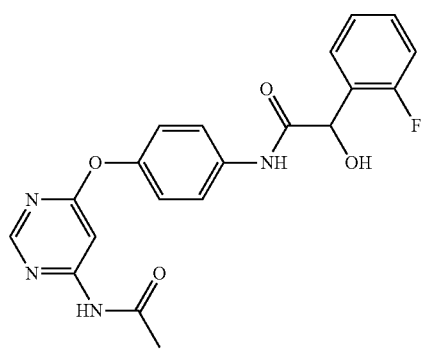 [SMILES: CC(=O)Nc1cc(Oc2ccc(NC(=O)C(O)c3ccccc3F)cc2)ncn1]

Synthesis of the compound of Example 63 was accomplished by using procedures similar to that described in Example 1. MS(ESI) m/z (M+1)+: 397.13.

Example 64: N-[4-(6-acetylamino-pyrimidin-4-yloxy)-phenyl]-2-(3-fluoro-4-hydroxy-phenyl)-acetamide

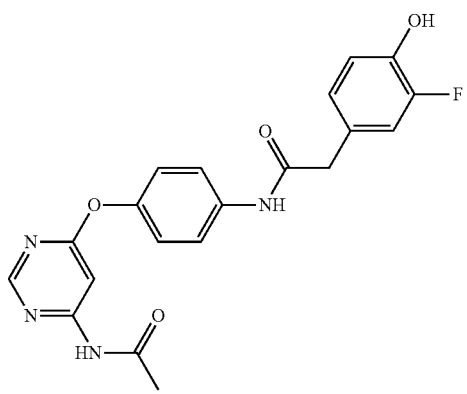 [SMILES: CC(=O)Nc1cc(Oc2ccc(NC(=O)Cc3ccc(O)c(F)c3)cc2)ncn1]

Synthesis of the compound of Example 64 was accomplished by using procedures similar to that described in Example 1. MS(ESI) m/z (M+1)+: 397.13.

Example 65: N-[4-(6-acetylamino-pyrimidin-4-yloxy)-phenyl]-2-(4-tert-butyl-phenyl)-acetamide

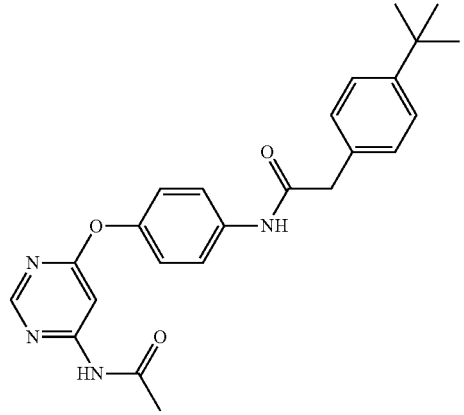 [SMILES: CC(=O)Nc1cc(Oc2ccc(NC(=O)Cc3ccc(C(C)(C)C)cc3)cc2)ncn1]

Synthesis of the compound of Example 65 was accomplished by using procedures similar to that described in Example 1. MS(ESI) m/z (M+1)+: 419.21.

Example 66: N-[4-(6-acetylamino-pyrimidin-4-yloxy)-phenyl]-2-(2,6-difluoro-phenyl)-acetamide

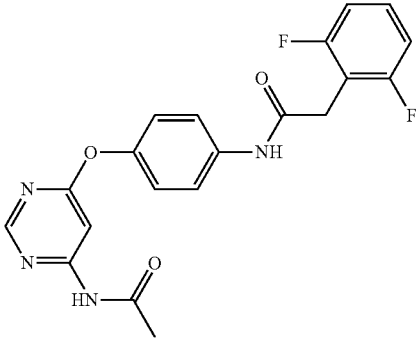 [SMILES: CC(=O)Nc1cc(Oc2ccc(NC(=O)Cc3c(F)cccc3F)cc2)ncn1]

Synthesis of the compound of Example 66 was accomplished by using procedures similar to that described in Example 1. MS(ESI) m/z (M+1)+: 399.13.

Example 67: N-[4-(6-acetylamino-pyrimidin-4-ylsulfanyl)-phenyl]-2-(2-trifluoromethyl-phenyl)-acetamide

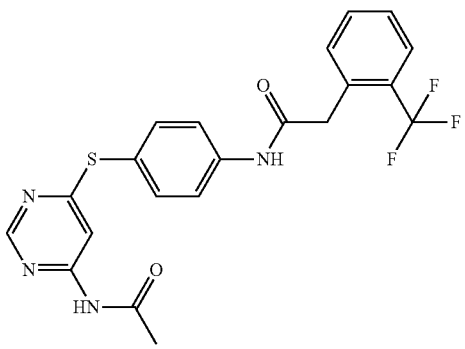 [SMILES: CC(=O)Nc1cc(Sc2ccc(NC(=O)Cc3ccccc3C(F)(F)F)cc2)ncn1]

Synthesis of the compound of Example 67 was accomplished by using procedures similar to that described in Example 1. MS(ESI) m/z (M+1)+: 447.11.

Example 68: N-[4-(6-acetylamino-pyrimidin-4-ylsulfanyl)-phenyl]-2-(3-trifluoromethyl-phenyl)-acetamide

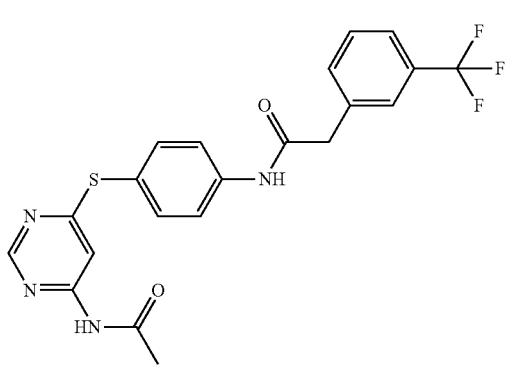 [SMILES: CC(=O)Nc1cc(Sc2ccc(NC(=O)Cc3cccc(C(F)(F)F)c3)cc2)ncn1]

Synthesis of the compound of Example 68 was accomplished by using procedures similar to that described in Example 1. MS(ESI) m/z (M+1)+: 447.11.

Example 69: N-[4-(6-acetylamino-pyrimidin-4-ylsulfanyl)-phenyl]-2-(4-trifluoromethyl-phenyl)-acetamide

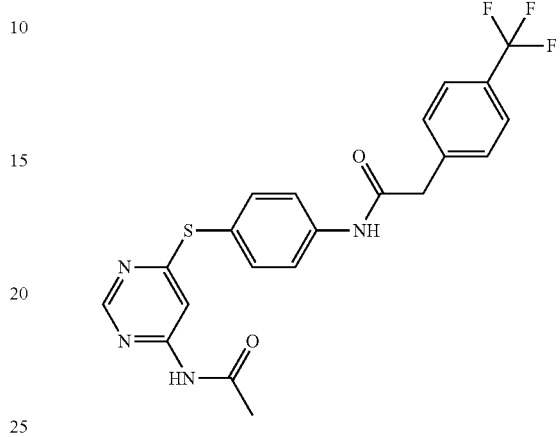

Synthesis of the compound of Example 69 was accomplished by using procedures similar to that described in Example 1. MS(ESI) m/z (M+1)+: 447.11.

Example 70: 1-{4-[6-(2-methoxy-ethylamino)-pyrimidin-4-yloxy]-phenyl}-3-[4-(4-methyl-piperazin-1-ylmethyl)-3-trifluoromethyl-phenyl]-urea

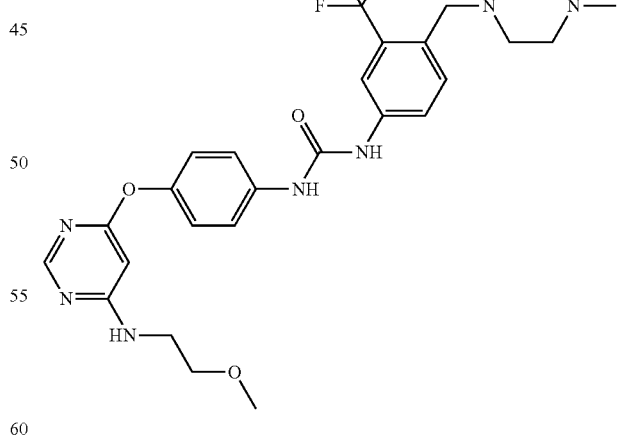

Synthesis of the compound of Example 70 was accomplished by using procedures similar to that described in Example 57. MS(ESI) m/z (M+1)+: 560.26.

Example 71: 1-{4-[6-(2-methoxy-ethylamino)-pyrimidin-4-yloxy]-phenyl}-3-(2-trifluoromethyl-phenyl)-urea

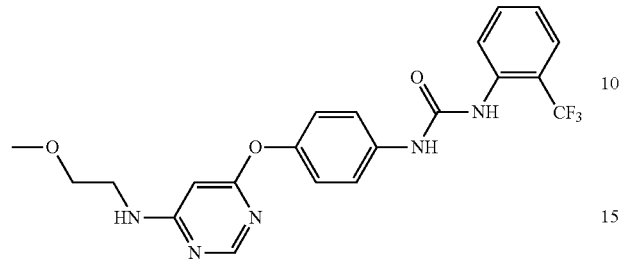

Synthesis of the compound of Example 71 was accomplished by using procedures similar to that described in Example 57. MS(ESI) m/z (M+1)+: 448.16.

Example 72: 1-{4-[6-(2-methoxy-ethylamino)-pyrimidin-4-yloxy]-phenyl}-3-(3-trifluoromethyl-phenyl)-urea

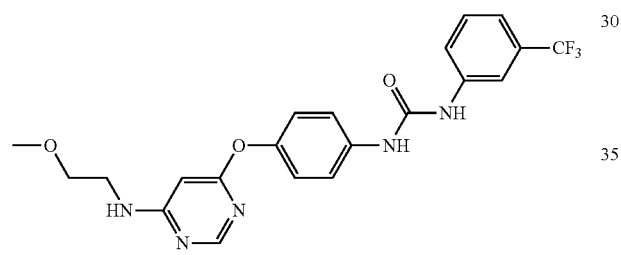

Synthesis of the compound of Example 72 was accomplished by using procedures similar to that described in Example 57. MS(ESI) m/z (M+1)+: 448.16.

Example 73: 1-{4-[6-(2-methoxy-ethylamino)-pyrimidin-4-yloxy]-phenyl}-3-(4-trifluoromethyl-phenyl)-urea

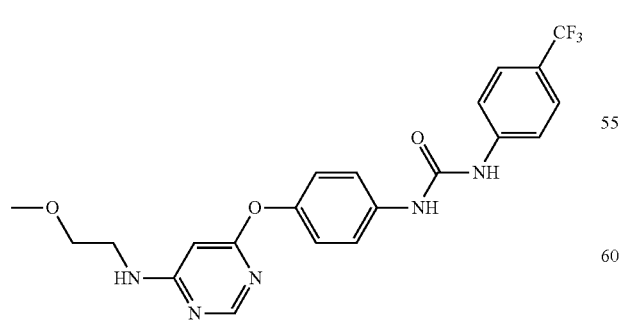

Synthesis of the compound of Example 73 was accomplished by using procedures similar to that described in Example 57. MS(ESI) m/z (M+1)+: 448.16.

Example 74: (R)-4-(6-(4-(2-(2,4-difluorophenyl)acetamido)phenoxy)pyrimidin-4-yl)-2-methylpiperazin-1-tert-butyl Formate

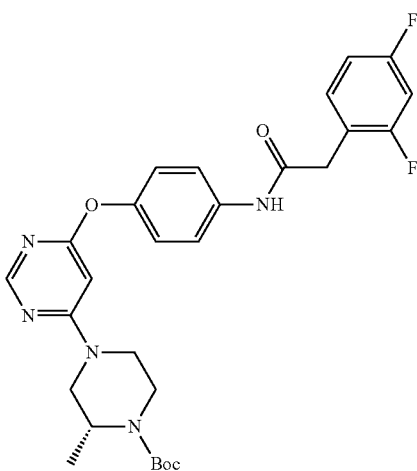 [SMILES: C[C@@H]1CN(c2cc(Oc3ccc(NC(=O)Cc4ccc(F)cc4F)cc3)ncn2)CCN1C(=O)OC(C)(C)C]

Synthesis of the compound of Example 74 was accomplished by using procedures similar to that described in Example 1. MS(ESI) m/z (M+1)+: 540.24.

Example 75: (R)-2-(2,4-difluorophenyl)-N-(4-((6-(2-methylpiperazin-1-yl)pyrimidin-4-yl)oxy)phenyl)acetamide

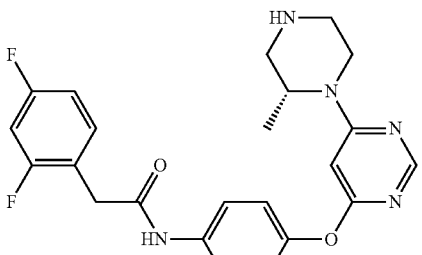

Synthesis of the compound of Example 75 was accomplished by using procedures similar to that described in Example 1. MS(ESI) m/z (M+1)+: 440.19.

Example 76: 2-(2,4-difluoro-phenyl)-N-{4-[6-(2-methoxy-ethylamino)-pyrimidin-4-yloxy]-phenyl}-acetamide

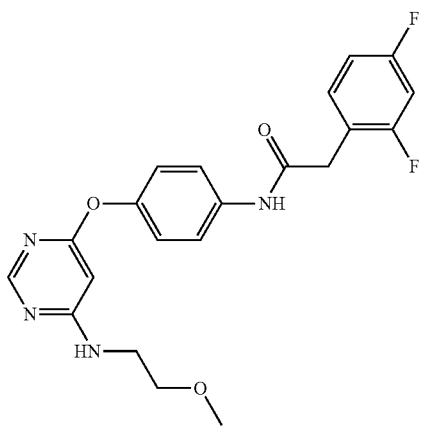 [SMILES: COCCNc1cc(Oc2ccc(NC(=O)Cc3ccc(F)cc3F)cc2)ncn1]

Synthesis of the compound of Example 76 was accomplished by using procedures similar to that described in Example 1. MS(ESI) m/z (M+1)+: 415.16.

Example 77: 2-(2,4-difluoro-phenyl)-N-{4-[6-(2-hydroxy-ethylamino)-pyrimidin-4-yloxy]-phenyl}-acetamide

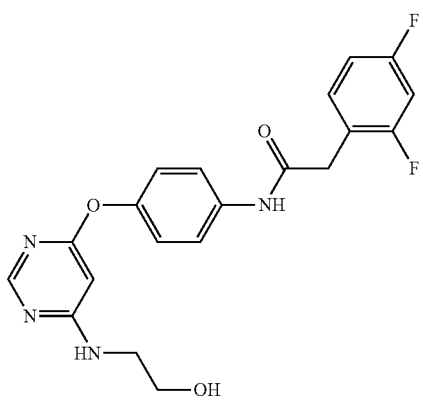 [SMILES: O=C(Cc1ccc(F)cc1F)Nc1ccc(Oc2cc(NCCO)ncn2)cc1]

Synthesis of the compound of Example 77 was accomplished by using procedures similar to that described in Example 1. MS(ESI) m/z (M+1)+: 401.14.

Example 78: 2-(2,4-difluoro-phenyl)-N-{4-[6-(2-dimethylamino-ethylamino)-pyrimidin-4-yloxy]-phenyl}-acetamide

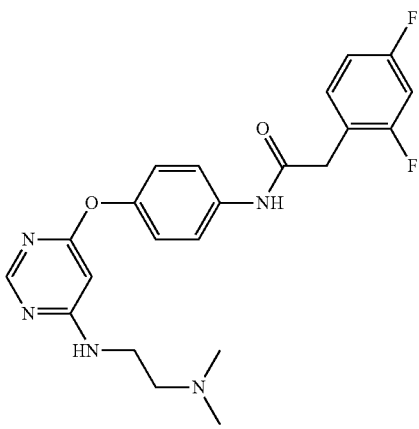 [SMILES: CN(C)CCNc1cc(Oc2ccc(NC(=O)Cc3ccc(F)cc3F)cc2)ncn1]

Synthesis of the compound of Example 78 was accomplished by using procedures similar to that described in Example 1. MS(ESI) m/z (M+1)+: 428.19.

Example 79: 1-[4-(6-amino-pyrimidin-4-yloxy)-phenyl]-3-(4-methyl-3-trifluoromethyl-phenyl)-urea

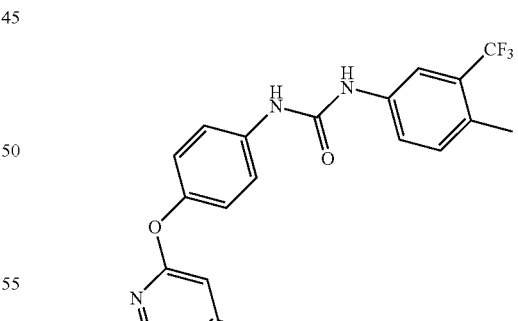

Synthesis of the compound of Example 79 was accomplished by using procedures similar to that described in Example 57. MS(ESI) m/z (M+1)+: 404.14.

Example 80: 1-[4-(6-methylamino-pyrimidin-4-yloxy)-phenyl]-3-(4-methyl-3-trifluoromethyl-phenyl)-urea

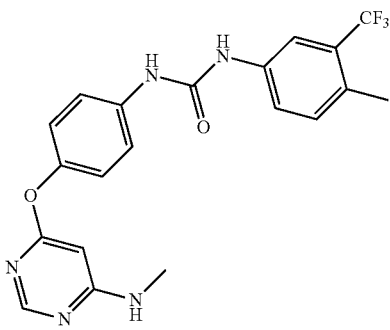 [SMILES: CNc1cc(Oc2ccc(NC(=O)Nc3ccc(C)c(C(F)(F)F)c3)cc2)ncn1]

Synthesis of the compound of Example 80 was accomplished by using procedures similar to that described in Example 57. MS(ESI) m/z (M+1)+: 418.15.

Example 81: 1-[4-(6-benzylamino-pyrimidin-4-yloxy)-phenyl]-3-(4-methyl-3-trifluoromethyl-phenyl)-urea

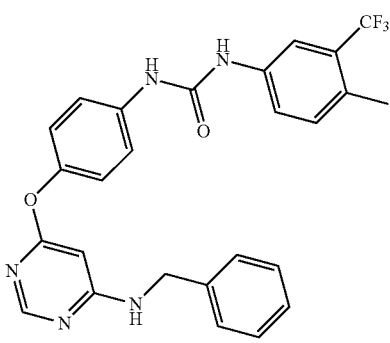 [SMILES: Cc1ccc(NC(=O)Nc2ccc(Oc3cc(NCc4ccccc4)ncn3)cc2)cc1C(F)(F)F]

Synthesis of the compound of Example 81 was accomplished by using procedures similar to that described in Example 57. MS(ESI) m/z (M+1)+: 494.18.

Example 82: N-(6-{4-[3-(4-methyl-3-trifluoromethyl-phenyl)-ureido]-phenoxy}-pyrimidin-4-yl)-acetamide

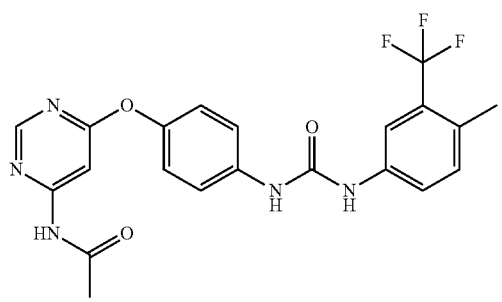 [SMILES: CC(=O)Nc1cc(Oc2ccc(NC(=O)Nc3ccc(C)c(C(F)(F)F)c3)cc2)ncn1]

Synthesis of the compound of Example 82 was accomplished by using procedures similar to that described in Example 57. MS(ESI) m/z (M+1)+: 446.15.

Example 83: 1-(4-(6-(cyclopropaneformamide)pyrimidin-4-yloxy)phenyl)-3-(4-methyl-3-trifluoromethyl-phenyl)urea

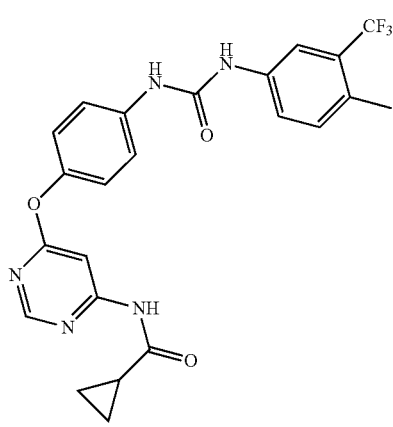 [SMILES: Cc1ccc(NC(=O)Nc2ccc(Oc3cc(NC(=O)C4CC4)ncn3)cc2)cc1C(F)(F)F]

Synthesis of the compound of Example 83 was accomplished by using procedures similar to that described in Example 57. MS(ESI) m/z (M+1)+: 472.16.

Example 84: [2-(6-{4-[3-(4-methyl-3-trifluoromethyl-phenyl)-ureido]-phenoxy}-pyrimidin-4-ylamino)-ethyl]-aminotert-butyl formate

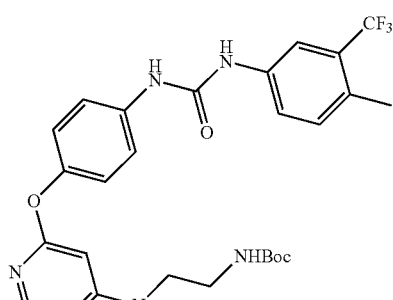

Synthesis of the compound of Example 84 was accomplished by using procedures similar to that described in Example 57. MS(ESI) m/z (M+1)+: 547.23.

Example 85: 1-{4-[6-(2-amino-ethylamino)-pyrimidin-4-yloxy]-phenyl}-3-(4-methyl-3-trifluoromethyl-phenyl)-urea

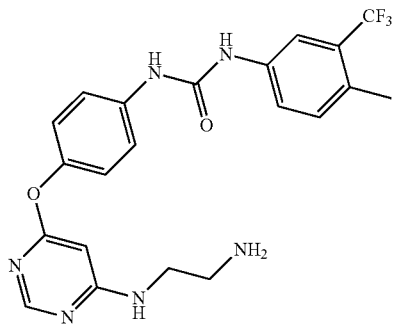 [SMILES: Cc1ccc(NC(=O)Nc2ccc(Oc3cc(NCCN)ncn3)cc2)cc1C(F)(F)F]

Synthesis of the compound of Example 85 was accomplished by using procedures similar to that described in Example 57. MS(ESI) m/z (M+1)+: 447.18.

Example 86: 1-{4-[6-(2-dimethylamino-ethyl-amino)-pyrimidin-4-yloxy]-phenyl}-3-(4-methyl-3-trifluoromethyl-phenyl)-urea

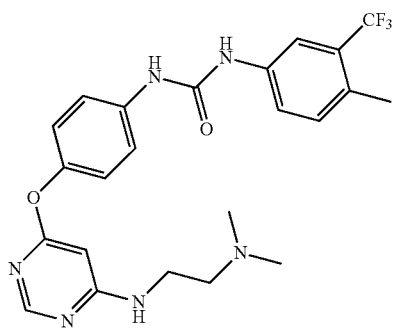 [SMILES: Cc1ccc(NC(=O)Nc2ccc(Oc3cc(NCCN(C)C)ncn3)cc2)cc1C(F)(F)F]

Synthesis of the compound of Example 86 was accomplished by using procedures similar to that described in Example 57. MS(ESI) m/z (M+1)+: 475.21.

Example 87: 1-(4-{6-[(2-hydroxy-ethyl)-methyl-amino]-pyrimidin-4-yloxy}-phenyl)-3-(4-methyl-3-trifluoromethyl-phenyl)-urea

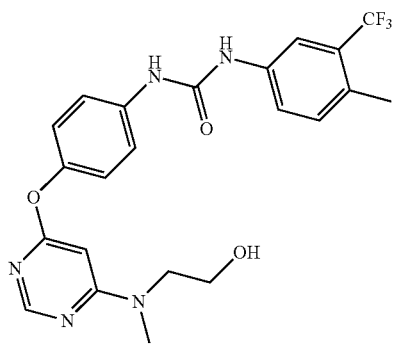 [SMILES: Cc1ccc(NC(=O)Nc2ccc(Oc3cc(N(C)CCO)ncn3)cc2)cc1C(F)(F)F]

Synthesis of the compound of Example 87 was accomplished by using procedures similar to that described in Example 57. MS(ESI) m/z (M+1)+: 462.18.

Example 88: 1-{4-[6-(2-hydroxy-ethylamino)-pyrimidin-4-yloxy]-phenyl}-3-(4-methyl-3-trifluoromethyl-phenyl)-urea

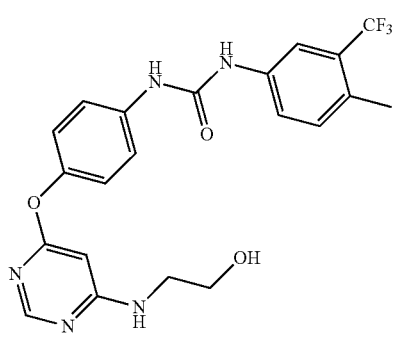 [SMILES: Cc1ccc(NC(=O)Nc2ccc(Oc3cc(NCCO)ncn3)cc2)cc1C(F)(F)F]

Synthesis of the compound of Example 88 was accomplished by using procedures similar to that described in Example 57. MS(ESI) m/z (M+1)+: 448.16.

Example 89: 1-{4-[6-(2-methoxy-ethylamino)-pyrimidin-4-yloxy]-phenyl}-3-(4-methyl-3-trifluoromethyl-phenyl)-urea

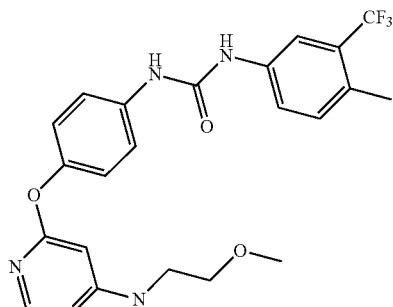

Synthesis of the compound of Example 89 was accomplished by using procedures similar to that described in Example 57. MS(ESI) m/z (M+1)+: 462.18.

Example 90: 1-(4-{6-[methyl-(2-methylamino-ethyl)-amino]-pyrimidin-4-yloxy}-phenyl)-3-(4-methyl-3-trifluoromethyl-phenyl)-urea

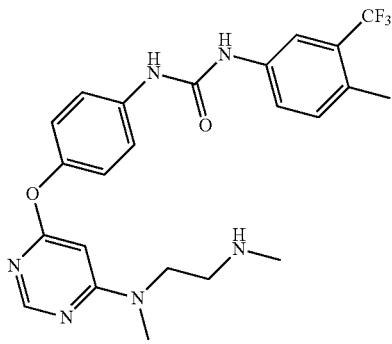 [SMILES: CNCCN(C)c1cc(Oc2ccc(NC(=O)Nc3ccc(C)c(C(F)(F)F)c3)cc2)ncn1]

Synthesis of the compound of Example 90 was accomplished by using procedures similar to that described in Example 57. MS(ESI) m/z (M+1)+: 475.21.

Example 91: 1-(4-{6-[(2-amino-ethyl)-methyl-amino]-pyrimidin-4-yloxy}-phenyl)-3-(4-methyl-3-trifluoromethyl-phenyl)-urea

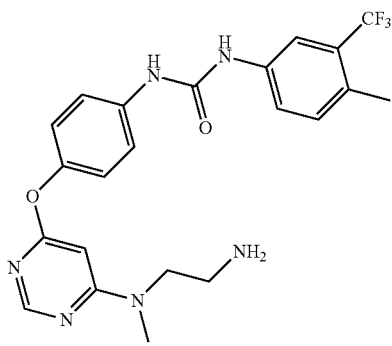 [SMILES: Cc1ccc(NC(=O)Nc2ccc(Oc3cc(N(C)CCN)ncn3)cc2)cc1C(F)(F)F]

Synthesis of the compound of Example 91 was accomplished by using procedures similar to that described in Example 57. MS(ESI) m/z (M+1)+: 461.19.

Example 92: 1-(4-{6-[(2-dimethylamino-ethyl)-methyl-amino]-pyrimidin-4-yloxy}-phenyl)-3-(4-methyl-3-trifluoromethyl-phenyl)-urea

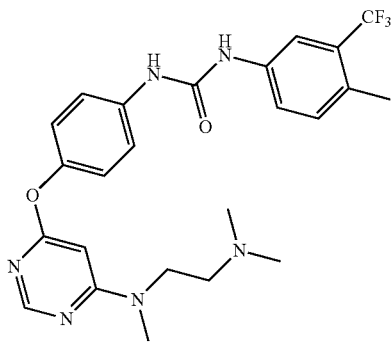 [SMILES: Cc1ccc(NC(=O)Nc2ccc(Oc3cc(N(C)CCN(C)C)ncn3)cc2)cc1C(F)(F)F]

Synthesis of the compound of Example 92 was accomplished by using procedures similar to that described in Example 57. MS(ESI) m/z (M+1)+: 489.22.

Example 93: 1-{4-[6-(3-hydroxy-cyclohexylamino)-pyrimidin-4-yloxy]-phenyl}-3-(4-methyl-3-trifluoromethyl-phenyl)-urea

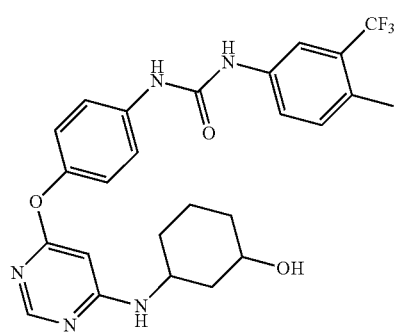 [SMILES: Cc1ccc(NC(=O)Nc2ccc(Oc3cc(NC4CCCC(O)C4)ncn3)cc2)cc1C(F)(F)F]

Synthesis of the compound of Example 93 was accomplished by using procedures similar to that described in Example 57. MS(ESI) m/z (M+1)+: 502.21.

Example 94: 1-{4-[6-(3-amino-cyclohexylamino)-pyrimidin-4-yloxy]-phenyl}-3-(4-methyl-3-trifluoromethyl-phenyl)-urea

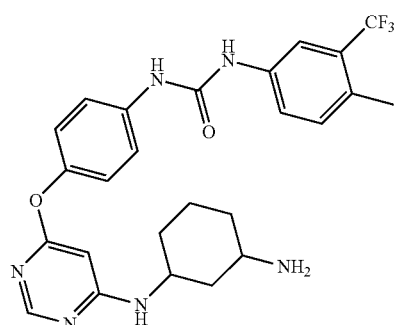

Synthesis of the compound of Example 94 was accomplished by using procedures similar to that described in Example 57. MS(ESI) m/z (M+1)+: 501.22.

Example 95: (S)-3-methyl-2-((6-(4-(3-(4-methyl-3-(trifluoromethyl)phenyl)ureido)phenoxy)pyrimidin-4-yl)amino)butyramide

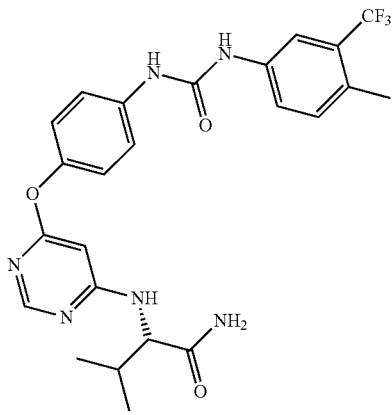

Synthesis of the compound of Example 95 was accomplished by using procedures similar to that described in Example 57. MS(ESI) m/z (M+1)+: 503.20.

Example 96: (R)-2-((6-(4-(3-(4-methyl-3-(trifluoromethyl)phenyl)ureido)phenoxy)pyrimidin-4-yl)amino)butyramide

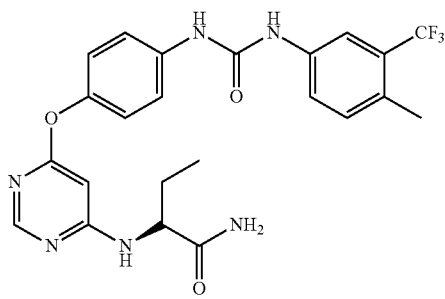

Synthesis of the compound of Example 96 was accomplished by using procedures similar to that described in Example 57. MS(ESI) m/z (M+1)+: 489.19.

Example 97: (R)-2-((6-(4-(3-(4-methyl-3-(trifluoromethyl)phenyl)ureido)phenoxy)pyrimidin-4-yl)amino)propionamide

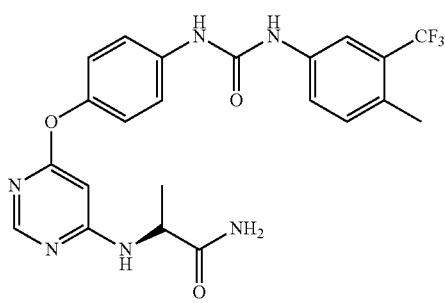

Synthesis of the compound of Example 97 was accomplished by using procedures similar to that described in Example 57. MS(ESI) m/z (M+1)+: 475.17.

Example 98: 3-methyl-4-(6-{4-[3-(4-methyl-3-trifluoromethyl-phenyl)-ureido]-phenoxy}-pyrimidin-4-yl)-piperazin-1-tert-butyl Formate

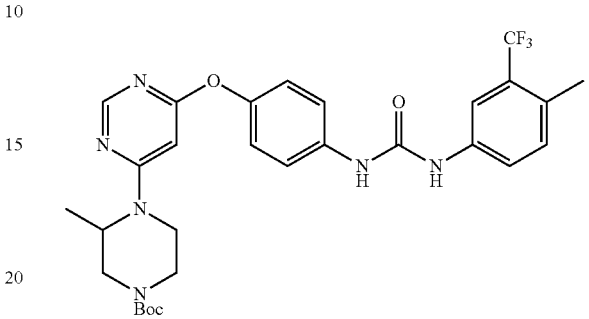

Synthesis of the compound of Example 98 was accomplished by using procedures similar to that described in Example 57. MS(ESI) m/z (M+1)+: 587.26.

Example 99: 4-(6-{4-[3-(4-methyl-3-trifluoromethyl-phenyl)-ureido]-phenoxy}-pyrimidin-4-ylamino)-piperidin-1-tert-butyl Formate

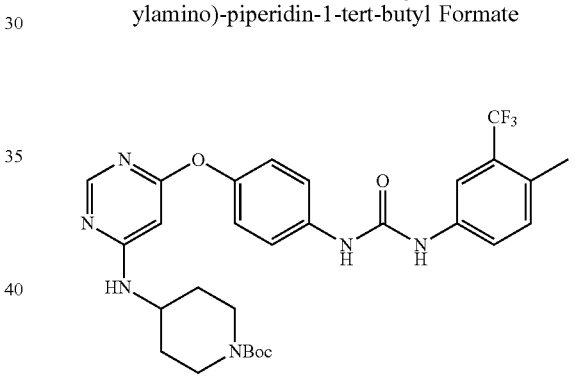

Synthesis of the compound of Example 99 was accomplished by using procedures similar to that described in Example 57. MS(ESI) m/z (M+1)+: 587.26.

Example 100: (R)-3-methyl-4-(6-(4-(3-(4-methyl-3-(trifluoromethyl)phenyl)ureido)phenoxy)pyrimidin-4-yl)piperazin-1-tert-butyl Formate

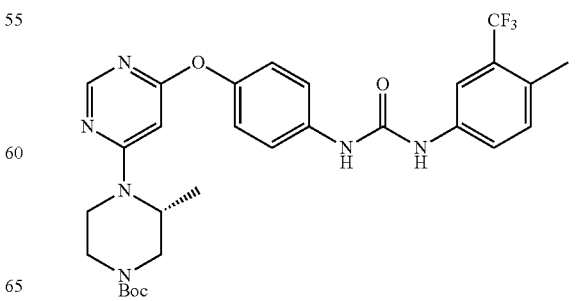

Synthesis of the compound of Example 100 was accomplished by using procedures similar to that described in Example 57. MS(ESI) m/z (M+1)+: 587.26.

Example 101: (S)-3-methyl-4-(6-(4-(3-(4-methyl-3-(trifluoromethyl)phenyl)ureido)phenoxy)pyrimidin-4-yl)piperazin-1-tert-butyl Formate

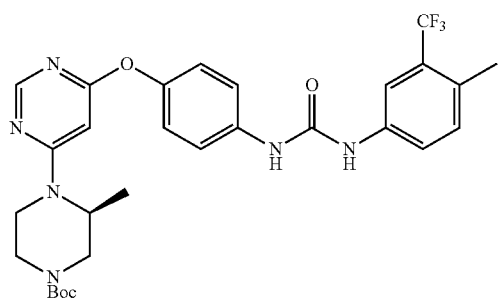 [SMILES: Cc1ccc(NC(=O)Nc2ccc(Oc3cc(N4CCN(C(=O)OC(C)(C)C)C[C@@H]4C)ncn3)cc2)cc1C(F)(F)F]

Synthesis of the compound of Example 101 was accomplished by using procedures similar to that described in Example 57. MS(ESI) m/z (M+1)+: 587.26.

Example 102: (R)-2-methyl-4-(6-(4-(3-(4-methyl-3-(trifluoromethyl)phenyl)ureido)phenoxy)pyrimidin-4-yl)piperazin-1-tert-butyl Formate

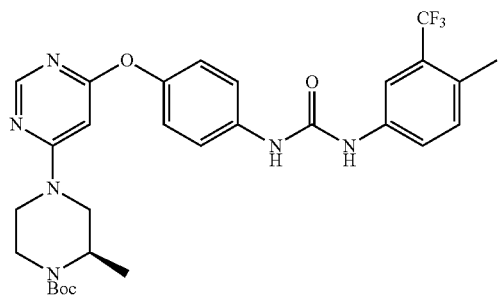 [SMILES: Cc1ccc(NC(=O)Nc2ccc(Oc3cc(N4CCN(C(=O)OC(C)(C)C)[C@H](C)C4)ncn3)cc2)cc1C(F)(F)F]

Synthesis of the compound of Example 102 was accomplished by using procedures similar to that described in Example 57. MS(ESI) m/z (M+1)+: 587.26.

Example 103: 1-(4-methyl-3-trifluoromethyl-phenyl)-3-{4-[6-(piperidin-4-ylamino)-pyrimidin-4-yloxy]-phenyl}-urea

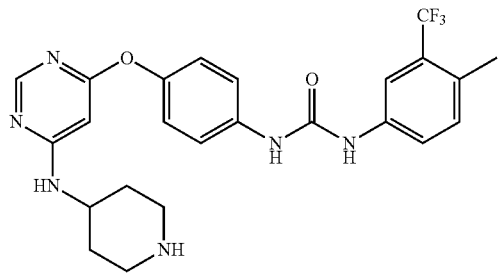 [SMILES: Cc1ccc(NC(=O)Nc2ccc(Oc3cc(NC4CCNCC4)ncn3)cc2)cc1C(F)(F)F]

Synthesis of the compound of Example 103 was accomplished by using procedures similar to that described in Example 57. MS(ESI) m/z (M+1)+: 487.21.

Example 104: 1-{4-[6-(2-methyl-piperazin-1-yl)-pyrimidin-4-yloxy]-phenyl}-3-(4-methyl-3-trifluoromethyl-phenyl)-urea

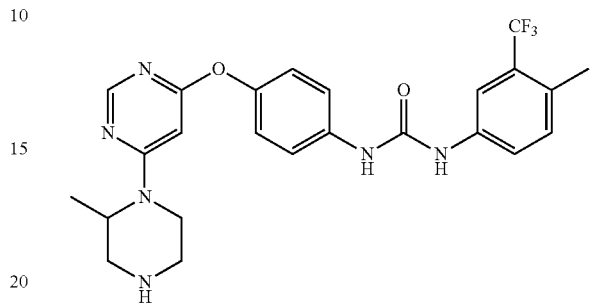

Synthesis of the compound of Example 103 was accomplished by using procedures similar to that described in Example 57. MS(ESI) m/z (M+1)+: 487.21.

Example 105: (R)-1-(4-methyl-3-(trifluoromethyl)phenyl)-3-(4-((6-(2-methylpiperazin-1-yl)pyrimidin-4-yl)oxy)phenyl)urea

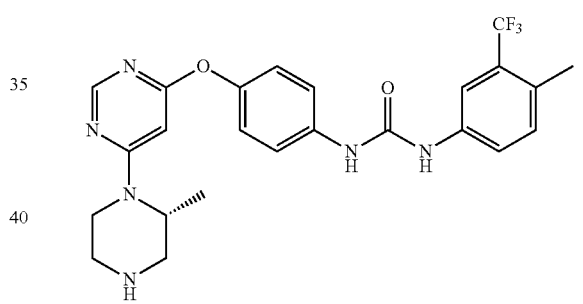

Synthesis of the compound of Example 105 was accomplished by using procedures similar to that described in Example 57. MS(ESI) m/z (M+1)+: 487.21.

Example 106: (R)-1-(4-methyl-3-(trifluoromethyl)phenyl)-3-(4-((6-(3-methylpiperazin-1-yl)pyrimidin-4-yl)oxy)phenyl)urea

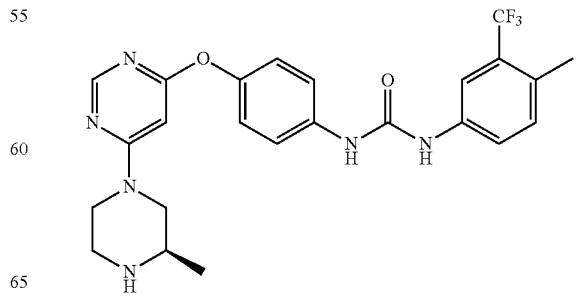

Synthesis of the compound of Example 106 was accomplished by using procedures similar to that described in Example 57. MS(ESI) m/z (M+1)+: 487.21.

Example 107: (S)-1-(4-methyl-3-(trifluoromethyl)phenyl)-3-(4-((6-(2-methylpiperazin-1-yl)pyrimidin-4-yl)oxy)phenyl)urea

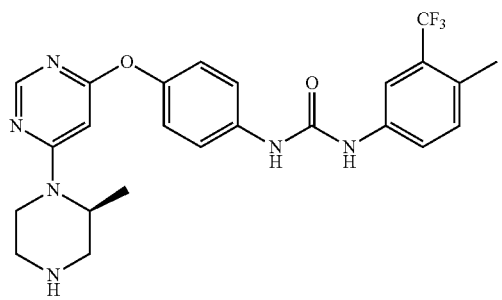 [SMILES: Cc1ccc(NC(=O)Nc2ccc(Oc3cc(N4CCNC[C@@H]4C)ncn3)cc2)cc1C(F)(F)F]

Synthesis of the compound of Example 107 was accomplished by using procedures similar to that described in Example 57. MS(ESI) m/z (M+1)+: 487.21.

Example 108: 1-{4-[6-(2-amino-ethylamino)-pyrimidin-4-yloxy]-phenyl}-3-[4-(4-methyl-piperazin-1-ylmethyl)-3-trifluoromethyl-phenyl]-urea

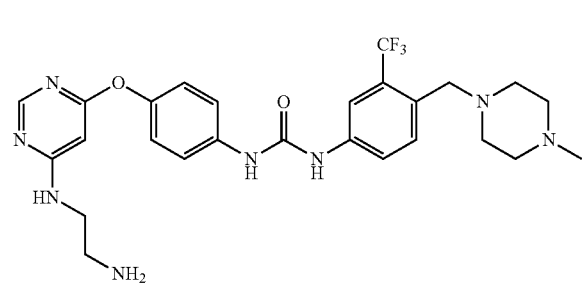 [SMILES: CN1CCN(Cc2ccc(NC(=O)Nc3ccc(Oc4cc(NCCN)ncn4)cc3)cc2C(F)(F)F)CC1]

Synthesis of the compound of Example 108 was accomplished by using procedures similar to that described in Example 57. MS(ESI) m/z (M+1)+: 545.26.

Example 109: 1-{4-[6-(2-amino-ethylamino)-pyrimidin-4-yloxy]-phenyl}-3-[4-(4-ethyl-piperazin-1-ylmethyl)-3-trifluoromethyl-phenyl]-urea

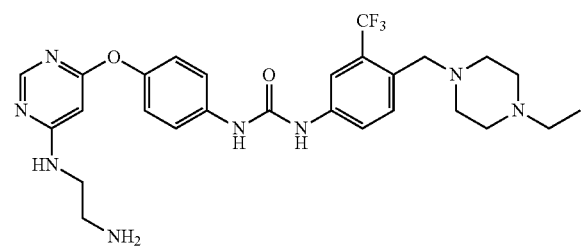 [SMILES: CCN1CCN(Cc2ccc(NC(=O)Nc3ccc(Oc4cc(NCCN)ncn4)cc3)cc2C(F)(F)F)CC1]

Synthesis of the compound of Example 109 was accomplished by using procedures similar to that described in Example 57. MS(ESI) m/z (M+1)+: 559.28.

Example 110: (S)-3-(hydroxymethyl)-4-(6-(4-(3-(4-methyl-3-(trifluoromethyl)phenyl)ureido)phenoxy)pyrimidin-4-yl)piperazin-1-tert-butyl Formate

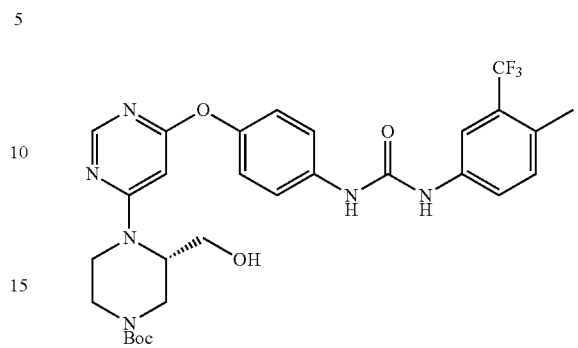

Synthesis of the compound of Example 110 was accomplished by using procedures similar to that described in Example 57. MS(ESI) m/z (M+1)+: 603.26.

Example 111: (R)-3-ethyl-4-(6-(4-(3-(4-methyl-3-(trifluoromethyl)phenyl)ureido)phenoxy)pyrimidin-4-yl)piperazin-1-tert-butyl formate

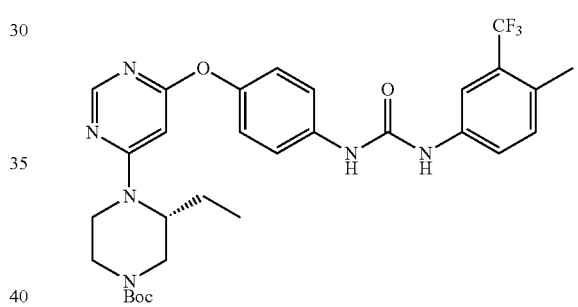

Synthesis of the compound of Example 111 was accomplished by using procedures similar to that described in Example 57. MS(ESI) m/z (M+1)+: 601.28.

Example 112: (R)-(2-((6-(4-(3-(4-methyl-3-(trifluoromethyl)phenyl)ureido)phenoxy)pyrimidin-4-yl)amino)propyl)aminotert-butyl Formate

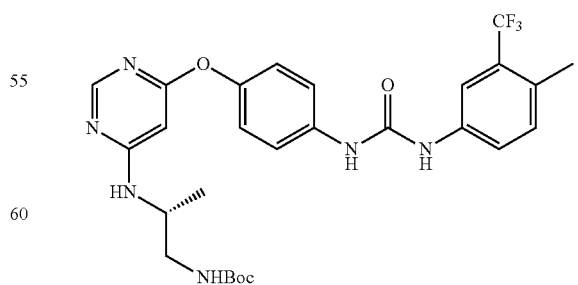

Synthesis of the compound of Example 112 was accomplished by using procedures similar to that described in Example 57. MS(ESI) m/z (M+1)+: 561.25.

Example 113: (R)-1-(4-((6-((1-aminoprop-2-yl)amino)pyrimidin-4-yl)oxy)phenyl)-3-(4-methyl-3-(trifluoromethyl)phenyl)urea

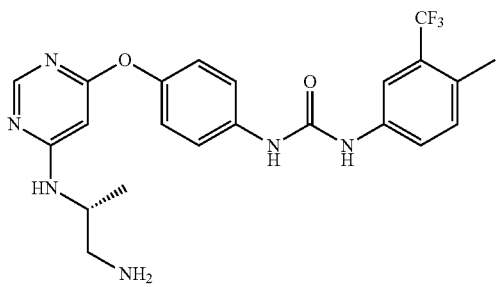 [SMILES: Cc1ccc(NC(=O)Nc2ccc(Oc3cc(N[C@H](C)CN)ncn3)cc2)cc1C(F)(F)F]

Synthesis of the compound of Example 113 was accomplished by using procedures similar to that described in Example 57. MS(ESI) m/z (M+1)+: 461.19.

Example 114: (R)-1-(4-methyl-3-(trifluoromethyl)phenyl)-3-(4-((6-(3-methylmorpholino)pyrimidin-4-yl)oxy)phenyl)urea

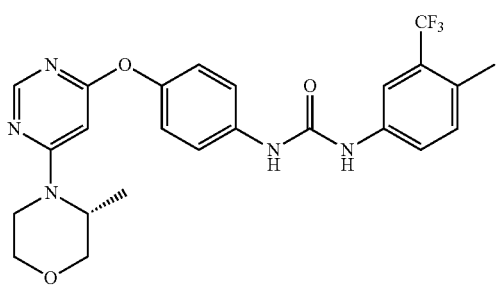 [SMILES: Cc1ccc(NC(=O)Nc2ccc(Oc3cc(N4CCOC[C@H]4C)ncn3)cc2)cc1C(F)(F)F]

Synthesis of the compound of Example 114 was accomplished by using procedures similar to that described in Example 57. MS(ESI) m/z (M+1)+: 488.19.

Example 115: (R)-1-(4-((6-(4-(3,3-dimethylbutyryl)-2-methylpiperazin-1-yl)pyrimidin-4-yl)oxy)phenyl)-3-(4-methyl-3-(trifluoromethyl)phenyl)urea

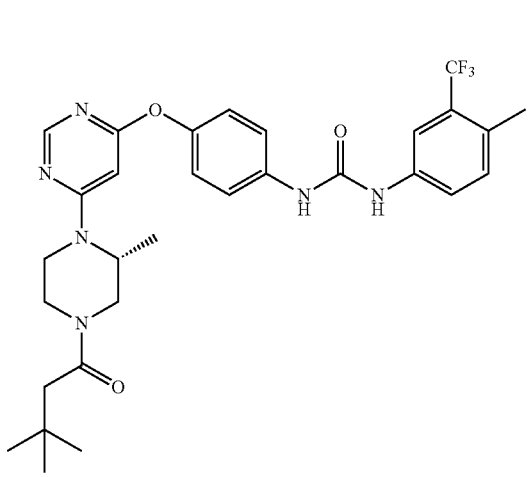 [SMILES: Cc1ccc(NC(=O)Nc2ccc(Oc3cc(N4CCN(C(=O)CC(C)(C)C)C[C@H]4C)ncn3)cc2)cc1C(F)(F)F]

Synthesis of the compound of Example 115 was accomplished by using procedures similar to that described in Example 57. MS(ESI) m/z (M+1)+: 585.28.

Example 116: (R)-1-(4-methyl-3-(trifluoromethyl)phenyl)-3-(4-((6-(2-methyl-4-propionylpiperazin-1-yl)pyrimidin-4-yl)oxy)phenyl)urea

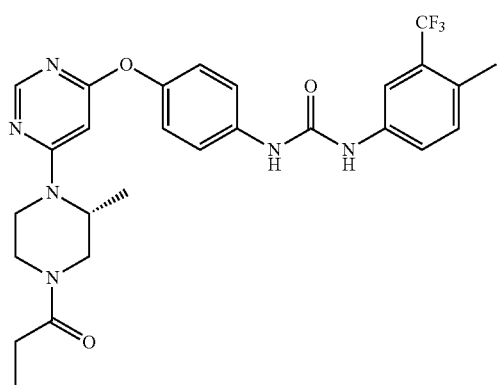 [SMILES: CCC(=O)N1CCN(c2cc(Oc3ccc(NC(=O)Nc4ccc(C)c(C(F)(F)F)c4)cc3)ncn2)[C@H](C)C1]

Synthesis of the compound of Example 116 was accomplished by using procedures similar to that described in Example 57. MS(ESI) m/z (M+1)+: 543.24.

Example 117: (R)-1-(4-((6-(4-acetyl-2-methylpiperazin-1-yl)pyrimidin-4-yl)oxy)phenyl)-3-(4-methyl-3-(trifluoromethyl)phenyl)urea

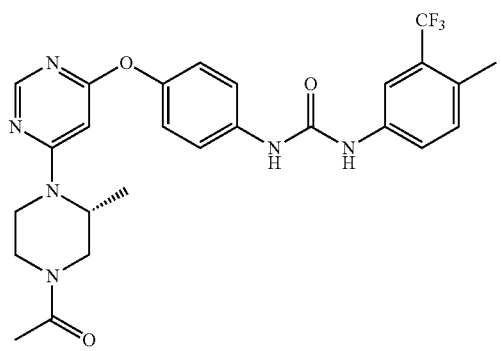 [SMILES: CC(=O)N1CCN(c2cc(Oc3ccc(NC(=O)Nc4ccc(C)c(C(F)(F)F)c4)cc3)ncn2)[C@H](C)C1]

Synthesis of the compound of Example 117 was accomplished by using procedures similar to that described in Example 57. MS(ESI) m/z (M+1)+: 529.22.

Example 118: (R)-1-(4-((6-(4-butyryl-2-methylpiperazin-1-yl)pyrimidin-4-yl)oxy)phenyl)-3-(4-methyl-3-(trifluoromethyl)phenyl)urea

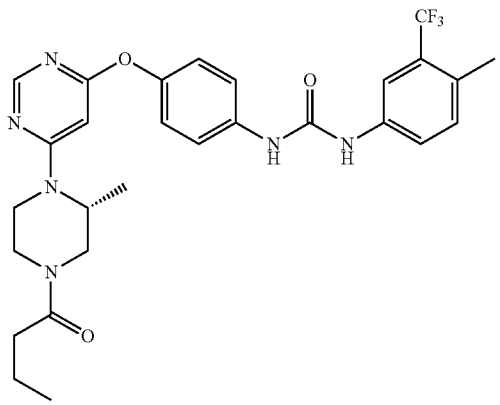 [SMILES: CCCC(=O)N1CCN(c2cc(Oc3ccc(NC(=O)Nc4ccc(C)c(C(F)(F)F)c4)cc3)ncn2)[C@H](C)C1]

Synthesis of the compound of Example 118 was accomplished by using procedures similar to that described in Example 57. MS(ESI) m/z (M+1)+: 557.25.

Example 119: (R)-1-(4-((6-(4-(2,2-dimethylbutyryl)-2-methylpiperazin-1-yl)pyrimidin-4-yl)oxy)phenyl)-3-(4-methyl-3-(trifluoromethyl)phenyl)urea

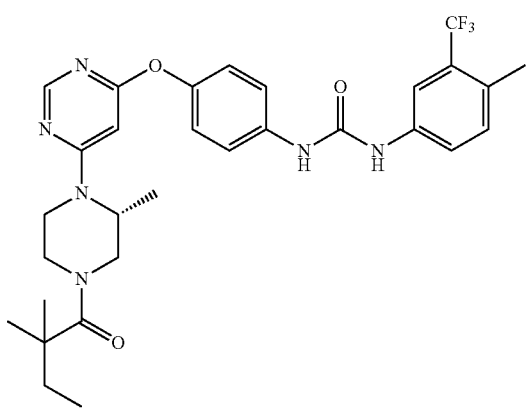 [SMILES: CCC(C)(C)C(=O)N1CCN(c2cc(Oc3ccc(NC(=O)Nc4ccc(C)c(C(F)(F)F)c4)cc3)ncn2)[C@H](C)C1]

Synthesis of the compound of Example 119 was accomplished by using procedures similar to that described in Example 57. MS(ESI) m/z (M+1)+: 585.28.

Example 120: (S)-1-(4-((6-(2-(hydroxymethyl)piperazin-1-yl)pyrimidin-4-yl)oxy)phenyl)-3-(4-methyl-3-(trifluoromethyl)phenyl)urea

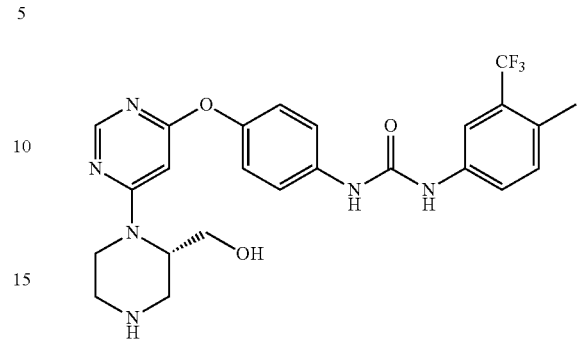

Synthesis of the compound of Example 120 was accomplished by using procedures similar to that described in Example 57. MS(ESI) m/z (M+1)+: 503.20.

Example 121: (R)-1-(4-((6-(2-ethylpiperazin-1-yl)pyrimidin-4-yl)oxy)phenyl)-3-(4-methyl-3-(trifluoromethyl)phenyl)urea

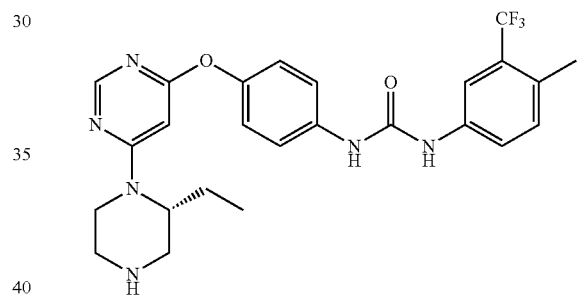

Synthesis of the compound of Example 121 was accomplished by using procedures similar to that described in Example 57. MS(ESI) m/z (M+1)+: 501.22.

Example 122: 1-(4-methyl-3-trifluoromethyl-phenyl)-3-{4-[6-(2-pyrrolidin-1-yl-ethylamino)-pyrimidin-4-yloxy]-phenyl}-urea

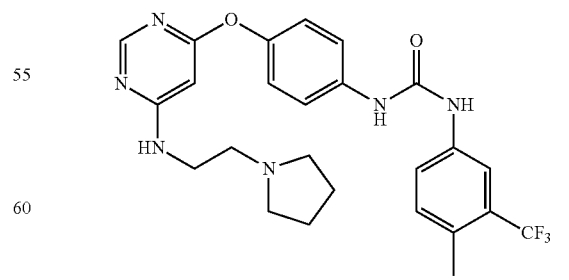

Synthesis of the compound of Example 122 was accomplished by using procedures similar to that described in Example 57. MS(ESI) m/z (M+1)+: 501.22.

Example 123: 1-(4-methyl-3-trifluoromethyl-phenyl)-3-(4-{6-[(thiophene-2-ylmethyl)-amino]-pyrimidin-4-yloxy}-phenyl)-urea

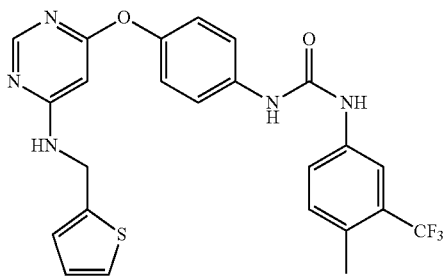 [SMILES: Cc1ccc(NC(=O)Nc2ccc(Oc3cc(NCc4cccs4)ncn3)cc2)cc1C(F)(F)F]

Synthesis of the compound of Example 123 was accomplished by using procedures similar to that described in Example 57. MS(ESI) m/z (M+1)+: 500.14.

Example 124: [2-(6-{4-[3-(4-methyl-3-trifluoromethyl-phenyl)-ureido]-cyclohexyloxy}-pyrimidin-4-ylamino)-ethyl]-aminotert-butyl Formate

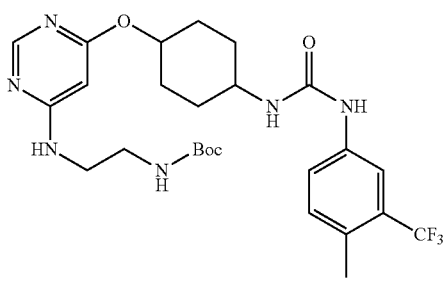

Synthesis of the compound of Example 124 was accomplished by using procedures similar to that described in Example 40. MS(ESI) m/z (M+1)+: 553.28.

Example 125: 2-(6-{4-[3-(4-methyl-3-trifluoromethyl-phenyl)-ureido]-phenoxy}-pyrimidin-4-ylamino)-acetamide

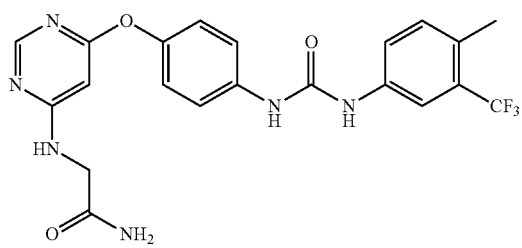 [SMILES: Cc1ccc(NC(=O)Nc2ccc(Oc3cc(NCC(N)=O)ncn3)cc2)cc1C(F)(F)F]

Synthesis of the compound of Example 125 was accomplished by using procedures similar to that described in Example 57. MS(ESI) m/z (M+1)+: 461.16.

Example 126: (6-(4-(3-(4-methyl-3-(trifluoromethyl)phenyl)ureido)phenoxy)pyrimidin-4-yl)-L-aminopropionic Acid

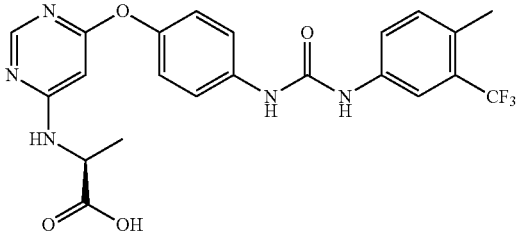 [SMILES: Cc1ccc(NC(=O)Nc2ccc(Oc3cc(N[C@@H](C)C(=O)O)ncn3)cc2)cc1C(F)(F)F]

Synthesis of the compound of Example 126 was accomplished by using procedures similar to that described in Example 57. MS(ESI) m/z (M+1)+: 476.16.

Example 127: (S)—N-(tert-butyl)-2-((6-(4-(3-(4-methyl-3-(trifluoromethyl)phenyl)ureido)phenoxy)pyrimidin-4-yl)amino)propionamide

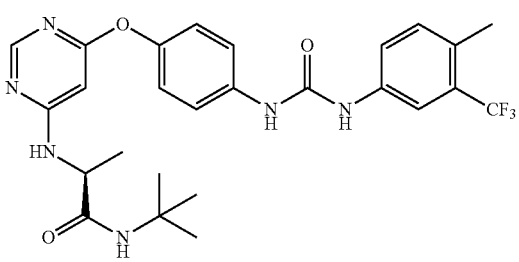 [SMILES: Cc1ccc(NC(=O)Nc2ccc(Oc3cc(N[C@@H](C)C(=O)NC(C)(C)C)ncn3)cc2)cc1C(F)(F)F]

Synthesis of the compound of Example 127 was accomplished by using procedures similar to that described in Example 57. MS(ESI) m/z (M+1)+: 531.24.

Example 128: 1-{4-[6-(2-amino-ethylamino)-pyrimidin-4-yloxy]-cyclohexyl}-3-(4-methyl-3-trifluoromethyl-phenyl)-urea

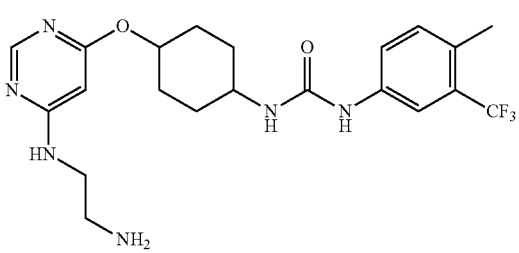 [SMILES: Cc1ccc(NC(=O)NC2CCC(Oc3cc(NCCN)ncn3)CC2)cc1C(F)(F)F]

Synthesis of the compound of Example 128 was accomplished by using procedures similar to that described in Example 40. MS(ESI) m/z (M+1)+: 453.22.

Example 129: 1-{4-[6-(2-hydroxy-ethylamino)-pyrimidin-4-yloxy]-phenyl}-3-[3-(4-methyl-imidazol-1-yl)-5-trifluoromethyl-phenyl]-urea

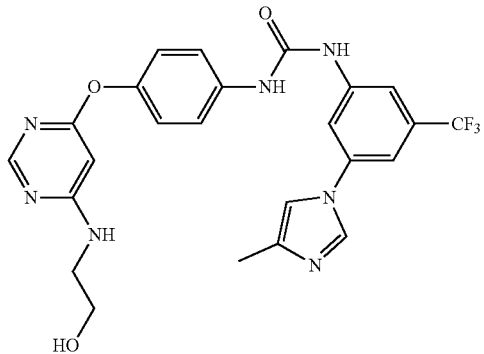 [SMILES: Cc1cn(-c2cc(NC(=O)Nc3ccc(Oc4cc(NCCO)ncn4)cc3)cc(C(F)(F)F)c2)cn1]

Synthesis of the compound of Example 129 was accomplished by using procedures similar to that described in Example 57. MS(ESI) m/z (M+1)+: 514.18.

Example 130: N-[6-(4-{3-[4-(4-methyl-piperazin-1-ylmethyl)-3-trifluoromethyl-phenyl]-ureido}-phenoxy)-pyrimidin-4-yl]-acetamide

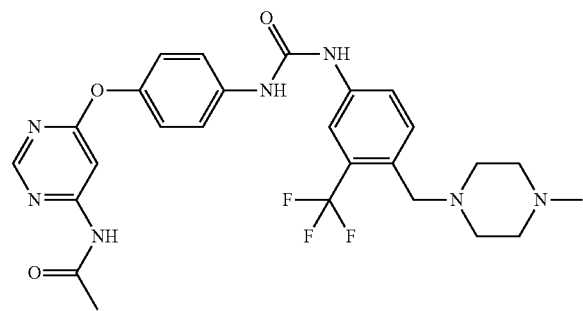 [SMILES: CC(=O)Nc1cc(Oc2ccc(NC(=O)Nc3ccc(CN4CCN(C)CC4)c(C(F)(F)F)c3)cc2)ncn1]

Synthesis of the compound of Example 130 was accomplished by using procedures similar to that described in Example 57. MS(ESI) m/z (M+1)+: 544.23.

Example 131: N-[6-(4-{3-[3-(4-methyl-imidazol-1-yl)-5-trifluoromethyl-phenyl]-ureido}-phenoxy)-pyrimidin-4-yl]-acetamide

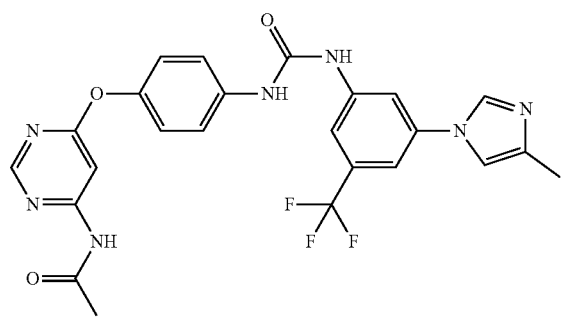 [SMILES: CC(=O)Nc1cc(Oc2ccc(NC(=O)Nc3cc(-n4cnc(C)c4)cc(C(F)(F)F)c3)cc2)ncn1]

Synthesis of the compound of Example 131 was accomplished by using procedures similar to that described in Example 57. MS(ESI) m/z (M+1)+: 512.17.

Example 132: N-[6-(4-{3-[4-(4-ethyl-piperazin-1-ylmethyl)-3-trifluoromethyl-phenyl]-ureido}-phenoxy)-pyrimidin-4-yl]-acetamide

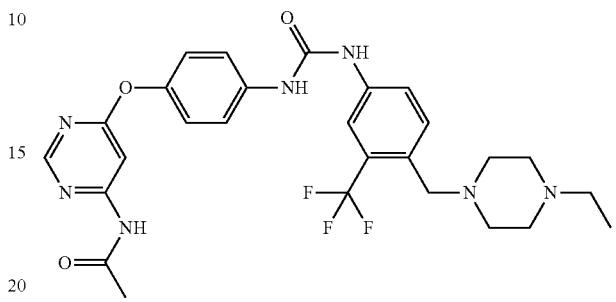

Synthesis of the compound of Example 132 was accomplished by using procedures similar to that described in Example 57. MS(ESI) m/z (M+1)+: 558.25.

Example 133: N-[4-(6-acetylamino-pyrimidin-4-yloxy)-phenyl]-2-(4-methyl-3-trifluoromethyl-phenyl)-acetamide

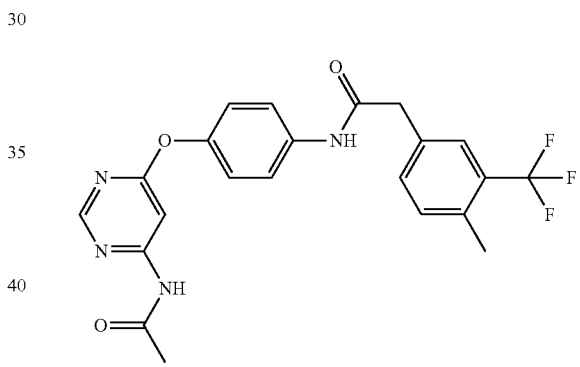

Synthesis of the compound of Example 133 was accomplished by using procedures similar to that described in Example 1. MS(ESI) m/z (M+1)+: 445.15.

Example 134: N-[4-(6-acetylamino-pyrimidin-4-yloxy)-phenyl]-2-(4-chloro-3-trifluoromethyl-phenyl)-acetamide

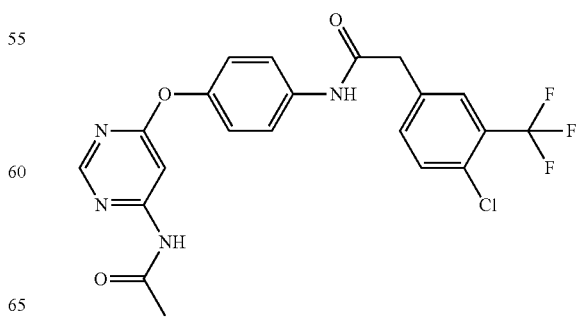

Synthesis of the compound of Example 134 was accomplished by using procedures similar to that described in Example 1. MS(ESI) m/z (M+1)+: 465.10.

Example 135: N-[4-(6-acetylamino-pyrimidin-4-yloxy)-phenyl]-2-(2-trifluoromethyl-phenyl)-acetamide

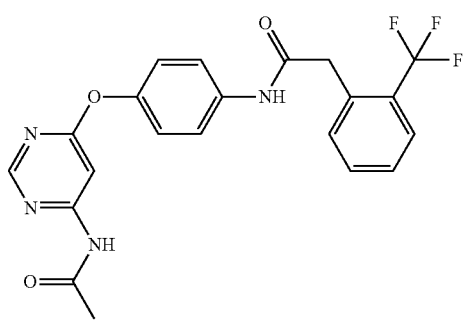 [SMILES: CC(=O)Nc1cc(Oc2ccc(NC(=O)Cc3ccccc3C(F)(F)F)cc2)ncn1]

Synthesis of the compound of Example 135 was accomplished by using procedures similar to that described in Example 1. MS(ESI) m/z (M+1)+: 431.14.

Example 136: N-[4-(6-acetylamino-pyrimidin-4-yloxy)-phenyl]-2-(4-trifluoromethyl-phenyl)-acetamide

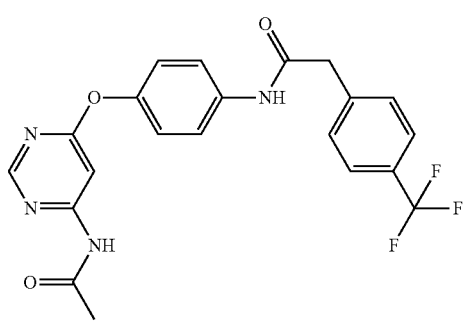 [SMILES: CC(=O)Nc1cc(Oc2ccc(NC(=O)Cc3ccc(C(F)(F)F)cc3)cc2)ncn1]

Synthesis of the compound of Example 136 was accomplished by using procedures similar to that described in Example 1. MS(ESI) m/z (M+1)+: 431.14.

Example 137: 2-(4-((6-((2-aminoethyl)amino)pyrimidin-4-yl)oxy)phenyl)-N-(4-methyl-3-(trifluoromethyl)phenyl)acetamide

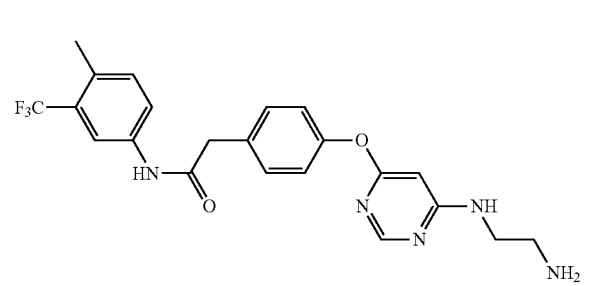 [SMILES: Cc1ccc(NC(=O)Cc2ccc(Oc3cc(NCCN)ncn3)cc2)cc1C(F)(F)F]

Synthesis of the compound of Example 137 was accomplished by using procedures similar to that described in Example 32. MS(ESI) m/z (M+1)+: 446.18.

Example 138: 2-{4-[6-(2-amino-ethylamino)-pyrimidin-4-ylamino]-phenyl}-N-(4-methyl-3-trifluoromethyl-phenyl)-acetamide

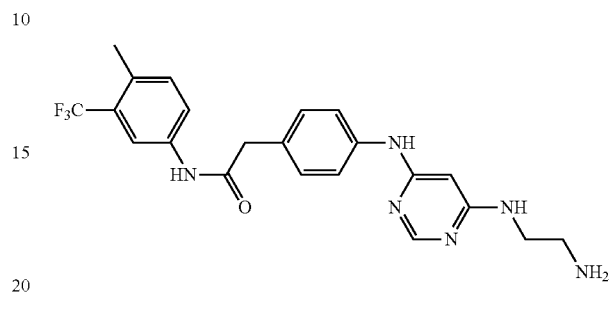

Synthesis of the compound of Example 138 was accomplished by using procedures similar to that described in Example 32. MS(ESI) m/z (M+1)+: 445.20.

Example 139: N-[2-(6-{4-[(4-methyl-3-trifluoromethyl-phenylcarbamoyl)-methyl]-phenylamino}-pyrimidin-4-ylamino)-ethyl]-propanamide

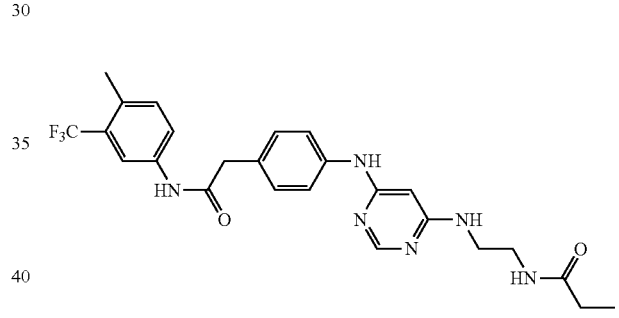

Synthesis of the compound of Example 139 was accomplished by using procedures similar to that described in Example 32. MS(ESI) m/z (M+1)+: 501.21.

Example 140: N-[2-(6-{4-[(4-methyl-3-trifluoromethyl-phenylcarbamoyl)-methyl]-phenylamino}-pyrimidin-4-ylamino)-ethyl]-acrylamide

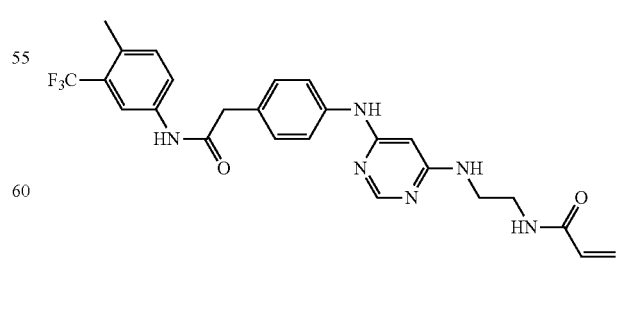

Synthesis of the compound of Example 140 was accomplished by using procedures similar to that described in Example 32. MS(ESI) m/z (M+1)+: 499.21.

Example 141: 1-{4-[6-(4-methoxy-benzylamino)-pyrimidin-4-yloxy]-phenyl}-3-(4-methyl-3-trifluoromethyl-phenyl)-urea

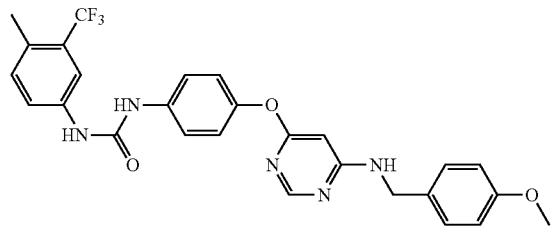 [SMILES: COc1ccc(CNc2cc(Oc3ccc(NC(=O)Nc4ccc(C)c(C(F)(F)F)c4)cc3)ncn2)cc1]

Synthesis of the compound of Example 141 was accomplished by using procedures similar to that described in Example 57. MS(ESI) m/z (M+1)+: 524.19.

Example 142: 2-(6-{4-[3-(4-methyl-3-trifluoromethyl-phenyl)-ureido]-phenoxy}-pyrimidin-4-ylamino)-acetamide

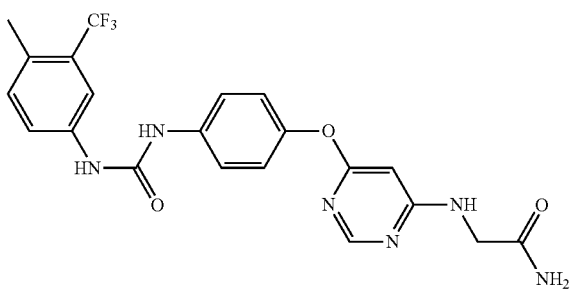 [SMILES: Cc1ccc(NC(=O)Nc2ccc(Oc3cc(NCC(N)=O)ncn3)cc2)cc1C(F)(F)F]

Synthesis of the compound of Example 142 was accomplished by using procedures similar to that described in Example 57. MS(ESI) m/z (M+1)+: 461.16.

Example 143: 1-(4-{6-[(furan-2-ylmethyl)-amino]-pyrimidin-4-yloxy}-phenyl)-3-(4-methyl-3-trifluoromethyl-phenyl)-urea

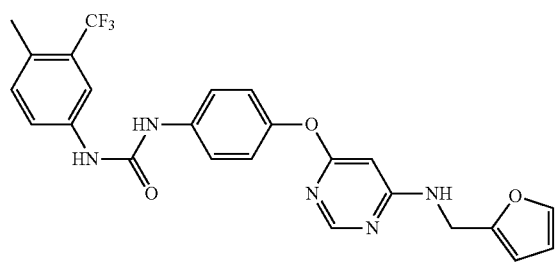 [SMILES: Cc1ccc(NC(=O)Nc2ccc(Oc3cc(NCc4ccco4)ncn3)cc2)cc1C(F)(F)F]

Synthesis of the compound of Example 143 was accomplished by using procedures similar to that described in Example 57. MS(ESI) m/z (M+1)+: 484.16.

Example 144: 1-{4-[6-(4-hydroxy-cyclohexylamino)-pyrimidin-4-yloxy]-phenyl}-3-(4-methyl-3-trifluoromethyl-phenyl)-urea

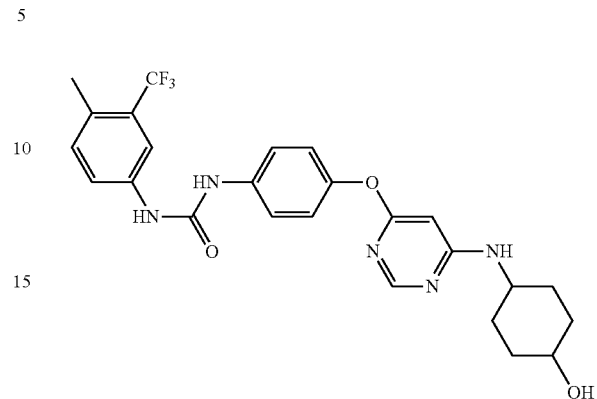

Synthesis of the compound of Example 144 was accomplished by using procedures similar to that described in Example 57. MS(ESI) m/z (M+1)+: 502.21.

Example 145: 1-{4-[6-(4-ethyl-piperazin-1-yl)-pyrimidin-4-yloxy]-phenyl}-3-(4-methyl-3-trifluoromethyl-phenyl)-urea

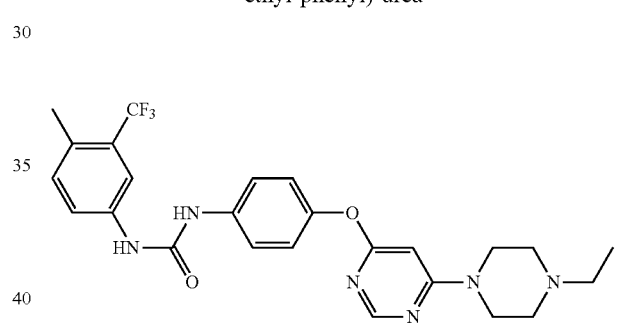

Synthesis of the compound of Example 145 was accomplished by using procedures similar to that described in Example 57. MS(ESI) m/z (M+1)+: 501.22.

Example 146: 1-{4-[6-(4-methyl-piperazin-1-yl)-pyrimidin-4-yloxy]-phenyl}-3-(4-methyl-2-trifluromethyl-phenyl)-urea

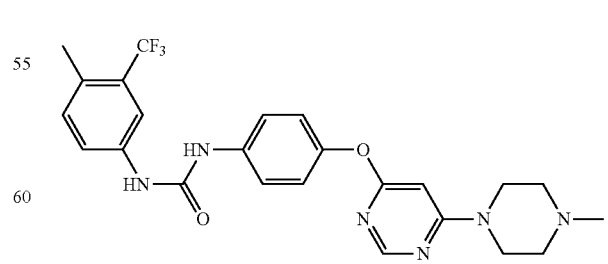

Synthesis of the compound of Example 146 was accomplished by using procedures similar to that described in Example 57. MS(ESI) m/z (M+1)+: 487.21.

Example 147: 1-(4-methyl-3-trifluoromethyl-phenyl)-3-{4-[6-(tetrahydro-pyran-4-ylamino)-pyrimidin-4-yloxy]-phenyl}-urea

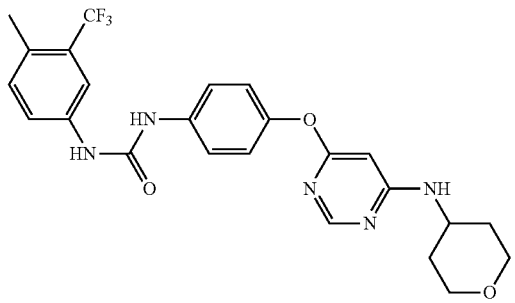 [SMILES: Cc1ccc(NC(=O)Nc2ccc(Oc3cc(NC4CCOCC4)ncn3)cc2)cc1C(F)(F)F]

Synthesis of the compound of Example 147 was accomplished by using procedures similar to that described in Example 57. MS(ESI) m/z (M+1)+: 488.19.

Example 148: 1-(4-{6-[4-(2-methoxy-ethyl)-piperazin-1-yl]-pyrimidin-4-yloxy}-phenyl)-3-(4-methyl-3-trifluoromethyl-phenyl)-urea

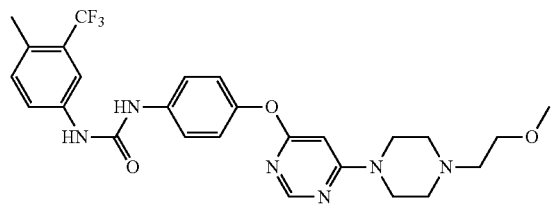 [SMILES: COCCN1CCN(c2cc(Oc3ccc(NC(=O)Nc4ccc(C)c(C(F)(F)F)c4)cc3)ncn2)CC1]

Synthesis of the compound of Example 148 was accomplished by using procedures similar to that described in Example 57. MS(ESI) m/z (M+1)+: 531.24.

Example 149: 1-{4-[6-(4-acetylpiperazin-1-yl)-pyrimidin-4-yloxy]-phenyl}-3-(4-methyl-3-trifluoromethyl-phenyl)-urea

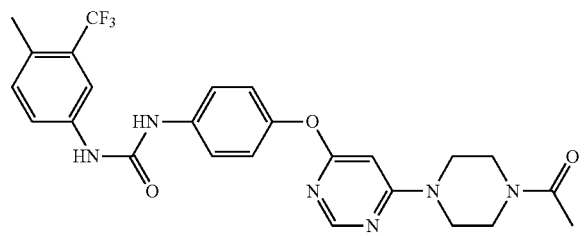

Synthesis of the compound of Example 149 was accomplished by using procedures similar to that described in Example 57. MS(ESI) m/z (M+1)+: 514.20.

Example 150: 1-{4-[6-(4-mesyl-piperazin-1-yl)-pyrimidin-4-yloxy]-phenyl}-3-(4-methyl-3-trifluoromethyl-phenyl)-urea

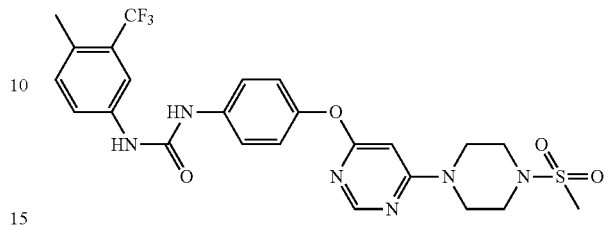

Synthesis of the compound of Example 150 was accomplished by using procedures similar to that described in Example 57. MS(ESI) m/z (M+1)+: 551.17.

Example 151: [1-(6-{4-[3-(4-methyl-3-trifluoromethyl-phenyl)-ureido]-phenoxy}-pyrimidin-4-yl)-piperidin-4-yl]-aminotert-butyl formate

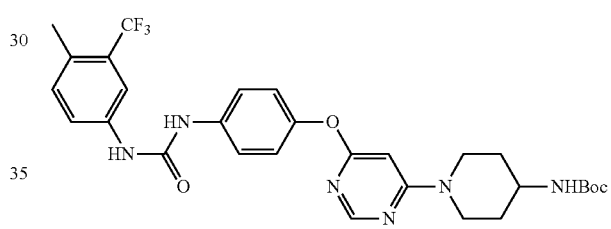

Synthesis of the compound of Example 151 was accomplished by using procedures similar to that described in Example 57. MS(ESI) m/z (M+1)+: 587.26.

Example 152: 1-[4-(6-cyclohexylamino-pyrimidin-4-yloxy)-phenyl]-3-(4-methyl-3-trifluoromethyl-phenyl)-urea

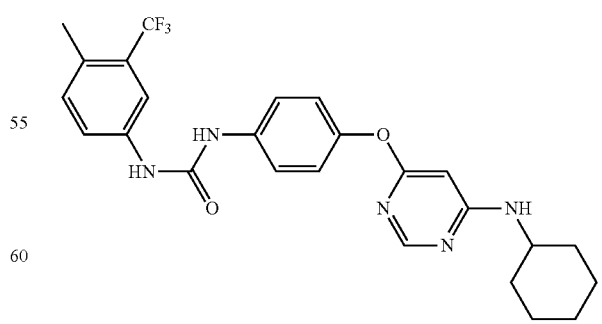

Synthesis of the compound of Example 152 was accomplished by using procedures similar to that described in Example 57. MS(ESI) m/z (M+1)+: 486.21.

Example 153: 1-[4-(6-cyclopentylamino-pyrimidin-4-yloxy)-phenyl]-3-(4-methyl-3-trifluoromethyl-phenyl)-urea

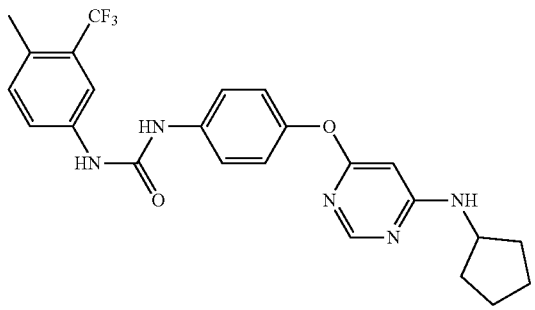 [SMILES: Cc1ccc(NC(=O)Nc2ccc(Oc3cc(NC4CCCC4)ncn3)cc2)cc1C(F)(F)F]

Synthesis of the compound of Example 153 was accomplished by using procedures similar to that described in Example 57. MS(ESI) m/z (M+1)+: 472.20.

Example 154: 1-(4-methyl-3-trifluoromethyl-phenyl)-3-{4-[6-(4-morpholin-4-yl-piperidin-1-yl)-pyrimidin-4-yloxy]-phenyl}-urea

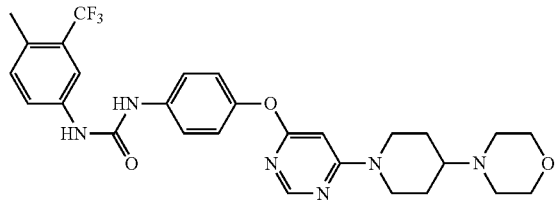 [SMILES: Cc1ccc(NC(=O)Nc2ccc(Oc3cc(N4CCC(N5CCOCC5)CC4)ncn3)cc2)cc1C(F)(F)F]

Synthesis of the compound of Example 154 was accomplished by using procedures similar to that described in Example 57. MS(ESI) m/z (M+1)+: 557.25.

Example 155: 1-(4-methyl-3-trifluoromethyl-phenyl)-3-{4-[6-(3-morpholin-4-yl-propylamino)-pyrimidin-4-yloxy]-phenyl}-urea

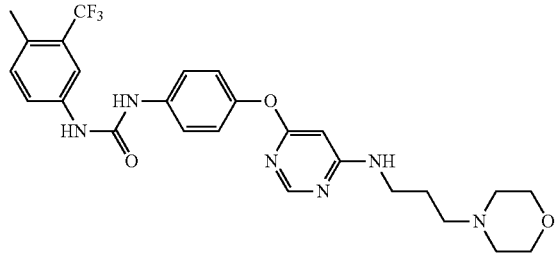 [SMILES: Cc1ccc(NC(=O)Nc2ccc(Oc3cc(NCCCN4CCOCC4)ncn3)cc2)cc1C(F)(F)F]

Synthesis of the compound of Example 155 was accomplished by using procedures similar to that described in Example 57. MS(ESI) m/z (M+1)+: 531.24.

Example 156: 1-(4-{6-[4-(4-methyl-piperazin-1-yl)-piperidin-1-yl]-pyrimidin-4-yloxy}-phenyl)-3-(4-methyl-3-trifluoromethyl-phenyl)-urea

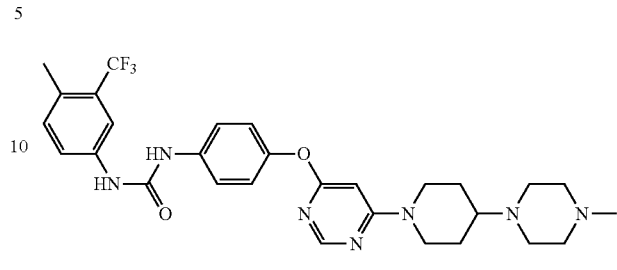

Synthesis of the compound of Example 156 was accomplished by using procedures similar to that described in Example 57. MS(ESI) m/z (M+1)+: 570.28.

Example 157: 1-{4-[6-(4-isopropyl-piperazin-1-yl)-pyrimidin-4-yloxy]-phenyl}-3-(4-methyl-3-trifluoromethyl-phenyl)-urea

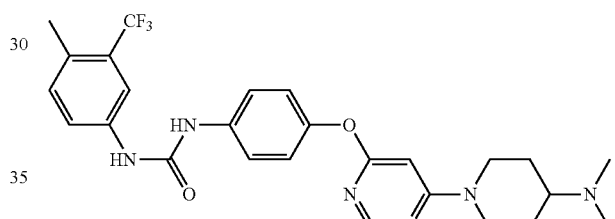

Synthesis of the compound of Example 157 was accomplished by using procedures similar to that described in Example 57. MS(ESI) m/z (M+1)+: 515.24.

Example 158: 1-(4-{6-[4-(4-mesyl-piperazin-1-yl)-piperidin-1-yl]-pyrimidin-4-yloxy}-phenyl)-3-(4-methyl-3-trifluoromethyl-phenyl)-urea

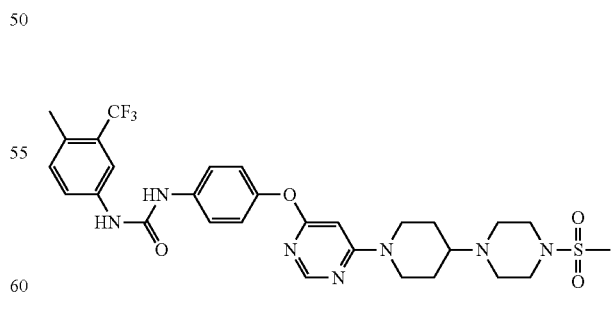

Synthesis of the compound of Example 158 was accomplished by using procedures similar to that described in Example 57. MS(ESI) m/z (M+1)+: 633.24.

Example 159: (S)-2-((6-(4-(3-(4-methyl-3-(trifluoromethyl)phenyl)ureido)phenoxy)pyrimidin-4-yl)amino)methyl propionate

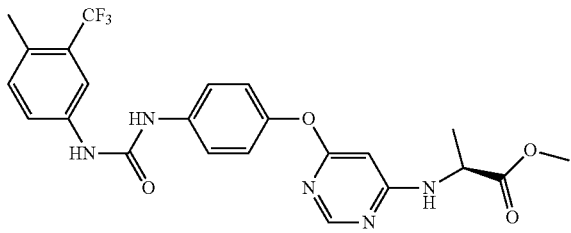 [SMILES: COC(=O)[C@H](C)Nc1cc(Oc2ccc(NC(=O)Nc3ccc(C)c(C(F)(F)F)c3)cc2)ncn1]

Synthesis of the compound of Example 159 was accomplished by using procedures similar to that described in Example 57. MS(ESI) m/z (M+1)+: 490.17.

Example 160: 4-(6-acetylamino-pyrimidin-4-yloxy)-N-benzylbenzamide

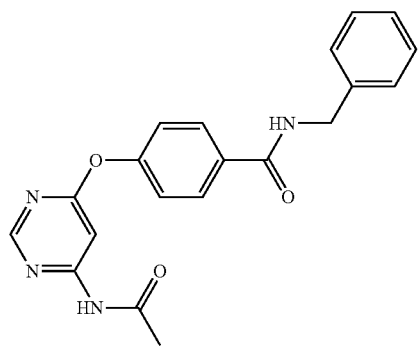 [SMILES: CC(=O)Nc1cc(Oc2ccc(C(=O)NCc3ccccc3)cc2)ncn1]

Synthesis of the compound of Example 160 was accomplished by using procedures similar to that described in Example 1. MS(ESI) m/z (M+1)+: 363.14.

Example 161: N-[4-(6-acetylamino-pyrimidin-4-yloxy)-phenyl]-2-(2-methyl-phenyl)-acetamide

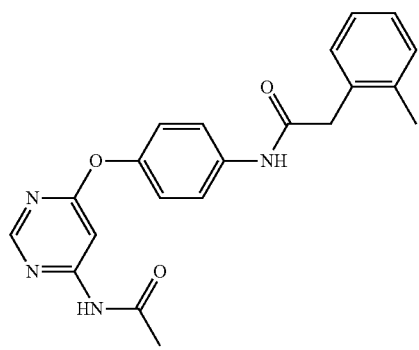 [SMILES: CC(=O)Nc1cc(Oc2ccc(NC(=O)Cc3ccccc3C)cc2)ncn1]

Synthesis of the compound of Example 161 was accomplished by using procedures similar to that described in Example 1. MS(ESI) m/z (M+1)+: 377.16.

Example 162: N-[4-(6-acetylamino-pyrimidin-4-yloxy)-phenyl]-2-naphth-2-yl-acetamide

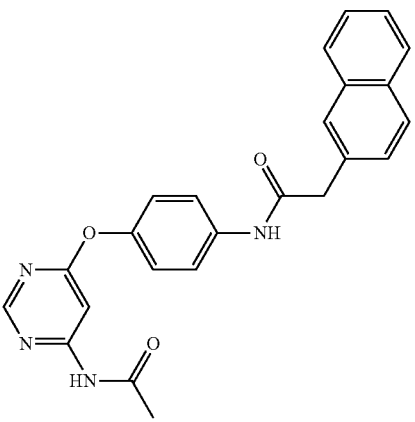 [SMILES: CC(=O)Nc1cc(Oc2ccc(NC(=O)Cc3ccc4ccccc4c3)cc2)ncn1]

Synthesis of the compound of Example 162 was accomplished by using procedures similar to that described in Example 1. MS(ESI) m/z (M+1)+: 413.16.

Example 163: N-[4-(6-acetylamino-pyrimidin-4-yloxy)-phenyl]-2-naphth-1-yl-acetamide

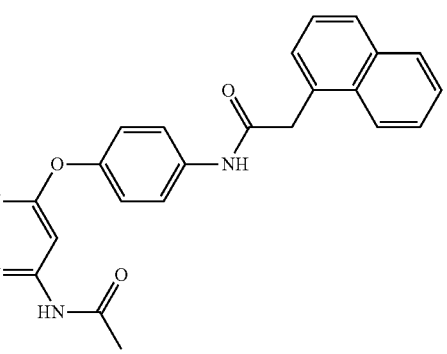

Synthesis of the compound of Example 163 was accomplished by using procedures similar to that described in Example 1. MS(ESI) m/z (M+1)+: 413.16.

Example 164: N-[4-(6-acetylamino-pyrimidin-4-ylamino)-phenyl]-2-(2-trifluoromethyl-phenyl)-acetamide

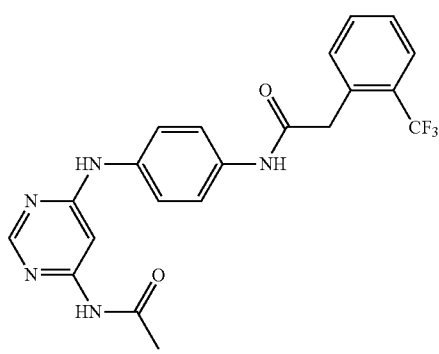 [SMILES: CC(=O)Nc1cc(Nc2ccc(NC(=O)Cc3ccccc3C(F)(F)F)cc2)ncn1]

Synthesis of the compound of Example 164 was accomplished by using procedures similar to that described in Example 1. MS(ESI) m/z (M+1)+: 430.15.

Example 165: N-[4-(6-acetylamino-pyrimidin-4-ylamino)-phenyl]-2-(3-trifluoromethyl-phenyl)-acetamide

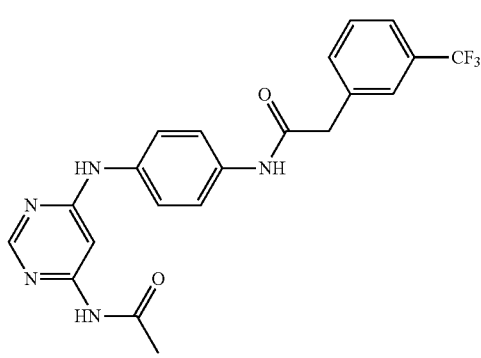 [SMILES: CC(=O)Nc1cc(Nc2ccc(NC(=O)Cc3cccc(C(F)(F)F)c3)cc2)ncn1]

Synthesis of the compound of Example 165 was accomplished by using procedures similar to that described in Example 1. MS(ESI) m/z (M+1)+: 430.15.

Example 166: N-[4-(6-acetylamino-pyrimidin-4-ylamino)-phenyl]-2-(4-trifluoromethyl-phenyl)-acetamide

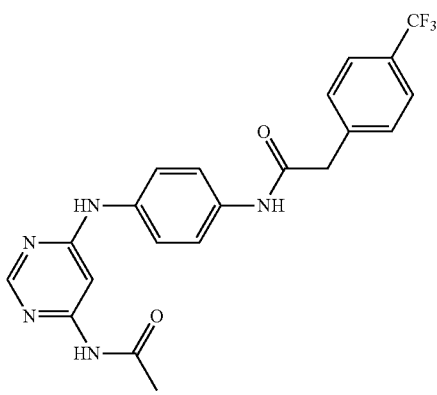 [SMILES: CC(=O)Nc1cc(Nc2ccc(NC(=O)Cc3ccc(C(F)(F)F)cc3)cc2)ncn1]

Synthesis of the compound of Example 166 was accomplished by using procedures similar to that described in Example 1. MS(ESI) m/z (M+1)+: 430.15.

Example 167: N-(6-{4-[2-(2-trifluoromethyl-phenyl)-acetylamino]-phenoxy}-pyrimidin-4-yl)-butyramide

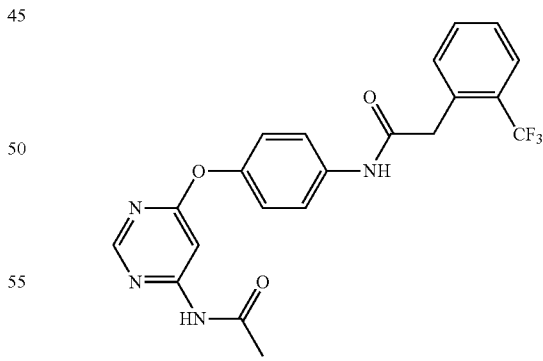

Synthesis of the compound of Example 167 was accomplished by using procedures similar to that described in Example 1. MS(ESI) m/z (M+1)+: 459.17.

Example 168: N-[4-(6-acetylamino-pyrimidin-4-yloxy)-phenyl]-2-(3,4-difluoro-phenyl)-acetamide

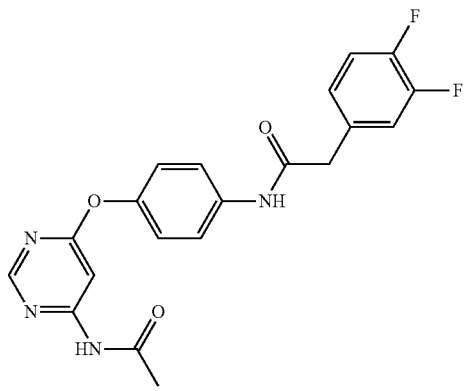 [SMILES: CC(=O)Nc1cc(Oc2ccc(NC(=O)Cc3ccc(F)c(F)c3)cc2)ncn1]

Synthesis of the compound of Example 168 was accomplished by using procedures similar to that described in Example 1. MS(ESI) m/z (M+1)+: 399.13.

Example 169: N-[4-(6-acetylamino-pyrimidin-4-yloxy)-phenyl]-2-(3-chloro-phenyl)-acetamide

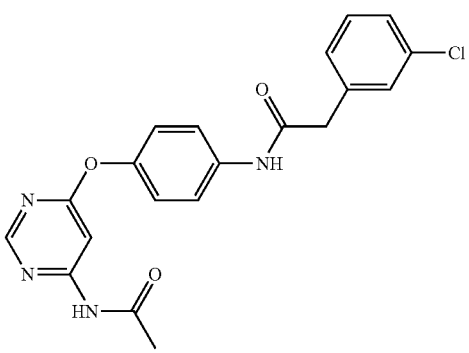 [SMILES: CC(=O)Nc1cc(Oc2ccc(NC(=O)Cc3cccc(Cl)c3)cc2)ncn1]

Synthesis of the compound of Example 169 was accomplished by using procedures similar to that described in Example 1. MS(ESI) m/z (M+1)+: 397.11.

Example 170: N-[4-(6-acetylamino-pyrimidin-4-yloxy)-phenyl]-2-(4-methyl-phenyl)-propanamide

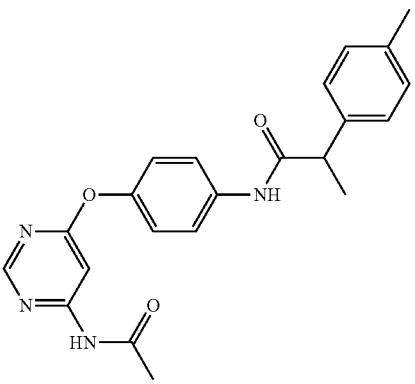 [SMILES: CC(=O)Nc1cc(Oc2ccc(NC(=O)C(C)c3ccc(C)cc3)cc2)ncn1]

Synthesis of the compound of Example 170 was accomplished by using procedures similar to that described in Example 1. MS(ESI) m/z (M+1)+: 391.18.

Example 171: 1-{4-[6-(2-methoxy-ethylamino)-pyrimidin-4-yloxy]-phenyl}-3-[4-(4-methyl-piperazin-1-ylmethyl)-3-trifluoromethyl-phenyl]-urea

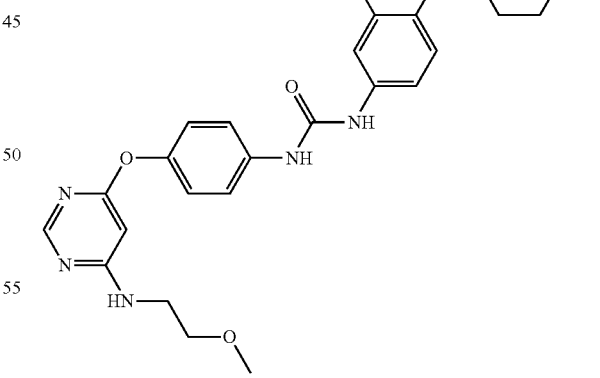

Synthesis of the compound of Example 171 was accomplished by using procedures similar to that described in Example 57. MS(ESI) m/z (M+1)+: 560.26.

Example 172: 1-{4-[6-(2-methoxy-ethylamino)-pyrimidin-4-yloxy]-phenyl}-3-[4-(4-methyl-piperazin-1-ylmethyl)-phenyl]-urea

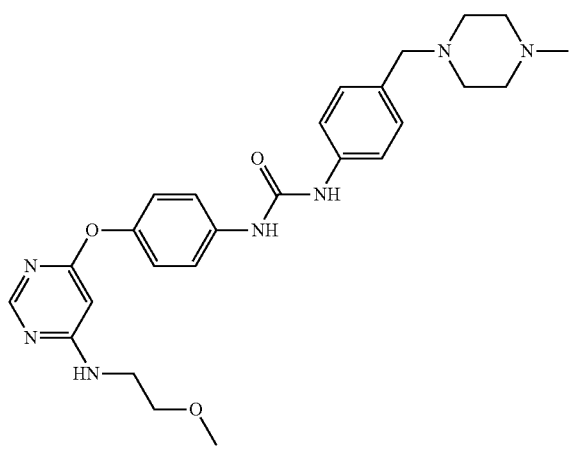 [SMILES: COCCNc1cc(Oc2ccc(NC(=O)Nc3ccc(CN4CCN(C)CC4)cc3)cc2)ncn1]

Synthesis of the compound of Example 172 was accomplished by using procedures similar to that described in Example 57. MS(ESI) m/z (M+1)+: 492.27.

Example 173: N-[4-(6-acetylamino-pyrimidin-4-yloxy)-phenyl]-2-(3,5-difluoro-phenyl)-acetamide

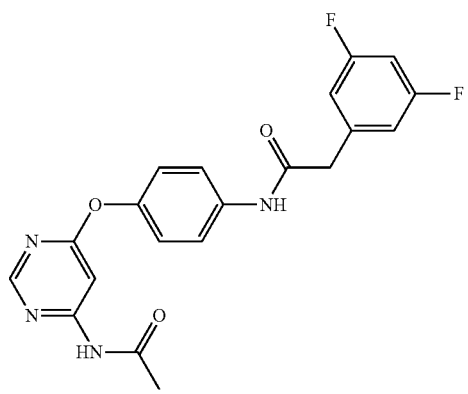 [SMILES: CC(=O)Nc1cc(Oc2ccc(NC(=O)Cc3cc(F)cc(F)c3)cc2)ncn1]

Synthesis of the compound of Example 173 was accomplished by using procedures similar to that described in Example 1. MS(ESI) m/z (M+1)+: 399.13.

Example 174: (S)—N-(4-((6-acetamidopyrimidin-4-yl)oxy)phenyl)-2-methoxy-2-phenylacetamide

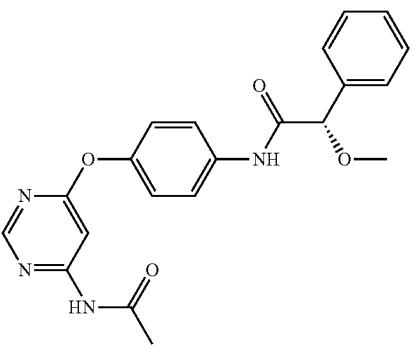 [SMILES: CO[C@H](C(=O)Nc1ccc(Oc2cc(NC(C)=O)ncn2)cc1)c1ccccc1]

Synthesis of the compound of Example 174 was accomplished by using procedures similar to that described in Example 1. MS(ESI) m/z (M+1)+: 393.16.

Example 175: N-[4-(6-acetylamino-pyrimidin-4-yloxy)-phenyl]-2-(5-chloro-2-trifluoromethyl-phenyl)-acetamide

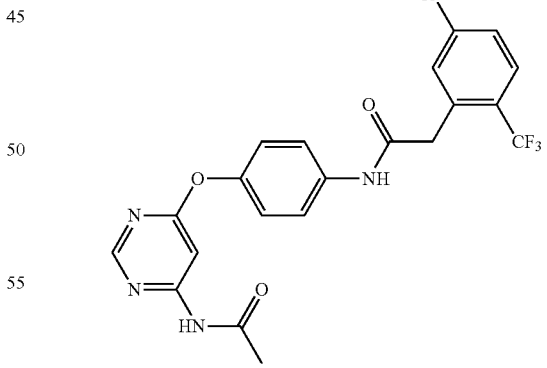

Synthesis of the compound of Example 175 was accomplished by using procedures similar to that described in Example 1. MS(ESI) m/z (M+1)+: 465.10.

Example 176: N-[4-(6-acetylamino-pyrimidin-4-yloxy)-phenyl]-2-(3-chloro-4-hydroxy-phenyl)-acetamide

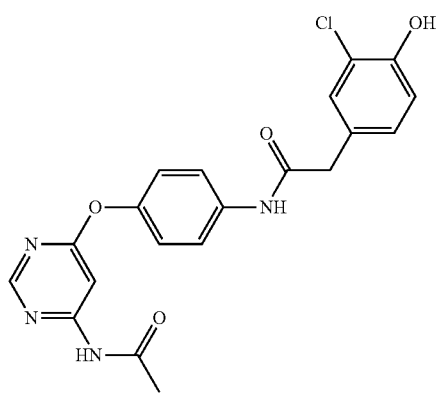 [SMILES: CC(=O)Nc1cc(Oc2ccc(NC(=O)Cc3ccc(O)c(Cl)c3)cc2)ncn1]

Synthesis of the compound of Example 176 was accomplished by using procedures similar to that described in Example 1. MS(ESI) m/z (M+1)+: 413.10.

Example 177: N-{4-[6-(3-nitro-phenylamino)-pyrimidin-4-yloxy]-phenyl}-2-(2-trifluoromethyl-phenyl)-acetamide

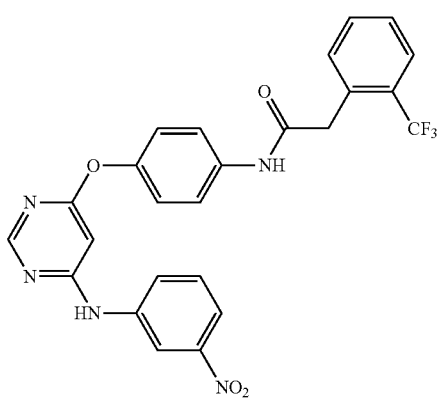 [SMILES: O=C(Cc1ccccc1C(F)(F)F)Nc1ccc(Oc2cc(Nc3cccc([N+](=O)[O-])c3)ncn2)cc1]

Synthesis of the compound of Example 177 was accomplished by using procedures similar to that described in Example 1. MS(ESI) m/z (M+1)+: 510.14.

Example 178: 1-{4-[6-(2-methoxy-ethylamino)-pyrimidin-4-yloxy]-phenyl}-3-[4-(4-methyl-piperazin-1-ylmethyl)-3-trifluoromethyl-phenyl]-urea

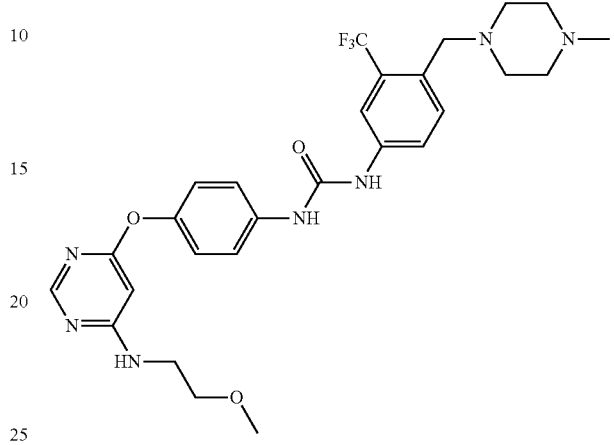

Synthesis of the compound of Example 178 was accomplished by using procedures similar to that described in Example 57. MS(ESI) m/z (M+1)+: 560.26.

Example 179: (S)-4-(6-(4-(2-(2,4-difluorophenyl)acetamido)phenoxy)pyrimidin-4-yl)-3-ethylpiperazin-1-tert-butyl Formate

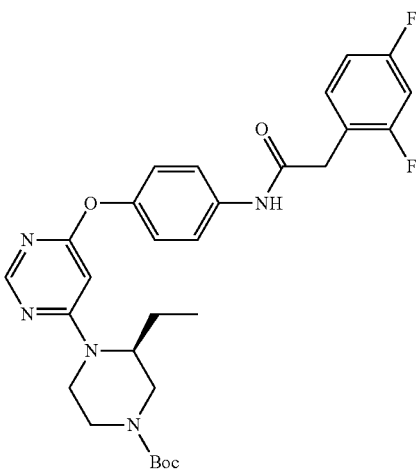 [SMILES: CC[C@H]1CN(C(=O)OC(C)(C)C)CCN1c1cc(Oc2ccc(NC(=O)Cc3ccc(F)cc3F)cc2)ncn1]

Synthesis of the compound of Example 179 was accomplished by using procedures similar to that described in Example 1. MS(ESI) m/z (M+1)+: 554.26.

Example 180: 1-{4-[6-(4-methoxy-benzylamino)-pyrimidin-4-yloxy]-phenyl}-3-(4-piperazin-1-ylmethyl-3-trifluoromethyl-phenyl)-urea

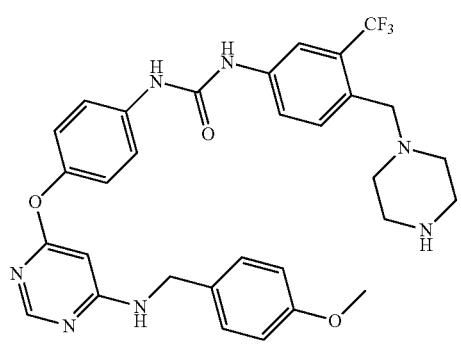 [SMILES: COc1ccc(CNc2cc(Oc3ccc(NC(=O)Nc4ccc(CN5CCNCC5)c(C(F)(F)F)c4)cc3)ncn2)cc1]

Synthesis of the compound of Example 180 was accomplished by using procedures similar to that described in Example 57. MS(ESI) m/z (M+1)+: 608.26.

Example 181: N-[4-(6-acetylamino-pyrimidin-4-yloxy)-2-methyl-phenyl]-2-(2-trifluoromethyl-phenyl)-acetamide

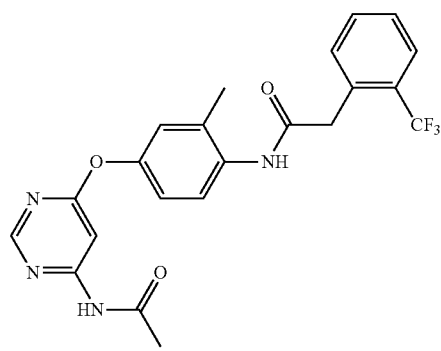 [SMILES: CC(=O)Nc1cc(Oc2ccc(NC(=O)Cc3ccccc3C(F)(F)F)c(C)c2)ncn1]

Synthesis of the compound of Example 181 was accomplished by using procedures similar to that described in Example 1. MS(ESI) m/z (M+1)+: 445.15.

Example 182: N-[4-(6-acetylamino-pyrimidin-4-yloxy)-2-methyl-phenyl]-2-(4-trifluoromethyl-phenyl)-acetamide

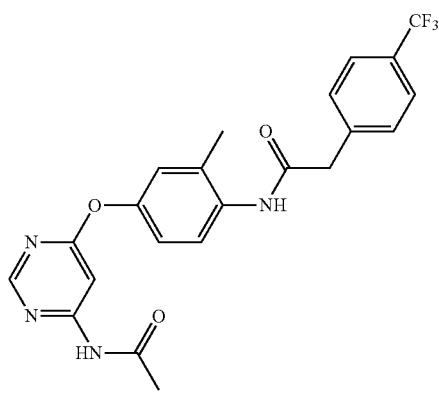 [SMILES: CC(=O)Nc1cc(Oc2ccc(NC(=O)Cc3ccc(C(F)(F)F)cc3)c(C)c2)ncn1]

Synthesis of the compound of Example 182 was accomplished by using procedures similar to that described in Example 1. MS(ESI) m/z (M+1)+: 445.15.

Example 183: N-[4-(6-acetylamino-pyrimidin-4-yloxy)-2-methyl-phenyl]-2-(2,4-difluoro-phenyl)-acetamide

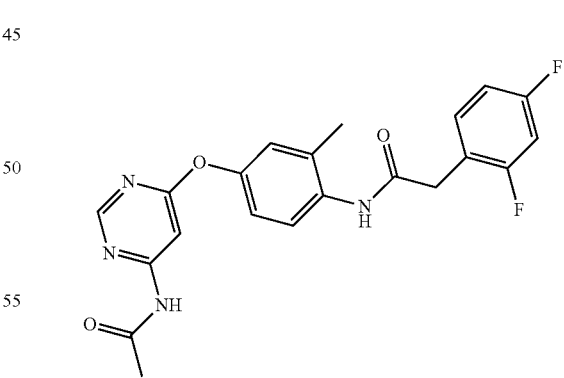

Synthesis of the compound of Example 183 was accomplished by using procedures similar to that described in Example 1. MS(ESI) m/z (M+1)+: 413.14.

Example 184: N-[4-(6-acetylamino-pyrimidin-4-yloxy)-2-methyl-phenyl]-2-(4-methyl-3-trifluoromethyl-phenyl)-acetamide

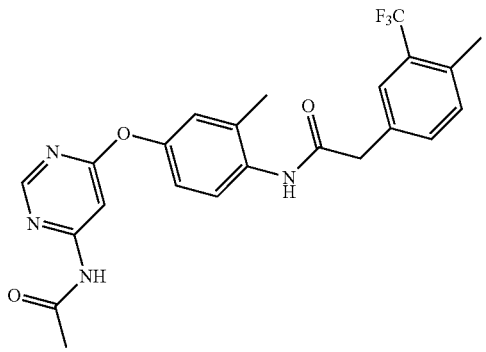 [SMILES: CC(=O)Nc1cc(Oc2ccc(NC(=O)Cc3ccc(C)c(C(F)(F)F)c3)c(C)c2)ncn1]

Synthesis of the compound of Example 184 was accomplished by using procedures similar to that described in Example 1. MS(ESI) m/z (M+1)+: 459.17.

Example 185: N-[4-(6-acetylamino-pyrimidin-4-yloxy)-2-methyl-phenyl]-2-(3-trifluoromethyl-phenyl)-acetamide

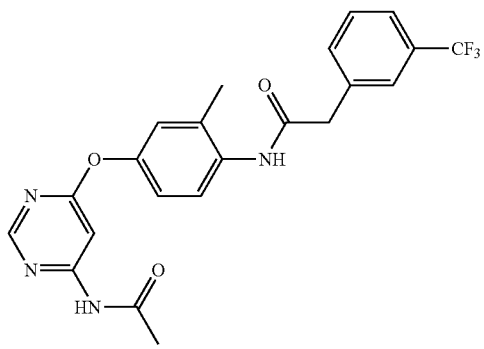 [SMILES: CC(=O)Nc1cc(Oc2ccc(NC(=O)Cc3cccc(C(F)(F)F)c3)c(C)c2)ncn1]

Synthesis of the compound of Example 185 was accomplished by using procedures similar to that described in Example 1. MS(ESI) m/z (M+1)+: 445.15.

Example 186: Effects on Proliferation of Cancer Cells

Compounds of the invention were evaluated for their inhibitory effects on proliferation of cancer cells as well as the selectivity thereof by testing their effects on growth of cancer cells (Table 2).

In this example the following cells were used: primary mouse B cells (purchased from ATCC), mouse P210-BaF3 (stably expressing BCR-ABL mutant activated kinase), mouse P210/T315I-BaF3 (stably expressing BCR-ABL/T315I mutant activated kinase), mouse FLT3-ITD-BaF3 (stably expressing FLT3/ITD mutant activated kinase), mouse TEL-FLT3-BaF3 (stably expressing FLT3 kinase), mouse TEL-cKIT-BaF3 (stably expressing cKIT kinase), mouse BaF3-tel/T670I-cKit (stably expressing cKIT/T670I mutant activated kinase), mouse Tel-VEGFR2-BaF3 (stably expressing VEGFR2 kinase), mouse Tel-PDGFRα-BaF3 (stably expressing PDGFRα kinase), mouse Tel-PDGFRβ-BaF3 (stably expressing PDGFRβ kinase), mouse Tel-RET-BaF3 (stably expressing RET kinase). The above cell lines were all constructed by our laboratory according to the following method: the kinase region sequences of human P210, P210/T315I, FLT3/ITD, FLT3, cKIT, cKIT/T670I, VEGFR2, PDGFRα, PDGFRβ, RET were respectively amplified by PCR, and inserted into MSCV-Puro vectors having N-terminal TEL or TPR fragments (Clontech). The vectors were stably transfected into mouse BaF3 cells by means of retrovirus, and the growth factor IL-3 were removed, eventually obtaining cell lines that depend on transferred protein P210, P210/T315I, FLT3/ITD, FLT3, cKIT, cKIT/T670I, VEGFR2, PDGFRα, PDGFRβ, or RET.

In the example the above cells were added with test compounds at different concentrations (0.000508 μM, 0.00152 μM, 0.00457 μM, 0.0137 μM, 0.0411 μM, 0.123 μM, 0.370 μM, 1.11 μM, 3.33 μM, 10 μM in DMSO) or with the control compound, Sorafenib (MedChem Express, China), and incubated for 72 hours. $GI_{50}$ (unit: μM) was calculated by quantifying the number of living cells based on quantitative measurement of reductive dehydrogenase in living cells with CCK8 cell viability assay kit (Bestbio, China). Experimental results were shown in Table 2.

TABLE 2

| Compound No. | BaF3 | P210-BaF3 | P210/T315I-BaF3 | Tel-cKit-BaF3 | Tel-cKit/T670I-BaF3 | Tel-FLT3-BaF3 | FLT3-ITD-BaF3 | Tel-RET-BaF3 | TEL-PDGFRα-BaF3 | TEL-PDGFRβ-BaF3 | TEL-VEGFR2-BaF3 |
|---|---|---|---|---|---|---|---|---|---|---|---|
| 2 | >10 | | | 6.93 | >10 | 0.744 | 0.158 | | 0.102 | 0.156 | 2.83 |
| 3 | >10 | | | 1.42 | 8.9 | 0.325 | 0.109 | | 0.007 | 0.022 | 1.09 |
| 4 | >10 | >10 | | >10 | >10 | 0.667 | 0.061 | >10 | 0.013 | 0.048 | 0.734 |
| 5 | >10 | >10 | | 5.6 | >10 | 0.746 | 0.03 | >10 | 0.014 | 0.058 | 0.357 |
| 6 | >10 | >10 | | >10 | >10 | 0.663 | 0.063 | >10 | 0.059 | 0.346 | 1.93 |
| 7 | >10 | >10 | | 3.21 | >10 | 0.236 | 0.067 | >10 | 0.035 | 0.07 | 0.518 |
| 8 | >10 | 6.74 | >10 | 0.524 | >10 | 0.017 | 0.004 | >10 | 0.001 | 0.003 | 0.139 |
| 9 | >10 | >10 | >10 | 0.584 | 5.63 | 0.012 | 0.002 | >10 | 0.004 | 0.01 | 0.304 |
| 11 | >10 | >10 | >10 | >10 | >10 | 1.1 | 0.346 | >10 | 0.227 | 0.271 | 1.52 |
| 12 | >10 | >10 | >10 | 2.13 | 8.64 | 0.649 | 0.204 | 0.672 | 0.02 | 0.029 | 0.229 |
| 13 | >10 | >10 | >10 | 6.89 | >10 | 0.616 | 0.099 | >10 | 0.004 | 0.033 | 0.566 |
| 14 | >10 | >10 | >10 | >10 | >10 | 0.713 | 0.284 | >10 | 0.089 | 0.341 | 1.24 |
| 16 | >10 | >10 | >10 | >10 | >10 | 0.818 | 0.247 | 0.247 | 0.012 | 0.109 | 0.853 |
| 17 | >10 | >10 | >10 | >10 | >10 | 0.744 | 0.129 | 0.229 | 0.013 | 0.105 | 0.553 |
| 24 | >10 | >10 | >10 | >10 | >10 | 1.76 | 0.331 | >10 | 0.077 | 0.356 | 3.1 |
| 25 | >10 | >10 | 1.04 | >10 | >10 | 1.15 | 0.263 | >10 | 0.033 | 0.073 | 2.11 |
| 26 | >10 | >10 | >10 | 8.68 | >10 | 0.436 | 0.077 | >10 | 0.074 | 0.18 | 1.24 |
| 33 | >10 | | | 0.301 | 0.081 | 0.004 | 0.01 | | 0.001 | 0.004 | 0.013 |
| 35 | >10 | >10 | | >10 | 6.6 | 0.925 | 0.067 | | 0.203 | 0.406 | |

TABLE 2-continued

| Compound No. | BaF3 | P210-BaF3 | P210/T315I-BaF3 | Tel-cKit-BaF3 | Tel-cKit/T670I-BaF3 | Tel-FLT3-BaF3 | FLT3-ITD-BaF3 | Tel-RET-BaF3 | TEL-PDGFRα-BaF3 | TEL-PDGFRβ-BaF3 | TEL-VEGFR2-BaF3 |
|---|---|---|---|---|---|---|---|---|---|---|---|
| 36 | >10 | | | 0.589 | 0.036 | 0.017 | 0.004 | | <0.001 | 0.002 | |
| 37 | >10 | >10 | | >10 | 4.03 | 2.27 | 0.162 | | 0.005 | 0.004 | |
| 38 | >10 | >10 | | >10 | 8.31 | 0.632 | 0.213 | | 0.035 | 0.466 | 2.85 |
| 39 | >10 | >10 | | 7.88 | >10 | 0.347 | 0.18 | | 0.057 | 0.134 | 4.26 |
| 40 | 5.06 | 5.36 | 3.93 | 5.19 | 2.4 | 0.58 | 0.168 | 4.18 | 0.021 | 0.33 | 5.09 |
| 41 | 7.8 | 4.43 | 4.69 | 5.12 | 0.707 | 0.263 | 0.109 | 3.18 | 0.059 | 0.233 | 2.9 |
| 42 | 5.5 | 5.38 | 4.11 | 5.18 | 3.91 | 0.198 | 0.274 | 3.59 | 0.094 | 0.096 | 3.77 |
| 43 | >10 | 6.96 | 5.21 | 5.3 | 1.12 | 0.305 | 0.199 | 3.4 | 0.023 | 0.252 | 2.6 |
| 46 | 7.88 | >10 | 9.17 | 5.1 | 0.765 | 0.228 | 0.087 | 4.03 | 0.024 | 0.248 | 3.03 |
| 47 | >10 | >10 | >10 | 8.35 | >10 | 0.546 | 0.142 | >10 | 0.028 | 0.089 | 3.17 |
| 49 | >10 | >10 | >10 | >10 | >10 | 2.58 | 1.97 | >10 | 0.059 | 0.145 | 6.11 |
| 50 | >10 | >10 | >10 | 0.855 | 9.22 | 0.814 | 0.206 | >10 | 0.005 | 0.007 | 2.58 |
| 52 | >10 | >10 | >10 | 2.26 | 5.68 | 3 | 0.374 | | 0.033 | 0.092 | 3.42 |
| 55 | >10 | >10 | >10 | 4.6 | 6.3 | 0.65 | 0.14 | 7.9 | 0.038 | 0.061 | 3.9 |
| 60 | >10 | >10 | >10 | 0.917 | 1.88 | 0.195 | 0.014 | | 0.011 | 0.026 | 0.433 |
| 61 | 5.71 | 5.61 | 9.77 | 4.89 | >10 | 1.39 | 0.063 | | 0.074 | 0.233 | 1.78 |
| 62 | >10 | >10 | >10 | 0.81 | 6.58 | 0.39 | 0.05 | | 0.045 | 0.231 | 1.18 |
| 63 | >10 | >10 | >10 | >10 | >10 | 4.68 | 0.325 | | 0.476 | 5.75 | 3.43 |
| 65 | >10 | >10 | >10 | 0.376 | 1.07 | 0.612 | 0.024 | | 0.012 | 0.084 | 0.277 |
| 67 | >10 | 8.08 | 9.79 | 6.17 | >10 | 1.47 | 0.291 | | 0.014 | 0.312 | 7.82 |
| 73 | >10 | >10 | >10 | 5.68 | >10 | 1.57 | 0.17 | >10 | 0.165 | 0.154 | |
| 87 | 7.21 | | 8.49 | 0.354 | 8.85 | 0.169 | 0.058 | | 0.026 | 0.115 | 0.398 |
| 99 | >10 | | | 0.34 | 0.99 | 0.066 | 0.017 | 4.6 | 0.014 | 0.277 | 0.202 |
| 100 | 9.01 | | | 1.52 | 8.08 | 0.6 | 0.03 | 5.82 | 0.063 | 0.342 | 1.66 |
| 103 | >10 | | | 3.22 | 9.53 | 0.48 | 0.19 | >10 | 0.07 | 0.355 | 2.89 |
| 104 | 8.48 | | | 1.8 | 5.13 | 0.67 | 0.29 | 3.62 | 0.014 | 0.173 | 2.89 |
| 105 | 9.67 | | | 0.99 | 2.16 | 0.2 | 0.086 | 2.75 | 0.014 | 0.195 | 0.323 |
| 106 | 8.92 | | | 1.73 | 0.99 | 0.46 | 0.3 | | 0.021 | 0.136 | 0.35 |
| 107 | 8.12 | | | 2.85 | 0.94 | 0.34 | 0.15 | 1.98 | 0.034 | 0.117 | 0.508 |
| 108 | >10 | | | 0.97 | 7.82 | 0.011 | 0.009 | 3.88 | 0.016 | 0.324 | 0.098 |
| 109 | 3.54 | | | 0.999 | 3.36 | 0.011 | 0.007 | 0.46 | 0.013 | 0.392 | 0.145 |
| 110 | >10 | | | 2.25 | 5.29 | 4.86 | 0.182 | 6.21 | 0.06 | 0.27 | 4.62 |
| 111 | >10 | | | 6.05 | 8.6 | 6.16 | 0.141 | >10 | 0.19 | 0.69 | 1.74 |
| 112 | 4.12 | | | 1.07 | 0.886 | 0.599 | 0.058 | 3.82 | 0.023 | 0.051 | 0.39 |
| 113 | >10 | | | 3.22 | 8.54 | 0.638 | 0.259 | >10 | 0.086 | 0.17 | 1.26 |
| 114 | 6.05 | | | 0.287 | 1.01 | 1.09 | 0.037 | 3.83 | 0.005 | 0.03 | 1.33 |
| 115 | 9.87 | | | 2.12 | 4.25 | 2.19 | 0.413 | 3.97 | 0.052 | 0.19 | 2.28 |
| 122 | 3.37 | 3.92 | 3.92 | 0.391 | 0.394 | 0.206 | 0.036 | 4.3 | 0.008 | 0.017 | 0.17 |
| 124 | 1.17 | 2.8 | 1.54 | 2.56 | 2.27 | 0.694 | 0.149 | 1.92 | 0.15 | 0.18 | 0.89 |
| 126 | >10 | >10 | >10 | 1.66 | 4.68 | 0.797 | 0.153 | 6.38 | 0.14 | 0.49 | 0.41 |
| 128 | >10 | >10 | 8.73 | 8.47 | 0.641 | 0.15 | 0.087 | 3.87 | 0.11 | 0.15 | 1.19 |
| 135 | >10 | >10 | >10 | >10 | >10 | 0.249 | 0.032 | >10 | 0.007 | 0.04 | 1.44 |
| 137 | >10 | >10 | | 9.93 | 0.465 | 0.323 | 0.04 | 0.012 | 0.011 | 0.034 | 0.149 |
| 138 | >10 | >10 | >10 | 2.6 | 0.377 | 0.034 | 0.014 | | 0.017 | 0.079 | 0.711 |
| 139 | >10 | >10 | 9.8 | >10 | 9.98 | 1 | 0.432 | | 0.319 | 0.034 | 8.91 |
| 140 | >10 | >10 | 9.61 | >10 | >10 | 1.11 | 0.377 | | 0.131 | 0.17 | 9.67 |
| 142 | >10 | >10 | >10 | 0.736 | 1.84 | 0.162 | 0.054 | | 0.007 | 0.008 | 9.67 |
| 161 | >10 | >10 | >10 | 7.01 | >10 | 0.228 | 0.074 | | 0.024 | 0.116 | |
| 162 | >10 | >10 | >10 | 0.313 | 0.915 | 0.113 | 0.019 | | 0.004 | 0.006 | |
| 163 | >10 | >10 | 9.07 | 0.924 | 3.27 | 0.025 | 0.011 | | 0.005 | 0.014 | |
| 164 | >10 | >10 | >10 | >10 | >10 | 1.41 | 0.444 | | 0.084 | 0.938 | |
| 165 | >10 | >10 | >10 | 0.462 | 4.61 | 0.052 | 0.021 | | 0.001 | 0.012 | |
| 167 | >10 | >10 | >10 | 9.84 | 7.94 | 0.513 | 0.126 | | 0.041 | 0.112 | |
| 168 | >10 | >10 | >10 | 2.69 | 4.23 | 0.099 | 0.042 | | 0.006 | 0.033 | |
| 169 | >10 | >10 | >10 | 1.7 | >10 | 0.105 | 0.024 | | 0.005 | 0.035 | |
| 170 | >10 | >10 | >10 | >10 | >10 | 3.16 | 1.22 | | 0.137 | 0.925 | |
| 172 | >10 | >10 | >10 | >10 | >10 | 1.1 | 0.34 | >10 | 0.11 | 0.75 | 8.3 |
| 173 | >10 | >10 | >10 | 3.6 | >10 | 0.51 | 0.092 | >10 | 0.014 | 0.039 | 1.4 |
| 180 | 9.01 | | 1.72 | 0.33 | 2.85 | 0.022 | 0.003 | 0.331 | 0.112 | 0.315 | 0.039 |
| Sorafenib | 6.99 | 3.83 | 7.79 | 0.058 | 0.112 | 0.0009 | 0.0003 | 0.365 | 0.0006 | 0.035 | 0.033 |

It can be seen from Table 2 that the compounds of the present invention exhibited strong inhibition against FLT3-ITD-BaF3, TEL-PDGFRα-BaF3 and TEL-PDGFRβ-BaF3, demonstrating that these compounds mainly targeted FLT3, FLT3-ITD, PDGFRα, and/or PDGFRβ. If a drug that targets FLT3 and FLT3-ITD also has activity against c-Kit, it may incur myelosuppression in clinic. Therefore, it would be safer to select a drug that selectively target FLT3-ITD for treating acute myeloid leukemia. As to sorafenib which is multitarget compound, it not only acts on FLT3 and FLT3-ITD, but also strongly inhibits cKIT. In contrast, the compounds of the present invention mainly focus on FLT3, FLT3-ITD, PDGFRα, and/or PDGFRβ.

In addition, in this example the inhibitory activity of preferred compounds (Compound 5 and Compound 135) was tested against the following cell strains: human acute myeloid leukemia cell strain MV4-11 (expressing FLT3/ITD mutant gene), human acute myeloid leukemia cell strain MOLM-13 (expressing FLT3/ITD mutant gene and wild-type FLT3 gene), human acute myeloid leukemia cell strain MOLM-14 (expressing FLT3/ITD mutant gene and wild-type FLT3 gene), human acute myeloid leukemia cell strain OCI-AML-3 (expressing FLT3 A680V mutant gene), human chronic lymphatic leukemia cell strain MEC-1, Chinese hamster lung (CHL) cells, Chinese hamster ovary (CHO) cells, wherein all the cells were purchased from ATCC. In the example the compounds of the present invention were added respectively into the above cells at different concentrations (0.000508 μM, 0.00152 μM, 0.00457 μM, 0.0137 μM, 0.0411 μM, 0.123 μM, 0.370 μM, 1.11 μM, 3.33 μM, 10 μM in DMSO) and the cells were incubated for 72 hours. The number of viable cells was determined by quantification of ATP in living cells using Cell Titer-Glo® (Promega, the USA) Luminescent Cell Viability Assay kit and thereby $GI_{50}$ was calculated. Experimental results were shown in Table 3. According to Table 3, Compound 5 and Compound 135 selectively inhibited acute myeloid leukemia cell lines having mutant FLT3-ITD but exhibited no effects against cell lines of other disease type. In addition, no toxic side effects were shown in normal hamster lung cells and ovary cells.

TABLE 3

| $GI_{50}$/μM | Example Compound 5 | Example Compound 135 |
|---|---|---|
| MEC-1 | >10 | >10 |
| MOLM13 | 0.267 | 0.466 |
| MV4-11 | 0.147 | 0.284 |
| MOLM14 | 0.333 | 0.343 |
| OCI-AML-3 | >10 | >10 |
| CHL | >10 | >10 |
| CHO | >10 | >10 |

It can be seen from Table 3 that Compound 3 and Compound 5 selectively and strongly inhibited human acute myeloid leukemia cell lines MOLM13, MOLM14 and MV4-11 that expressed FLT3-ITD.

Example 187: Effects of Compound 5 and Compound 135 on Upstream and Downstream Signaling Pathways of FLT3 in Cells In cells having FLT3 gene and/or FLT3/ITD mutant gene, specifically, human acute myeloid leukemia cells MV4-11 (expressing FLT3/ITD mutant gene) cell strain and human acute myeloid leukemia cells MOLM-13 and MOLM-14 (expressing FLT3/ITD mutant gene and wild-type FLT3 gene) cell strains, Compound 5, Compound 135 and a FLT3 kinase inhibitor, PKC412 (purchased from Hao Yuan Chemexpress Company, Shanghai), which was used as the control, were evaluated for their effects in cells on phosphorylation of FLT3 and FLT3/ITD protein kinase and phosphorylation of the closely-related STAT5 protein which is downstream of FLT3 signaling pathways, as well as their effects on phosphorylation of other relevant protein kinases such as ERK and AKT, by assaying a number of cellular biochemical and functional endpoints. In addition, the effects on C-Myc and phosphorylation of the transcription factor NF-κB subunit p65 was also examined (FIGS. 1a-1f). Compound 5 and Compound 135 at different concentrations (0 μM, 0.01 μM, 0.03 μM, 0.1 μM, 0.3 μM, 1 μM, 3 μM in DMSO) and the FLT3 kinase inhibitor PKC412 (1 μM in DMSO) were used to treat acute myeloid leukemia cells MV-4-11, MOLM13 and MOLM-14 that had FLT3 and/or FLT3/ITD gene for 4 hours, respectively, and then the samples were collected. The effects of the compounds on the phosphorylation of proteins such as STAT5, C-Myc, ERK, NF-κB p65, AKT in cells were tested (FIGS. 1a-1f).

The experimental results shown in FIGS. 1a-1f reflected that, both Compound 5 and Compound 135 were capable of inhibiting phosphorylation of the protein kinase FLT3 in MV-4-11, MOLM-13 and MOLM-14 cell lines. In addition, Compound 5 and Compound 135 also exhibited significant inhibition on phosphorylation of STAT5 which is a protein downstream of FLT3/ITD, and had significant effects on the degradation of C-Myc, which is a protein closely related to FLT3 protein kinase, in acute myeloid leukemia cells MV-4-11, MOLM13 and MOLM-14 that had FLT3 and/or FLT3/ITD gene. In the same experiment, the FLT3 kinase inhibitor PKC412, which served as the control compound, also strongly inhibited phosphorylation of the protein kinase FLT3 and STAT5 which is closely related to FLT3/ITD as well as c-Myc.

Example 187 suggested that both Compound 5 and Compound 135 were capable of suppressing phosphorylation of the protein kinase FLT3, affecting the phosphorylation of the protein STAT5 which is downstream of FLT3 signaling pathways, and further inhibiting cell proliferation of acute myeloid leukemia cell strains that had FLT3 and/or FLT3/ITD gene.

Example 188: Effects of Compound 5 and Compound 135 on Cell Apoptosis in Cells

In human acute myeloid leukemia cells MV4-11 (expressing FLT3/ITD mutant gene) cell strain and human acute myeloid leukemia cells MOLM-13 and MOLM-14 (expressing FLT3/ITD mutant gene and wild-type FLT3 gene) cell strains, the effects of Compound 5 and Compound 135 on protein cleavage of the DNA repairase poly(ADP-ribose) polymerase (PARP) and Caspase (cysteinyl aspartate-specific proteinase) 3 that were closely related to cell apoptosis were examined in cells in order to confirm whether the death of the cells after the administration was caused by apoptosis or necrosis. MOLM-13, MOLM-14, MV-4-11 cell strains were treated with Compound 5, Compound 135 (at different concentrations: 0 μM, 0.1 μM, 0.3 μM, 1 μM, 3 μM in DMSO) and the control compound PKC412 (purchased from MedChem Express) (1 μM in DMSO), respectively, and the cells were collected after 24 hours. Western Blot was used to detect the effects of different concentrations of compounds on protein cleavage of the DNA repairase poly (ADP-ribose) polymerase (PARP) and Caspase (cysteinyl aspartate-specific proteinase) 3. Results were shown in FIGS. 2a-2e.

As shown in FIGS. 2a-2e, for the three cell strains that had FLT3-ITD gene, when Compound 5 or Compound 135 was used at 1 μM, significant cleavage of the DNA repairase poly(ADP-ribose) polymerase (PARP) was observed after treatment of 24 hours. It was demonstrated that Compound 5 and Compound 135 were capable of causing apoptosis of leukemia cells that carry FLT3-ITD gene.

Example 189: Treating Acute Myeloid Leukemia with Compound 5 and Compound 135

In order to determine the inhibitory effect of Compound 5 and Compound 135 on tumors in vivo, a nude mouse model harboring subcutaneous tumor was introduced. 44 mice (5-week-old) (Balb/c-nu female mice, purchased from Shanghai Snake Experimental Animal Co., Ltd.) were inoculated subcutaneously with MV4-11 cells at $1 \times 10^7$ cells/mouse, and the changes in body weight and tumor volume were recorded daily (tumor volume=tumor length× tumor width×tumor width/2). 10 days later, the mice, of which tumor volumes reached 200 mm³, were randomized into seven groups with 5-9 mice in each group, and were treated as follows: the first group was administered daily by oral gavage with vehicle, i.e., methylcellulose-based aqueous suspension (purchased from Sinopharm Group Chemical Reagent Co., Ltd.); the second, third and the fourth groups were administered daily by oral gavage with 25 mg/kg, 50 mg/kg, 100 mg/kg of Compound 135 in a methylcellulose-based aqueous suspension formulation; the fifth, sixth and seventh groups were administered daily by oral gavage with 25 mg/kg, 50 mg/kg, 100 mg/kg of Compound 5 in a methylcellulose-based aqueous suspension formulation. The first day of administration was recorded as day 0, followed by continuous administration for four weeks (FIGS. 3a-3b).

Figure 3A:
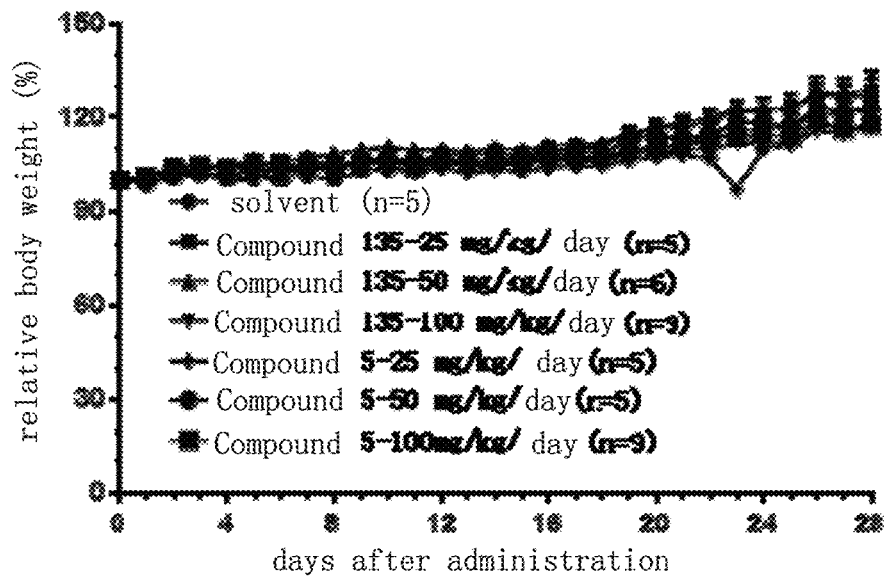
FIGS. 3a to 3b respectively illustrate the tumor inhibition effects of Compound 5 and Compound 138 in tumor-transplanted mice models bearing MV4-11 cells.
Figure 3B:
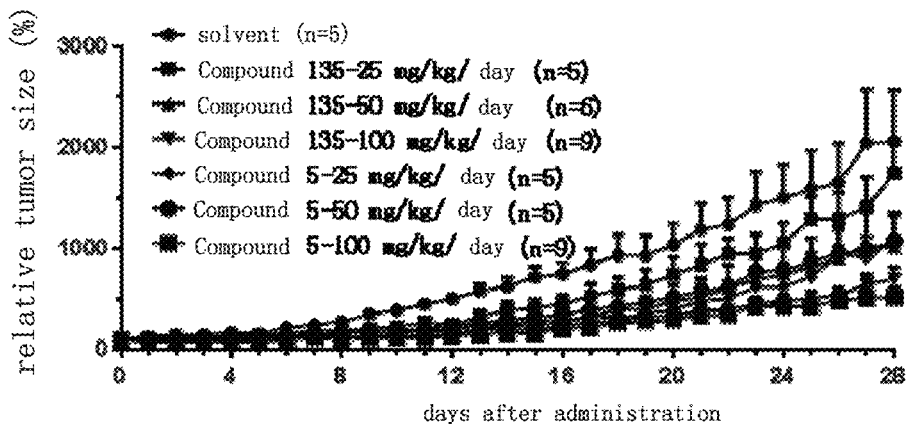

The experimental results were shown in FIG. 3a-3b. After being treated with Compound 5 and Compound 135, tumor growth in mice were significantly inhibited (FIGS. 3a-3b), wherein volume increase in 50 mg/kg/day mice groups was slowed significantly, and volume increase in 100 mg/kg/day mice groups was slowed vastly. The data obtained from the tumor-transplanted mouse model in this example demonstrated that Compound 5 and Compound 135 could strongly inhibiting acute myeloid leukemia (AML) tumor growth in vivo in mice.

INDUSTRIAL APPLICABILITY

The present invention provides a novel kinase inhibitor compound, which may be useful in reducing or inhibiting the activity of FLT3 kinase and/or mutant FLT3/ITD kinase in a cell or a subject, and/or for preventing or treating FLT3- and/or FLT3/ITD-related conditions in a subject. Therefore, it can be prepared into corresponding medicaments and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:

1. A kinase inhibitor, comprising a compound of Formula 1a or a pharmaceutically acceptable salt, solvate, ester, acid or prodrug thereof:

Formula Ia

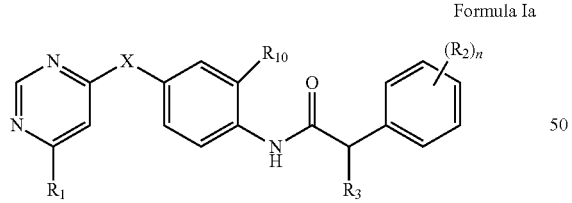

wherein X is selected from O, S, and NH; $R_1$ is selected from $C_{2-6}$acylamino and —$(NR_4)$-L-$R_5$; $(R_2)_n$ represents n independent $R_2$ substituents attached to the ortho-, meta-, or para-position of the benzene ring, wherein n is an integer of 0-3, $R_2$ is independently selected from halo, $C_{1-6}$alkyl, $C_{1-6}$haloalkyl, $C_{1-6}$alkoxy, phenoxy, hydroxy, and nitro, or two adjacent $R_2$ form together a benzene ring; $R_3$ is selected from hydrogen, hydroxy, and $C_{1-6}$alkyl; $R_{10}$ is hydrogen; $R_4$ is hydrogen; $R_5$ is selected from hydroxy and $C_{1-6}$alkoxy; L is selected from $C_{1-4}$ straight or branched alkylene.

2. The kinase inhibitor of claim 1, which is selected from compounds as follows, or a pharmaceutically acceptable salt, solvate, ester, acid or prodrug thereof:

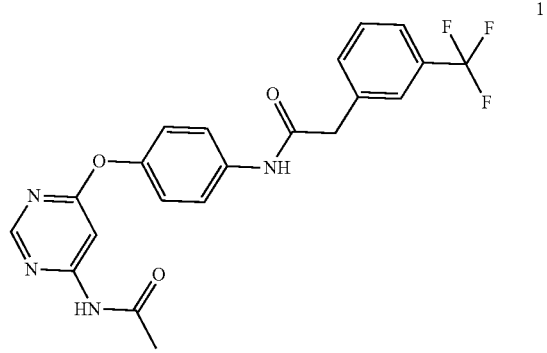

1

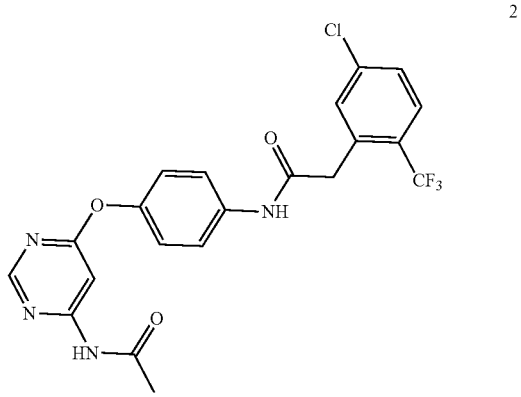

2

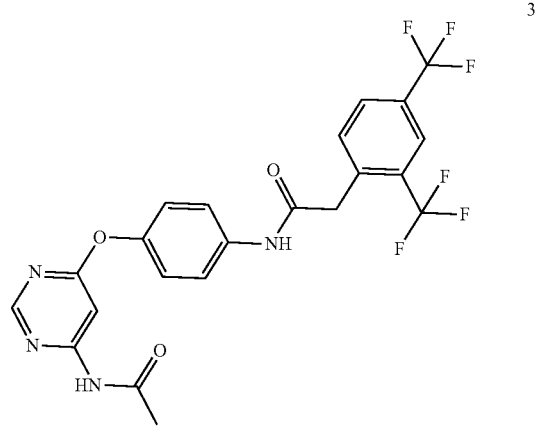

3

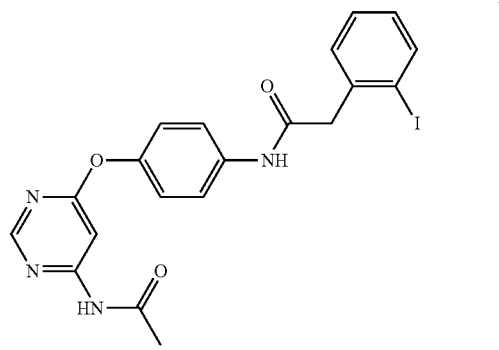

4

-continued
| 199 | 200 |
|---|---|
| 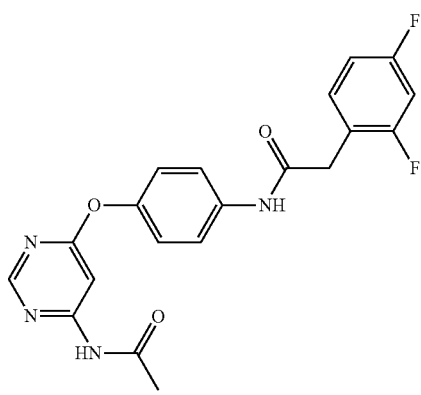 5 | 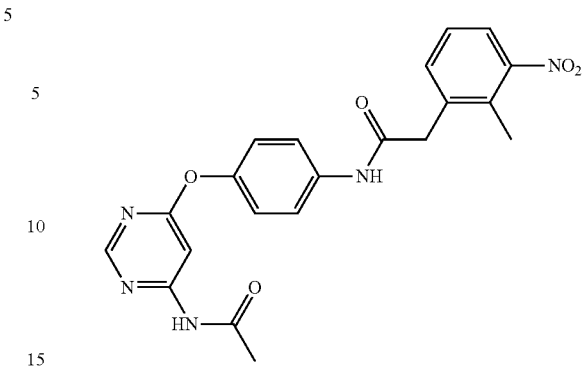 9 |
| 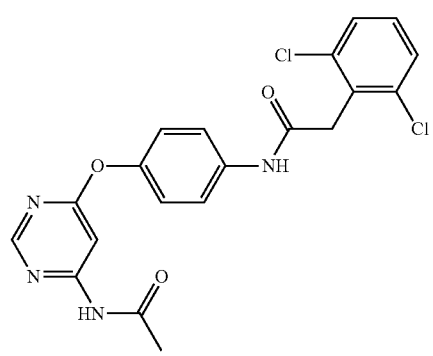 6 | 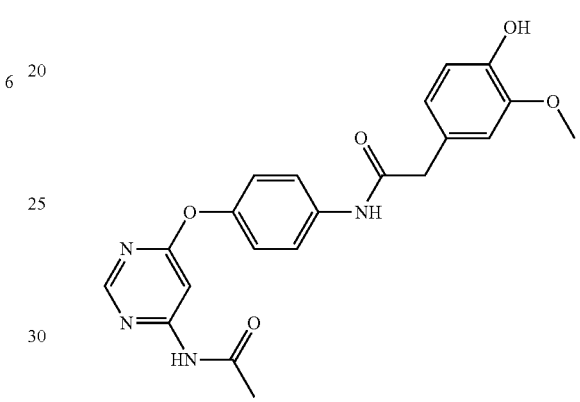 11 |
| 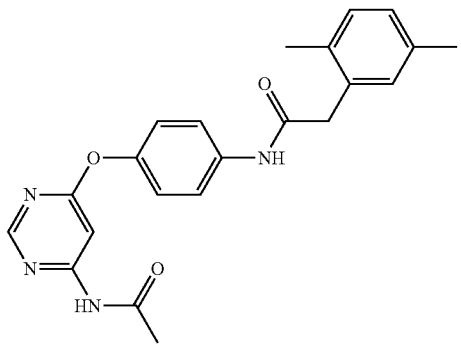 7 | 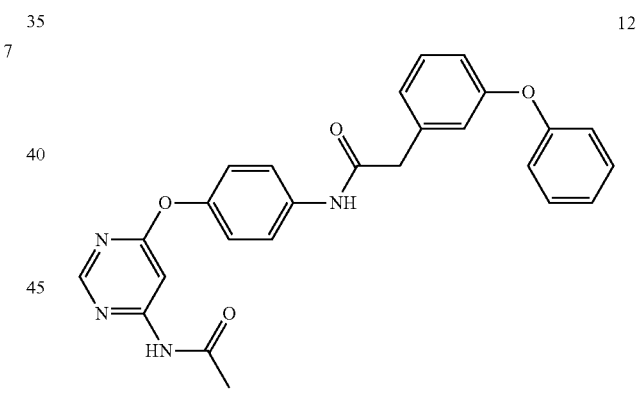 12 |
| 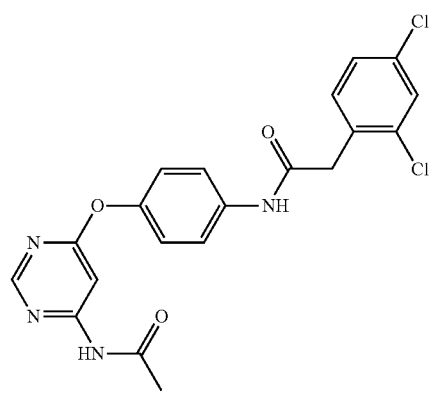 8 | 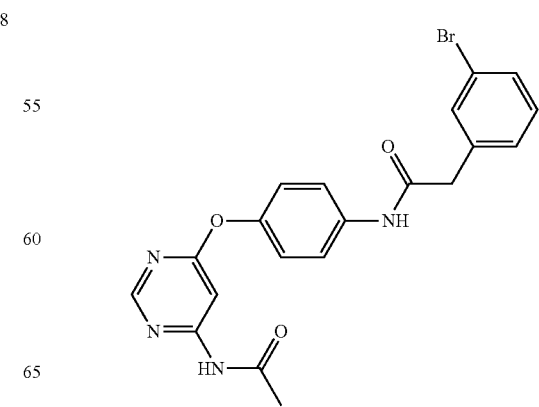 13 |

14
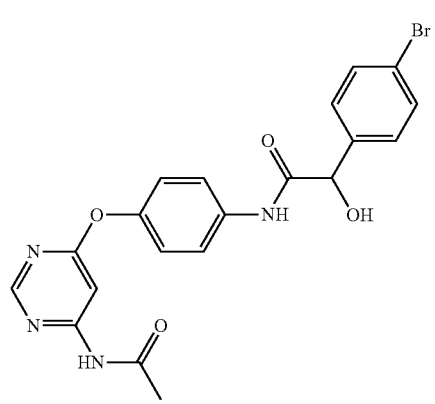
19
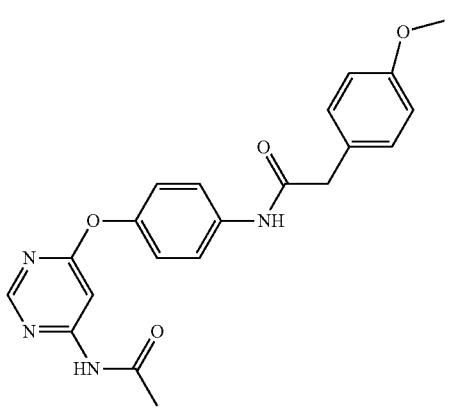
15
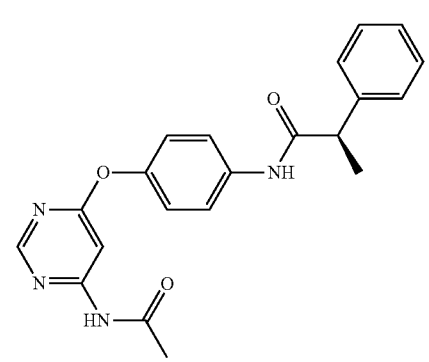
20
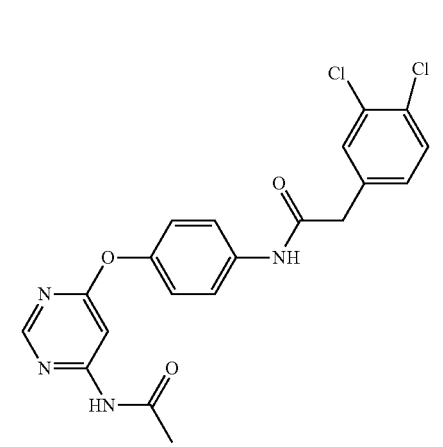
16
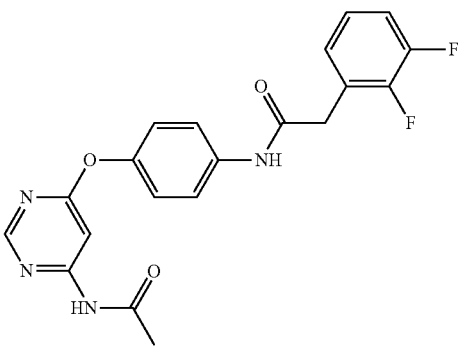
21
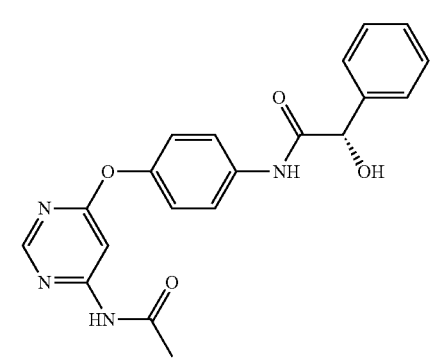
17
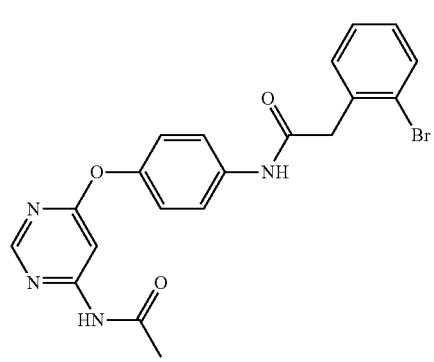
22
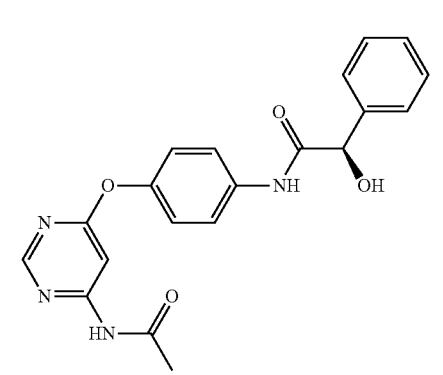

23
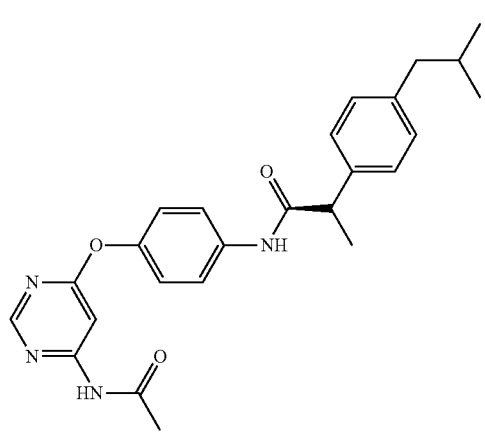
24
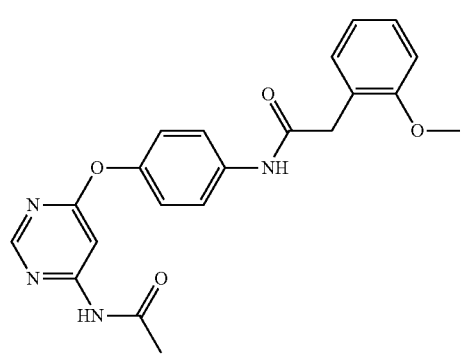
25
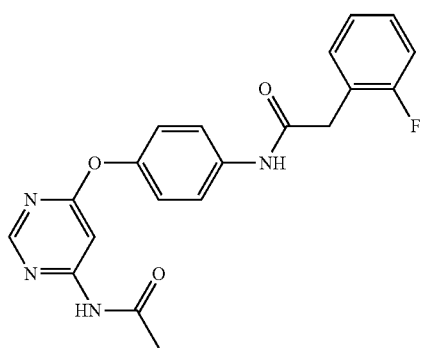
26
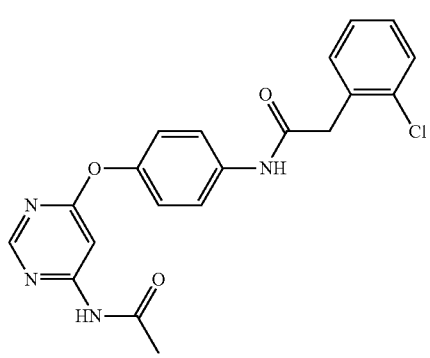
28
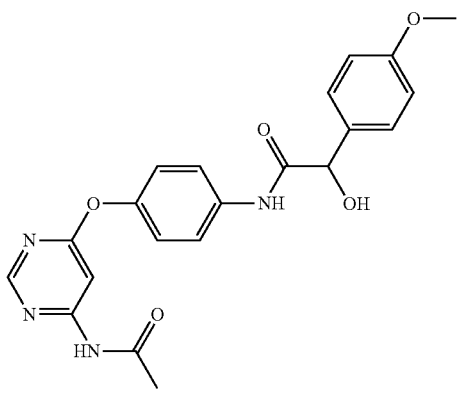
31
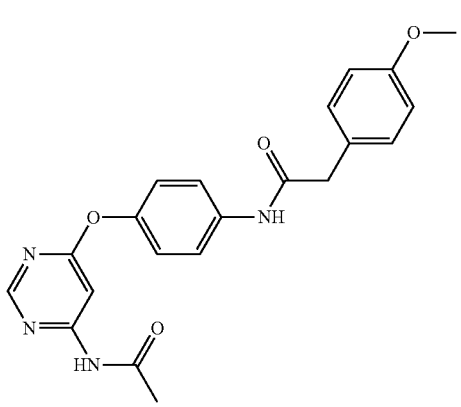
47
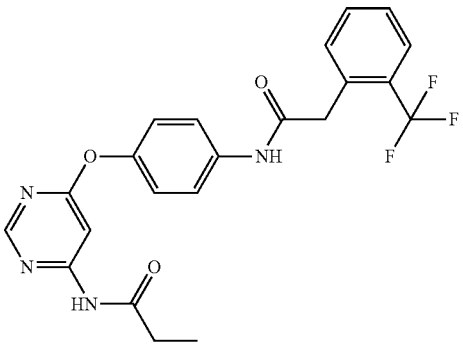
48
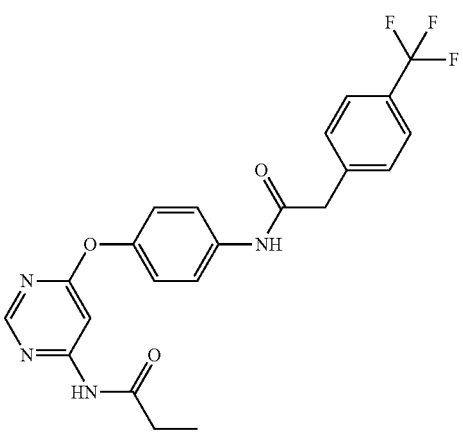

49
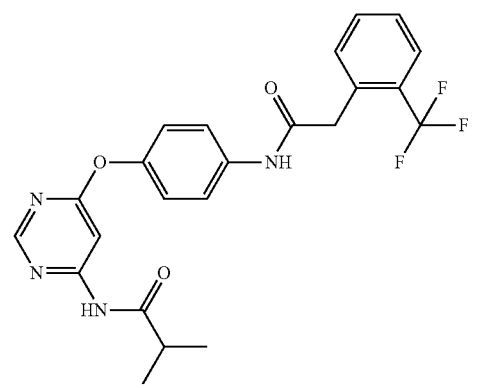
50
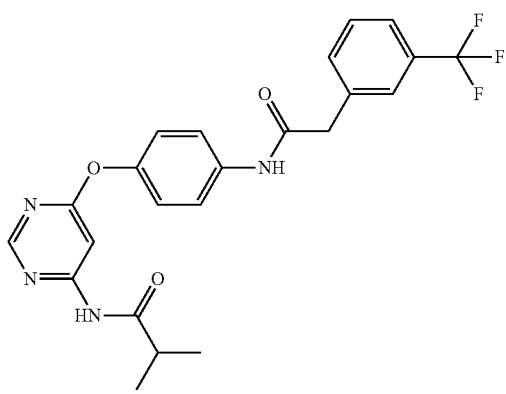
51
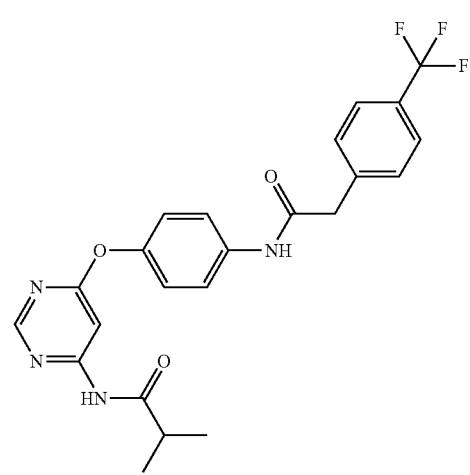
52
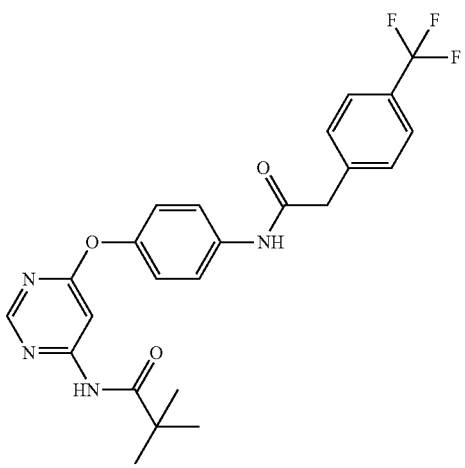
53
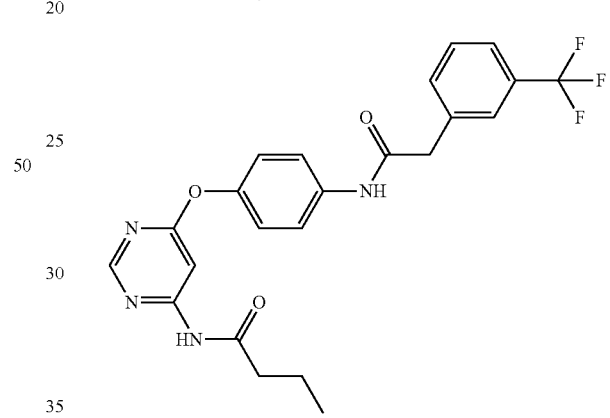
54
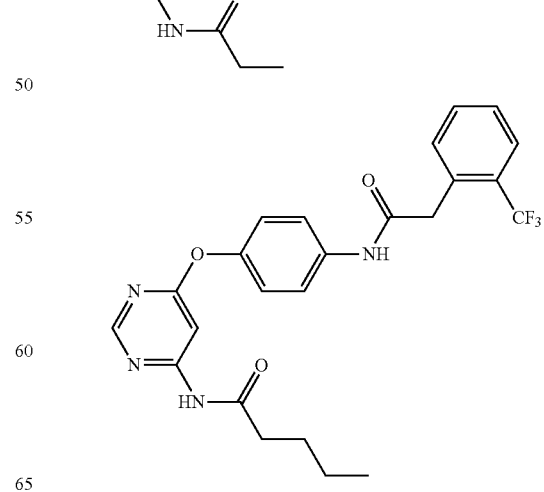

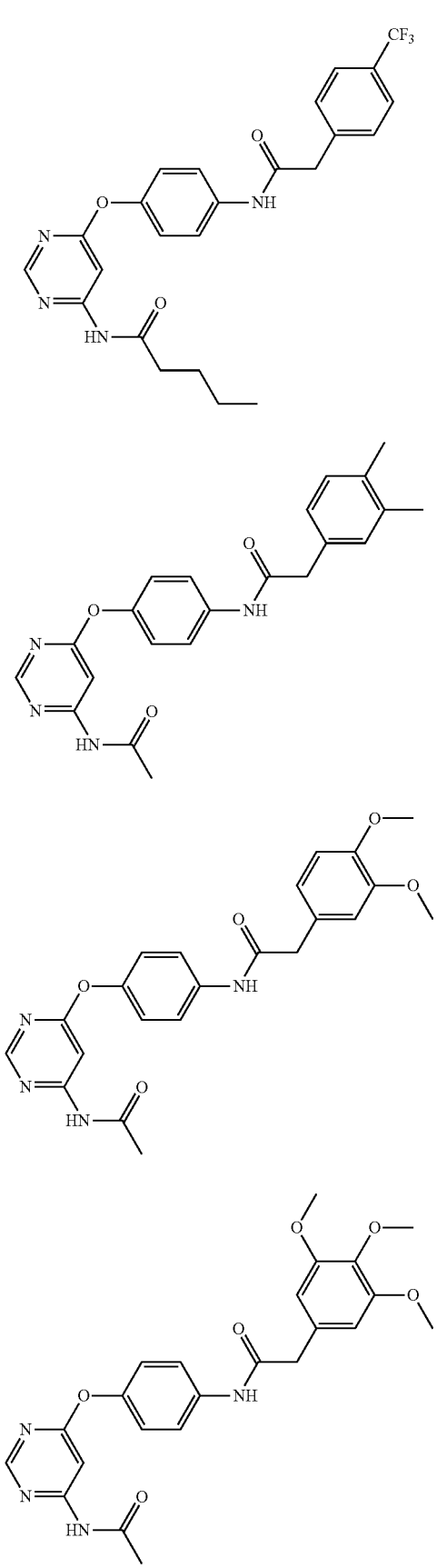
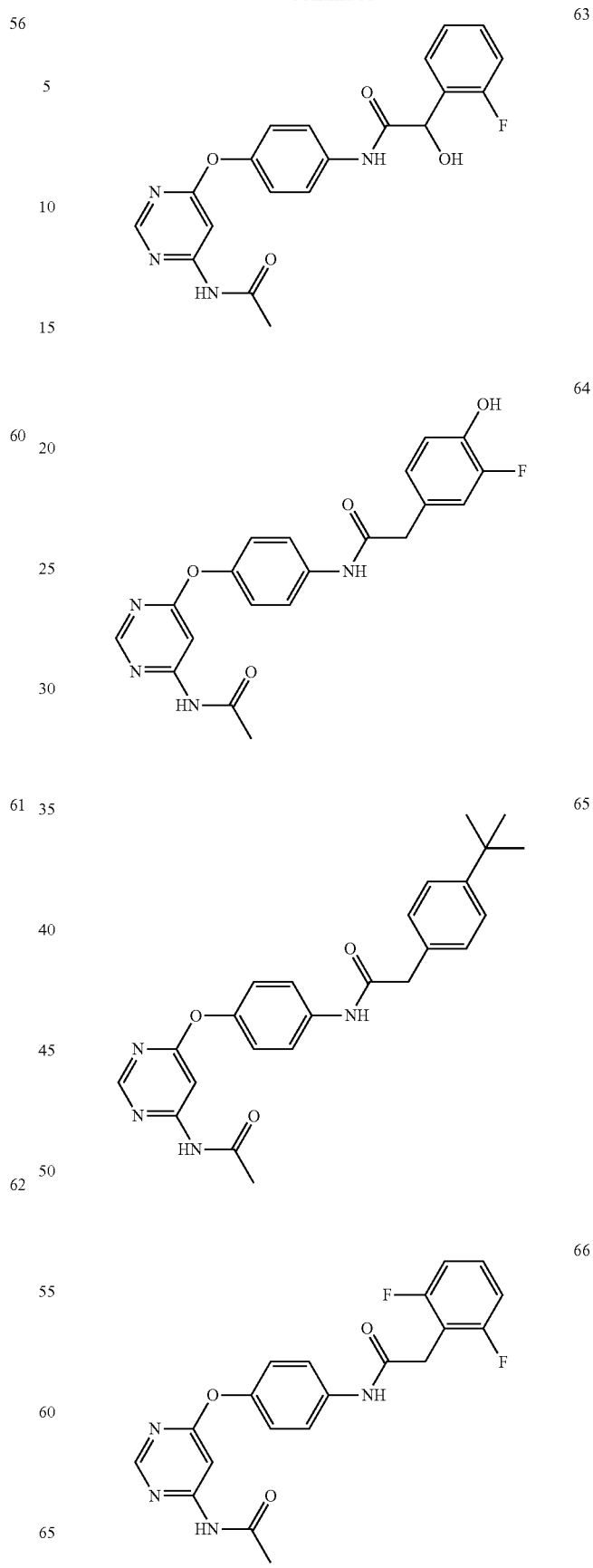

67
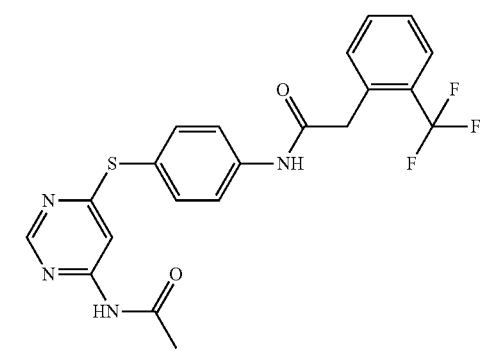
68
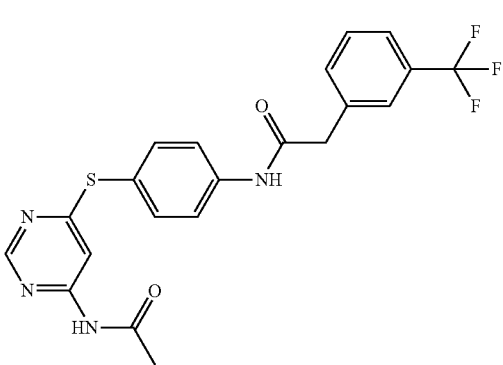
69
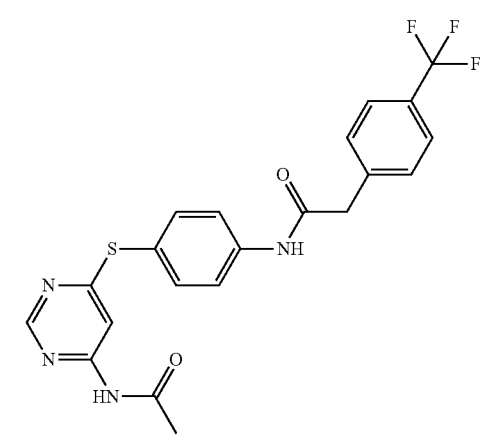
76
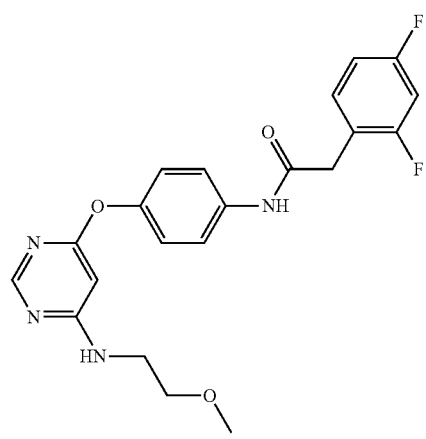
77
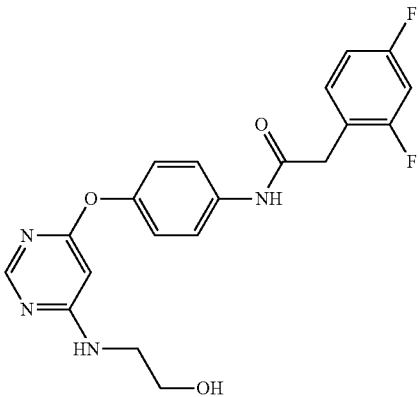
133
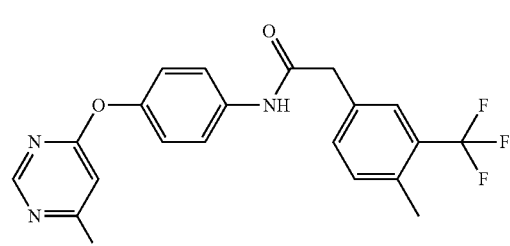
134
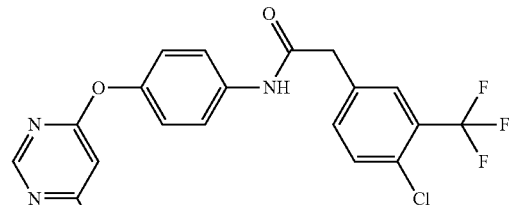
135
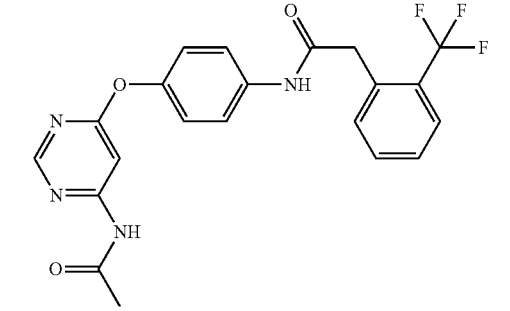

| 136 | 164 |
| 161 | 165 |
| 162 | 166 |
| 163 | 167 |

168

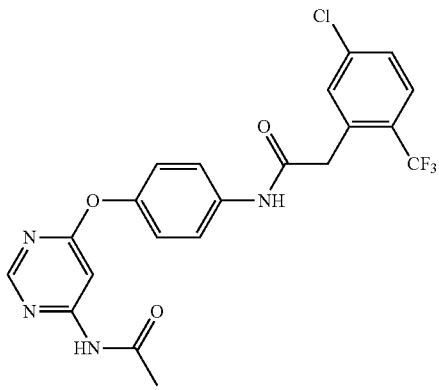

175

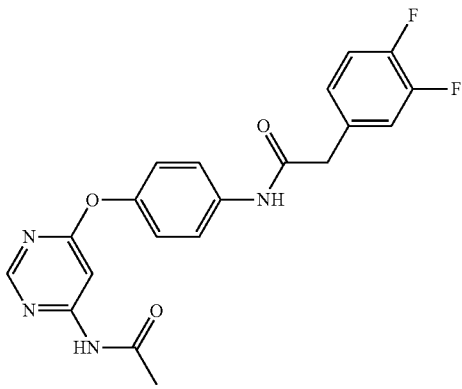

169

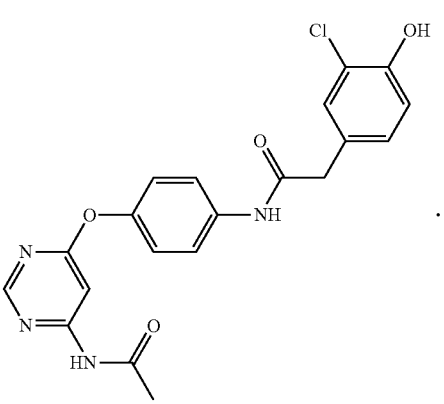

176

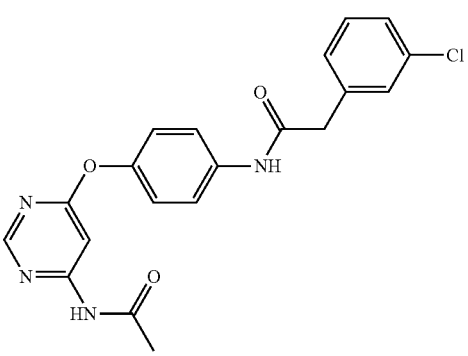

170

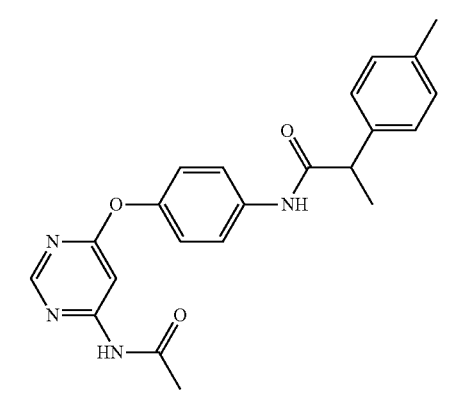

173

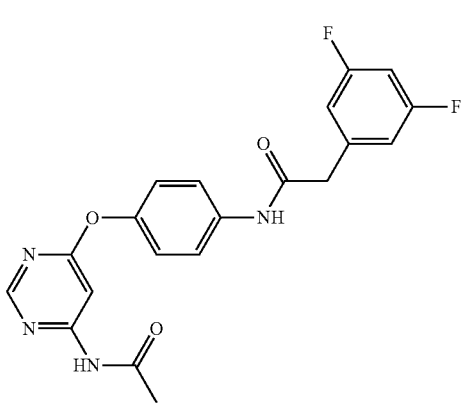

3. A pharmaceutical composition, comprising the kinase inhibitor of claim 1 and a pharmaceutically acceptable carrier or excipient as well as optional therapeutic agents.

4. A method for inhibiting activity of tyrosine kinase FLT3, FLT3-ITD, PDGFRα and/or PDGFRβ in a cell or a subject, wherein the method comprises administering the kinase inhibitor of claim 1 to the cell or the subject.

5. A method for treating a condition associated with activity of FLT3, FLT3-ITD, PDGFRα and/or PDGFRβ kinase in a subject, wherein the method comprises administering the kinase inhibitor of claim 1 to the subject.

6. The method of claim 5, wherein the condition is associated with activity of FLT3/ITD mutant kinase.

7. The method of claim 5, wherein the condition is selected from: initiation or progression of solid tumor, B-cell lymphoma, sarcoma, diffuse large B-cell lymphoma, follicular lymphoma, chronic lymphocytic lymphoma, anaplastic large-cell lymphoma, acute myeloid leukemia, acute lymphocytic leukemia, acute granulocytic leukemia, acute promyelocytic leukemia, chronic lymphocytic leukemia, chronic myeloid leukemia, chronic neutrophilic leukemia, acute undifferentiated leukemia, B-cell prolymphocytic leukemia, adult T-cell acute lymphocytic leukemia, acute myeloid leukemia with trilineage myelodysplasia, mixed lineage leukemia, lymphoplasmacytic lymphoma/Waldenström macroglobulinemia, splenic marginal zone lymphoma, plasma cell myeloma, plasmacytoma, extranodal marginal zone B-cell lymphoma, nodal marginal zone B-cell lymphoma, mantle cell lymphoma, mediastinal (thymic) large B-cell lymphoma, intravascular large B-cell lymphoma, primary effusion lymphoma, Burkitt lymphoma, lymphomatoid granulomatosis, breast ductal carcinoma, lobular carcinoma, adenocarcinoma, melanoma, B-cell proliferative disease, brain cancer, kidney cancer, liver cancer, adrenal gland cancer, bladder cancer, breast cancer, lymphoma, stomach cancer, stomach neoplasm, esophagus cancer, ovarian cancer, colorectal cancer, prostate cancer, pancreas cancer, lung cancer, vagina cancer, membranous adenocarcinoma, thyroid cancer, neck cancer, Central Nervous System Cancer, malignant glioma, myeloproliferative disease, myeloproliferative disorders, myelodysplasia syndromes, glioblastoma, multiple myeloma and myeloid sarcoma, gastrointestinal cancer, head and neck neoplasms, brain tumor, epidermal hyperplasia, psoriasis, prostate hyperplasia, neoplasia, neoplasia of epithelial character, Hodgkin's disease and combination thereof.

8. The method of claim 5, wherein the condition is acute myeloid leukemia.

* * * * *